United States Patent [19]
Lohray et al.

[11] Patent Number: 6,051,570
[45] Date of Patent: Apr. 18, 2000

[54] BENZIMIDAZOLE DERIVATIVES AS ANTIULCER AGENTS, PROCESS FOR THEIR PREPARATION AND PHARMACEUTICAL COMPOSITIONS CONTAINING THEM

[75] Inventors: Braj Bhushan Lohray; Vidya Bhushan Lohray; Prasuna Guntupalli; Narayan Reddy Kommireddi; Prem Kumar Mamnoor; Rajagopalan Ramanujam, all of Andhra Pradesh, India

[73] Assignees: Dr. Reddy's Research Foundation, Hyderabad, India; Reddy-Cheminor, Inc., Ridgewood, N.J.

[21] Appl. No.: 09/041,191

[22] Filed: Mar. 10, 1998

[51] Int. Cl.$^7$ .................. A61K 31/55; A61K 31/535; C07D 403/14; C07D 413/14
[52] U.S. Cl. .................. 514/212; 514/234.5; 514/254; 514/278; 514/316; 514/318; 514/338; 540/597; 540/598; 544/124; 544/364; 546/19; 546/187; 546/193; 546/273.7
[58] Field of Search .................. 540/597, 598; 544/124, 364; 546/19, 187, 193, 273.7; 514/212, 254, 234.5, 278, 316, 318, 338

[56] References Cited

U.S. PATENT DOCUMENTS

| | | | |
|---|---|---|---|
| 4,255,431 | 3/1981 | Junggren | 424/263 |
| 4,689,333 | 8/1987 | Nohara | 514/338 |
| 4,758,579 | 7/1988 | Kohl | 514/338 |
| 4,818,760 | 4/1989 | Binder | 514/338 |
| 5,045,552 | 9/1991 | Souda | 514/338 |
| 5,587,389 | 12/1996 | Kohl | 514/338 |

FOREIGN PATENT DOCUMENTS

| | | |
|---|---|---|
| 0005129 | 10/1979 | European Pat. Off. . |
| 174726 | 3/1986 | European Pat. Off. . |
| 208452 | 1/1987 | European Pat. Off. . |
| 218336 | 4/1987 | European Pat. Off. . |
| 246774 | 11/1987 | European Pat. Off. . |
| 254588 | 1/1988 | European Pat. Off. . |
| 298440 | 1/1989 | European Pat. Off. . |
| 0385850 | 9/1990 | European Pat. Off. . |
| 434999 | 7/1991 | European Pat. Off. . |
| 786461 | 7/1997 | European Pat. Off. . |
| 61-085383 | 4/1986 | Japan . |
| 108879 | 5/1987 | Japan . |
| 211581 | 8/1989 | Japan . |
| 2295614 | 6/1996 | United Kingdom . |
| 8803921 | 6/1988 | WIPO . |
| 8911479 | 11/1989 | WIPO . |
| 9119712 | 12/1991 | WIPO . |
| 9515324 | 6/1995 | WIPO . |
| 9515962 | 6/1995 | WIPO . |
| 9523140 | 8/1995 | WIPO . |
| 9602534 | 2/1996 | WIPO . |
| 9603402 | 2/1996 | WIPO . |
| 9603403 | 2/1996 | WIPO . |
| 9700875 | 1/1997 | WIPO . |
| 9702261 | 1/1997 | WIPO . |

OTHER PUBLICATIONS

Chemical Abstract, vol. 107, 1987 p. 693, Abstract 107:96720m (Corresponding to JP 62/108879).

Chemical Abstract, vol. 112, 1990 p. 716–717, Abstract #198378b (Corresponding to JP 01/211,581).

Sih, John C., et al. "Studies on (H+K+)–ATPase Inhibitors . . . " Journal of Medicinal Chemistry, vol. 34, No. 3 (1991), pp. 1049–1062.

Kohl, Bernhard, et al. "H+,K+)–ATPase Inhibiting 2–[(2–Pyridylmetghyl)sulfinyl]. . . " Journal of Medicinal Chemistry, vol. 35, No. 6, (1992), pp. 1049–1057.

Terashima, K. et al., "Studies on Antiulcer Agents. I. Synthesis and Pharmacological . . . " Chem. Pharm. Bull, vol. 43, No. 1, (1995), pp. 166–168.

Uchida, M., et al. "Studies on Proton Pump Inhibitors. III. Synthesis . . . " Chem. Pharm. Bull, vol. 38, No. 2, (1990), pp. 534–537.

Uchida, M., et al. "Synthesis and Antiulcer Activity of 4–Substituted 8–[(2–Benzimidazolyl) sulfinylmethyl]. . . " Chem. Pharm. Bull., vol. 36, No. 6, (1990), pp. 1575–1586.

Uchida, M., et al. "Studies on Proton Pump Inhibitors. II. Synthesis and Antiulcer Activity of 8–[(2–Benzimidazolyl) sulfinylmethyl]. . . " Chem. Pharm. Bull., vol. 37, No. 8, (1989), pp. 2109–2116.

Uchida, M., et al. "Studies on Proton Pump Inhibitors. I. Synthesis of 8–[(2–Benzinndazolyl)sulfinyl]–5,6,7,8 . . . " Chem. Pharm. Bull., vol. 37, No. 6, (1989), pp. 1517–1523.

Ife, Robert J., et al. "2–[[(4–Amino–2–pyridyl)methyl]sulfinyl]benzimidazole H+/K+–ATPase Inhibitors . . . " Journal of Medicinal Chemistry, vol. 32, No. 8, (1989), pp. 1970–1977.

*Primary Examiner*—Evelyn Mei Huang
*Attorney, Agent, or Firm*—Ladas & Parry

[57] ABSTRACT

This invention particularly relates to novel pyridylmethylsulfinyl benzimidazole represented by the general formula (I), its tautomers, its derivatives, its analogs, its stereoisomers, its polymorphs, its pharmaceutically acceptable salts, its pharmaceutically acceptable solvates and pharmaceutical compositions containing them and the use thereof.

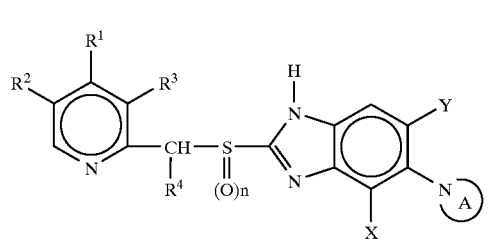

(I)

The present invention also relates to a process for the preparation of the above said novel pyridylmethylsulfinyl benzimidazoles and pharmaceutical compositions containing them.

25 Claims, No Drawings

BENZIMIDAZOLE DERIVATIVES AS ANTIULCER AGENTS, PROCESS FOR THEIR PREPARATION AND PHARMACEUTICAL COMPOSITIONS CONTAINING THEM

FIELD OF THE INVENTION

The present invention relates to novel anti-ulcer compounds, their tautomers, their derivatives, their analogs, their stereoisomers, their polymorphs, their pharmaceutically acceptable salts, pharmaceutically acceptable solvates and pharmaceutical compositions containing them.

This invention particularly relates to novel pyridylmethylsulfinyl benzimidazole represented by the general formula (I), its tautomers, its derivatives, its analogs, its stereoisomers, its polymorphs, its pharmaceutically acceptable salts, its pharmaceutically acceptable solvates and pharmaceutical compositions containing them.

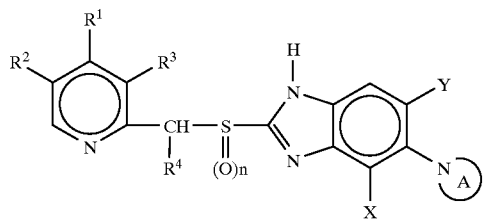

(I)

The present invention also relates to a process for the preparation of the above said novel pyridylmethylsulfinyl benzimidazoles of the general formula (I), its tautomers, its derivatives, its analogs, its stereoisomers, its polymorphs, its pharmaceutically acceptable salts, its pharmaceutically acceptable solvates and pharmaceutical compositions containing them.

The pyridylmethylsulfinyl benzimidazole derivatives of general formula (I) of the present invention are useful for prophylaxis and/or the treatment of the gastric and duodenal ulcers, as cytoprotective agents for the gastrointestinal tract and as antibacterial agents, more specifically as bactericides for Helicobacter pylori. More specifically, the pyridylmethylsulfinyl benzimidazole derivatives of general formula (I) of the present invention appear to inhibit the gastric acid secretion by blocking the proton pump of $H^+/K^+$-ATPase, an enzyme present in the parietal cells of the stomach although there may be alternative mechanisms of action.

The present invention also relates to a process for the preparation of the above said novel pyridylmethylsulfinyl benzimidazoles of general formula (I), its tautomers, its derivatives, its analogs, its stereoisomers, its polymorphs, its pharmaceutically acceptable salts, its pharmaceutically acceptable solvates, and novel intermediates.

BACKGROUND OF THE INVENTION

Gastric and duodenal ulcers are gastro intestinal diseases caused by various factors such as mental stress, dietary habits, intake of irritable food etc. The ulcers are caused due to damage of gastric membrane because of excess secretion of gastric acid.

The therapeutic agents which have been commonly used for the treatment of ulcers are antacids for neutralizing gastric acid, antipepsin agents for protecting the gastric mucous membrane and anticholinergic agents for inhibiting gastric acid secretion. At the present time, Histamine-$H_2$-receptor antagonists have been widely used for treating gastric and duodenal ulcers.

More recently, proton pump inhibitors are gaining importance since they block the proton pump of $H^+/K^+$-ATPase, an enzyme specifically present in the parietal cells of the stomach to inhibit the gastric acid secretion at the final stage. One of the earliest proton pump inhibitors is 2-[[(4-methoxy-3,5-dimethyl)pyridin-2-yl]methylsulfinyl]-5-methoxy-1H-benzimidazole whose generic name is Omeprazole (see Patent Application. Nos. EP 0 005 129; JP 79,141,783 and U.S. Pat. No. 4,255,43 1) having the following, formula (II) which is being, used to treat the above mentioned disease conditions.

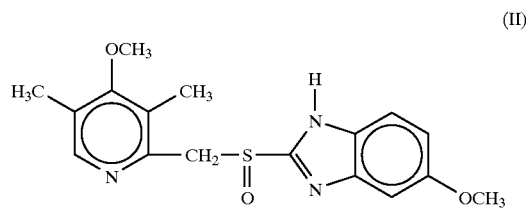

(II)

A wide variety of compounds related to Omeprazole having a pyridylmethylsulfinyl benzimidazole structure are described in various patent documents.

A group of compounds having general formula (IIa) wherein $R^1$ represents hydrogen, methoxy or trifluoromethyl, $R^2$ and $R^3$ independently represent hydrogen or methyl, $R^4$ represents fluoroalkyl and n is an integer of 0 to 1 have been described in European Patent application No. 0 174 726.

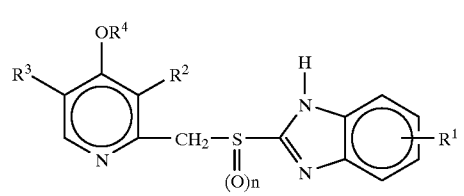

(IIa)

An example of these compounds is Lansoprazole shown in formula (IIb).

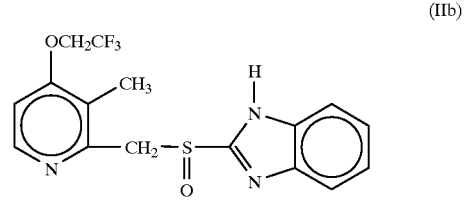

(IIb)

A group of compounds having general formula (IIc) wherein $R^1$ represents $(C_1-C_3)$alkyl which is completely or predominantly substituted by fluorine or a chlorodifluoromethyl radical, $R^2$ represents hydrogen, halo, trifluoromethyl, $(C_1-C_3)$alkyl, $(C_1-C_3)$alkoxy which is completely or predominantly substituted by fluorine, $R^1$ and $R^2$ together with the oxygen atom to which $R^1$ is bonded are $(C_1-C_2)$ alkylenedioxy which is optionally or completely substituted by fluorine or chlorotrifluoroethylenedioxy, one of $R^3$ and $R^5$ represents $(C_1-C_3)$alkoxy and the other represents hydrogen atom or $(C_1-C_3)$alkyl, and the $R^4$ is $(C_1-C_3)$alkoxy and n is an integer of 0 to 1 are disclosed in U.S. Pat. No. 4,758,579.

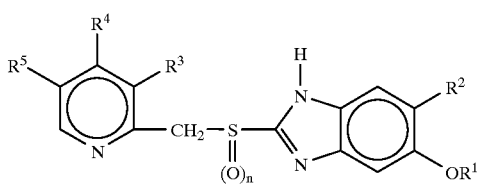

An example of these compounds is Pantoprazole shown in formula (IId)

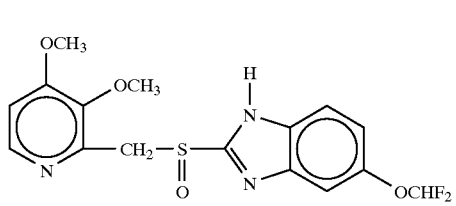

A group of compounds having general formula (IIe) where J, K represents hydrogen or alkyl, $R^1$, $R^2$ represents hydrogen, alkyl, alkoxy, halo, haloalkyl, alkoxycarbonyl or $CO_2H$, X represents oxygen, sulfur or $NR^3$, where $R^3$ represents hydrogen, alkyl, Ph, $PhCH_2$ or alkoxycarbonyl, Z represents $O(CH_2)_pOR^4$, $O(CH_2)_qR^5$, $O(CH_2)_rO(CH_2)_sOR^6$, $SO_tA$, $NR^8CH_2Ph$, $OR^9$, succinimidyl etc., A represents alkyl, alkoxycarbonyl, pyridyl, furyl, $(CH_2)_wC_6H_4R^7$, 2-benzimidazolyl or 2-benzothiazolyl etc., $R^4$ represents hydrogen, alkyl, aryl or aralkyl, $R^5$ represents halo, alkoxycarbonyl, aryl or heteroaryl, $R^6$ represents hydrogen or alkyl, $R^7$ represents hydrogen, alkyl, alkoxy or halo, $R^8$ represents alkyl or acetyl, $R^9$ represents hydrogen, alkyl or aryl, m is an integer of 2 to 10, n and t is of 0 to 2, p and q is of 1 to 3, r is of 1 to 5 and w is 0 to 1 are disclosed in U.S. Pat. No. 5,045,552.

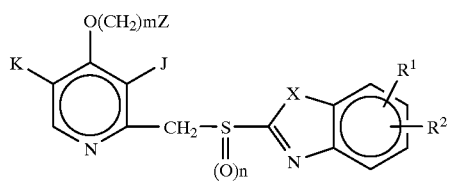

An example of these compounds is Rabeprazole shown in formula (IIf).

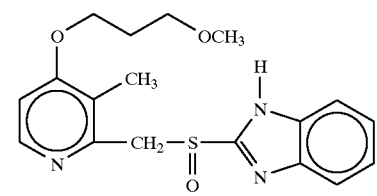

A group of compounds having general formula (IIg) where R represents a hydrogen atom, or lower alkyl group; $R^1$ represents a hydrogen atom, halogen atom, lower alkcoxy group, lower cycloalkoxy group, amido group, substituted phenoxy group, substituted benzyloxy group, lower alkoxy group optionally containing halogen atoms, nitro group, hydroxyl group, lower alkenyloxy group, lower alkylthio group or a group —$NR^4R^5$, wherein $R^4$, $R^1$ may be same or different and each represent a hydrogen atom, lower alkyl group, or R4, R5 mutually combine together with the nitrogen atom adjacent thereto form a 5–6 membered cyclic structure ; $R^2$ represents hydrogen, halogen, lower alkyl group, optionally containing halogen atom, lower alkoxy group, optionally containing halogen atom, hydroxyl group, acyl group, lower alkoxycarbonyl group, nitro group, or amino group; $R^3$ represents a hydrogen, lower alkyl group, lower alkoxymethyl group, lower alkylcarbonyl group, lower alkoxycarbonyl group, carbamoyl group, lower alkylcarbamoyl group, lower alkylcarbonylmethyl group, lower alkoxycarbonylmethyl group, lower acyloxymethyl group, or lower alkylsulfonyl group; n represents 0 or 1 and A represents a methine carbon or nitrogen are disclosed in European Patent application No. 0 434 999.

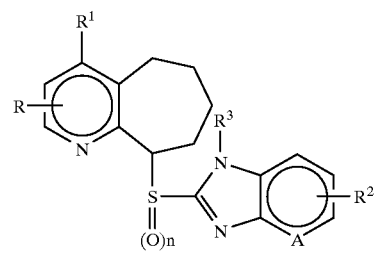

An example of these compounds is Nepaprazole shown in formula (IIh).

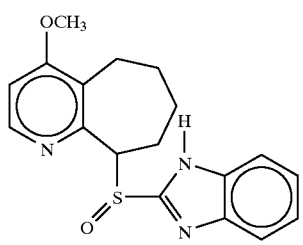

A group of compounds having, general formula (IIi) where $R^1$ represents a straight chain or branched ($C_1$–$C_8$) alkoxy which may be substituted with cycloalkyl or ($C_2$–$C_4$) fluoroalkoxy, $R^2$ represents hydrogen, methyl or methoxy, $R^3$ and $R^4$ represent hydrogen or methyl and may be the same or different are disclosed in European Patent application No. 0 254 588.

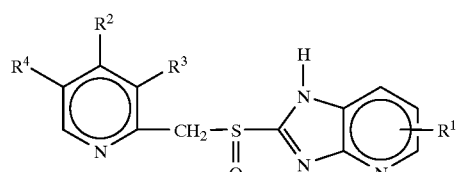

An example of these compounds is shown in formula (IIj)

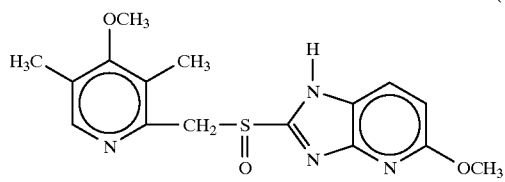

(IIj)

A group of compounds having general formula (IIk) where $R^1$ to $R^4$ represents hydrogen, $(C_1-C_6)$alkyl, $(C_1-C_6)$alkoxy, $(C_1-C_6)$alkanoyl, $(C_1-C_6)$alkoxycarbonyl, halo, fluoroalkyl, fluoroalkoxy, or R2 and R3 together form a group $—O(CR_2)_mO—$, R is hydrogen or fluorine, m is 1 or 2, $R^5$ and $R^6$ represents hydrogen, $(C_1-C_6)$alkyl, or $(C_3-C_6)$cycloalkyl, $R^5$ and $R^6$ together with the nitrogen atom to which they are attached form an azetidino, pyrrolidino, piperazino, N-$(C_1-C_4)$alkylpiperazino, piperidino, or morpholino group, and one of $R^7$ and $R^8$ is fluorine and the other is hydrogen, fluorine, or $(C_1-C_6)$alkyl and n is an integer of 0 to 2 are disclosed in European Patent application No. 0 246 774.

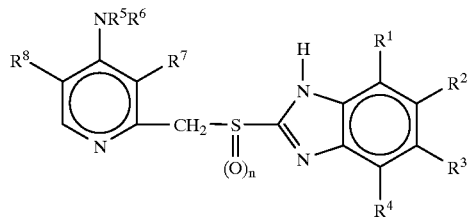

(IIk)

An example of this class of compounds is shown in formula (III)

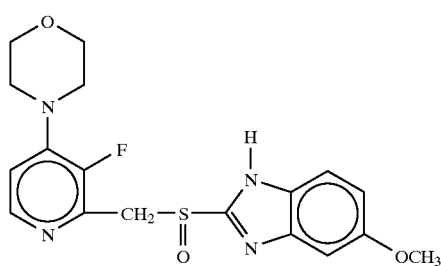

(III)

A group of compounds having general formula (IIm) where R represents hydrogen or alkanoyl group and n is an integer ranging from 0 to 2, are disclosed in the Japanese Patent application No. 62,108,879.

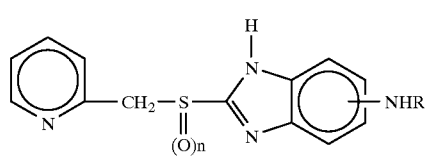

(IIm)

An example of this class of compounds is shown in formula (IIn)

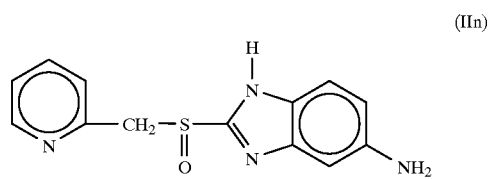

(IIn)

A group of compounds having general formula (IIo) where A denotes —CH=CH— or S and, $R^1$, $R^3$ and $R^4$ represents independently of one another, denote hydrogen, or lower alkyl group, $R^2$ represents hydrogen or lower alkoxy group and n is an integer ranging from 0 to 1 are disclosed in U.S. Pat. No. 4,818,760.

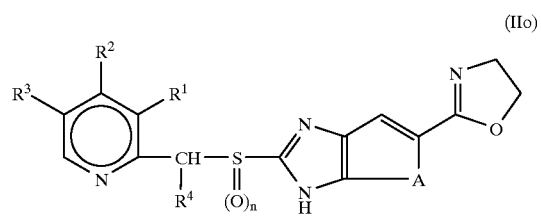

(IIo)

An example of this class of compounds is shown in formula (IIp).

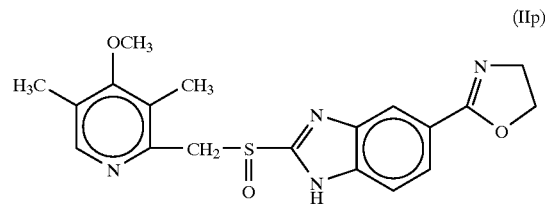

(IIp)

A group of compounds having general formula (IIq) where X represents S, SO or $SO_2$; Y represents halogen; $R^1$ and $R^2$ are independently hydrogen, or alkyl group; $R^3$ represents hydrogen, $(C_1-C_8)$alkyl, $SR^6$, $N(R^7)_2$, 1-piperidinyl, 4-morpholinyl, 4-methylpiperazin-1-yl, 1-pyrrolidinyl, or a group of formula $OR^6$ or $—O(CH_2)_m-Z$, wherein $R^6$ represent $(C_1-C_4)$alkyl, $(C_2-C_4)$alkenyl, optionally substituted $(C_3-C_{10})$cycloalkyl, $(C_2-C_5)$fluoroalkyl or phenyl or benzyl, each of which is independently substituted with one or more halogen or $(C_1-C_4)$alkyl or alkoxy optionally substituted with halogen, $R^7$ is hydrogen or $(C_1-C_5)$ alkyl, Z represents a group of formula $O(CH_2)_pOR^8$, $O(CH_2)_qR^9$ or $O(CH_2)_rO(CH_2)_sOR^{10}$ wherein p and q are independently an integer 1 to 3, r and s are independently an integer 1 to 5, $R^8$ represents hydrogen, lower alkyl, aryl or aralkyl, $R^9$ is hydrogen, alkoxycarbonyl, aryl or heteroaryl and $R^{10}$ is hydrogen or lower alkyl, m is an integer of 2 to 10; and $R^4$ and $R^5$ independently from each other represent hydrogen or $(C_1-C_5)$alkyl or $R^4$ and $R^3$ together with the carbon atoms adjacent to the pyridine ring form a ring, $R^3$ and $R^5$ or $R^4$ and $R^3$ together represent —CH=CH—CH=CH—, $O(CH_2)_n$, $O(CH_2)_nO$, $CH_2(CH_2)n$ or OCH=CH—, wherein n represents an integer of 1 to 4 are disclosed in Patent application No. GB 2 295 614.

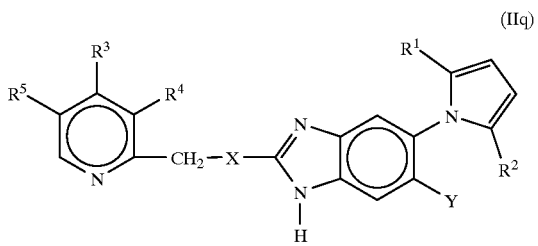

(IIq)

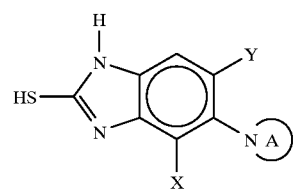

(IV)

An example of this class of compounds is shown in formula (IIr)

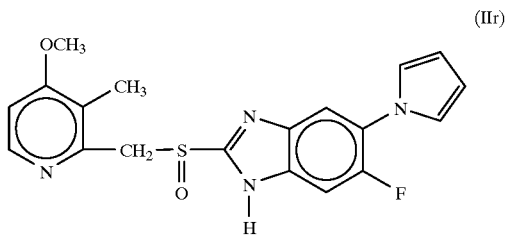

(IIr)

SUMMARY OF THE INVENTION

The above mentioned compounds are highly effective for the treatment of gastrointestinal disorders. But it has been suggested that because of their longer duration of action or in other words the irreversible binding to the $H^+/K^+$-ATPase enzyme may lead to potentially serious side effects for example gastric carcinoids (Ref: Scand. J. Gastroenterol., 1985, 20, 53).

Therefore, we focussed our research effort for developing novel compounds for prophylaxis and/or the treatment of ulcers, as cytoprotective agents for gastrointestinal tract and as antibacterial agents, more specifically as bactericides for Helicobacter pylori, for inhibiting gastric acid secretion, which may have shorter duration of action.

The main objective of the present invention is therefore, to provide novel pyridylmethylsulfinyl benzimidazoles of the general formula (I), its derivatives, its analogs, its tautomers, its various isomers, its polymorphs, its pharmaceutically acceptable salts, pharmaceutically acceptable solvates and pharmaceutical compositions containing them.

Another objective of the present invention is to provide novel pyridylmethylsulfinyl benzimidazoles of the general formula (I), its derivatives, its analogs, its various isomers, its polymorphs, its pharmaceutically acceptable salts, its pharmaceutically acceptable solvates and pharmaceutical compositions containing them having a better safety profile and shorter $H^+/K^+$-ATPase enzyme inhibition time.

Yet another objective of the present invention is therefore, to provide a process for the preparation of novel pyridylmethylsulfinyl benzimidazoles of the general formula (I), its derivatives, its analogs, its tautomers, its various isomers, its polymorphs, its pharmaceutically acceptable salts, pharmaceutically acceptable solvates and pharmaceutical compositions containing them.

Still another objective of the present invention is to provide a novel intermediate of formula (IV)

where X and Y may be same or different and independently represent a hydrogen, halogen, optionally halogenated $(C_1-C_6)$alkoxy group, or optionally halogenated $(C_1-C_6)$ alkyl group; A represents a substituted or unsubstituted, 3 to 7 membered nitrogen containing heterocycle excluding substituted or unsubstituted pyrroles; A may further contain one or more heteroatoms selected from N, O, S or a group $NR^5$ where $R^5$ represents hydrogen, $(C_1-C_6)$alkyl, aralkyl, acyl, alkoxycarbonyl, aryloxycarbonyl, or aralkoxycarbonyl groups; the heterocycle A, is linked specifically through N-atom to the benzimidazole moiety; the group A may be saturated or may contain one or more double bonds.

DETAILED DESCRIPTION OF THE INVENTION

Pyridylmethylsulfinyl benzimidazoles of the present invention have the general formula (I)

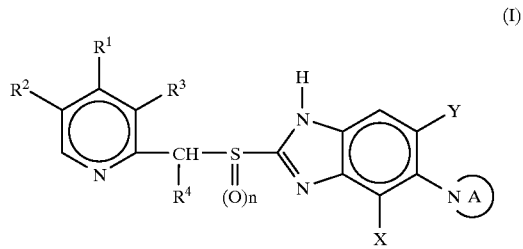

(I)

In the above formula (I),

X and Y may be same or different and independently represent a hydrogen, halogen, optionally halogenated $(C_1-C_6)$alkoxy group, or optionally halogenated $(C_1-C_6)$ alkyl group;

A represents a substituted or unsubstituted, 3 to 7 membered nitrogen containing heterocycle excluding substituted or unsubstituted pyrroles; A may further contain one or more heteroatoms selected from N, O, S or a group $NR^5$ where $R^5$ represents hydrogen, $(C_1-C_6)$alkyl, aralkyl, acyl, alkoxycarbonyl, aryloxycarbonyl, or aralkoxycarbonyl groups; the heterocycle A, is linked specifically through N-atom to the benzimidazole moiety; the group A may be saturated or may contain one or more double bonds; $R^4$ represents hydrogen, halogen or $(C_1-C_3)$alkyl group ; $R^2$ and $R^3$ may be same or different and independently represent hydrogen, halogen, nitro, cyano, optionally substituted groups selected from amino, $(C_1-C_6)$alkyl, $(C_1-C_6)$alkoxy, aryloxy or aralkoxy groups; $R^1$ represents hydrogen, halogen, substituted or unsubstituted groups selected from $(C_1-C_8)$alkyl, aryl, aralkyl, $(C_3-C_{10})$cycloalkyl, $(C_1-C_6)$ alkylthio, $(C_1-C_6)$alkenylthio, heterocyclyl, amino, $(C_1-C_8)$ alkylamino, dialkylamino, arylamino, diarylamino, alkylarylamino, $(C_1-C_6)$alkoxy, $(C_2-C_6)$acyloxy, $(C_3-C_{10})$ cycloalkyloxy, aralkoxy, aryloxy, alkoxyalkoxy, or a group $-O-(CH_2)_m-O-(CH_2)_p-R^6$ where m is an integer ranging from 1 to 10 and p is an integer ranging from 0 to 3 and $R^6$ is a linear or branched $(C_1-C_6)$alkyl, heterocyclyl, heteroaryl, aralkyl, hydroxy, alkoxy, aryloxy, aralkoxy, alkoxycarbonyl, alkoxyalkyl, or alkoxyalkoxy groups; and n is an integer ranging from 0 to 2.

Suitable heterocycles represented by A includes substituted or unsubstituted aziridinyl, azetidinyl, azepinyl, piperidinyl, pyrrolidinyl, pyrrolinyl, hexahydroazepinyl, 3-oxazepinyl, 4-oxazepinyl, 3-thiazepinyl, 4-thiazepinyl, 1,3-diazepinyl, 1,4-diazepinyl, piperazinyl, 1,3-diazolidinyl, morpholinyl, 4-thiomorpholinyl, oxazolidinyl, imidazolyl, triazolyl, pyrazolyl, 2-pyrazolinyl, 1,4-dihydropyridazinyl, 4-oxazolinyl, 4-thiazolinyl, 1,4-oxazinyl, tetrahydropyridinyl, and the like.

The heterocycle A may be substituted and suitable substituents on the heterocycle represented by A may be selected from the group comprising halogen, amino, hydroxy, cyano, oxo, formyl, hydroxylamino, hydroxylimino, $(C_1-C_6)$alkoxyamino, $(C_1-C_6)$alkoxyimino, $(C_1-C_6)$alkyl, $(C_3-C_{10})$cycloalkyl, hydroxy$(C_1-C_6)$alkyl, mercapto, thio $(C_1-C_6)$alkyl, $(C_1-C_6)$alkylthio, amino $(C_1-C_6)$alkyl, $(C_1-C_6)$alkylamino, dialkylamino, arylamino, $(C_1-C_6)$alkoxy, aryloxy, $(C_3-C_{10})$cycloalkyloxy, $(C_1-C_3)$ alkylenedioxy, aryl, heterocyclyl, N-alkylimino, alkoxyalkyl, acyl, acyloxy, alkoxycarbonyl, or aryloxycarbonyl groups. These substituents may further be substituted and are selected from the group consisting of $(C_1-C_3)$alkyl, aryl, $(C_1-C_3)$alkoxy, aryloxy, hydroxy, halogen, amino $(C_1-C_3)$alkyl, and hydroxy $(C_1-C_3)$alkyl groups.

Preferred substituents on the heterocycle A include halogen atom, hydroxy, $(C_1-C_6)$alkyl, $(C_1-C_6)$alkoxy, hydroxy $(C_1-C_6)$alkyl, amino, hydroxylamino, hydroxylimino, aryl, cyano, oxo, or $(C_1-C_3)$alkylenedioxy groups.

The groups $R^1$, $R^2$ and $R^3$ may be substituted and may be selected from halogen, $(C_1-C_3)$alkyl, aryl, aralkyl, $(C_1-C_3)$ alkoxy, hydroxy, amino, amino $(C_1-C_3)$alkyl, and hydroxy $(C_1-C_3)$alkyl groups.

The alkyl moiety defined in this specification with respect to alkyl, alkylamino, dialkylamino, alkylarylamino, alkylthio, alkylimino and the like may be linear or branched. Examples include methyl, ethyl, n-propyl, isopropyl, 1-methylpropyl, tert.-butyl, n-pentyl, 1-ethylpropyl, isoamyl, n-hexyl groups and the like.

The alkoxy group and alkoxy moiety of alkoxyalkyl, alkoxycarbonyl, alkoxyamino, alkoxyalkoxy group defined in this specification may be linear or branched and are derived from the above mentioned alkyl groups.

The halogen atom defined in this specification includes chlorine, bromine, fluorine and iodine.

Examples of acyl group may be acetyl, propionyl, butyryl, benzoyl and the like, which may be optionally halogenated.

Examples of acyloxy group are derived from the above mentioned acyl groups.

Examples of aryl group may be phenyl, naphthyl and the like, which may be optionally halogenated.

Examples of the group aralkyl and aralkyl moiety in aralkoxycarbonyl include benzyl, phenethyl, phenyl$(C_3-C_6)$ alkyl groups and the like which may be optionally halogenated.

Examples of the heteroaryls are: thienyl, pyrimidinyl, pyridyl, pyridazinyl, indolyl, pyrazinyl, benzoxazinyl and benzothiazinyl and the like. Examples of the heterocyclys are: azirindinyl, pyrrolidinyl, piperidinyl, morpholinyl, and thiomorpholinyl and the like.

Preferred groups represented by X and Y include hydrogen, halogen especially chlorine and fluorine, optionally halogenated $(C_1-C_6)$alkoxy, especially optionally fluorinated $(C_1-C_3)$alkoxy, optionally halogenated $(C_1-C_6)$ alkyl, especially optionally fluorinated $(C_1-C_3)$alkyl group.

Preferred group represented by $R^4$ is hydrogen atom.

Preferred groups represented by $R^2$ and $R^3$ include hydrogen, halogen, optionally halogenated $(C_1-C_3)$alkyl, especially halogen being fluorine, optionally halogenated $(C_1-C_3)$alkoxy groups, especially halogen being fluorine.

Preferred groups represented by $R^1$ include hydrogen, halogen, optionally halogenated $(C_1-C_6)$alkyl, optionally halogenated $(C_1-C_6)$alkoxy, amino, optionally halogenated alkylamino, optionally halogenated dialkylamino, heterocyclyl such as pyrrolidinyl, piperidinyl, piperazinyl, morpholinyl, azepinyl and the like, optionally halogenated alkoxyalkoxy or a group $—O—(CH_2)_m—O(CH_2)_p—R^6$ as defined above.

The use of term halogenated means that the group is substituted with one or more halogen atoms.

The use of term fluorinated means that the group is substituted with one or more fluorine atoms.

Pharmaceutically acceptable salts forming part of this invention include acid addition salts such as hydrochloride, hydrobromide, nitrate, phosphate, perchlorate, sulfate, acetate, maleate, tartrate, methanesulfonate, benzenesulfonate, tosylate, palmoate, succinate, salicylate, hydroxynaphthoate, ascorbate, glycerophosphate, ketoglutarate, pyruvate, benzoate, hydroxybenzoate, aminobenzoate, phenylacetate, salts of arginine, aspartic acid, glutamic acid tryptophan, methionine, and the like. Salts may also include alkali metal salts such as Li, Na, K and alkaline earth metal salts such as Ca or Mg salts.

Acid addition salts are not preferred when n represents one.

Pharmaceutically acceptable solvates may be hydrates, or comprising other solvents of crystallisation such as alcohols.

The compounds of the present invention may also be present as stereoisomers.

Particularly preferred compounds according to the present invention include compounds of formula (I) wherein X represents hydrogen or fluorine;

Y represents hydrogen or fluorine;

n represents an integer 1;

$R^2$ represents hydrogen, halogen, optionally alkylated amino, methyl, or methoxy group;

$R^3$ represents hydrogen, fluoro, methyl, or methoxy group;

$R^1$ represents hydrogen, methyl, methoxy, 3-methoxypropoxy, chloro, trifluoroethyl, heterocyclyl groups such as pyrrolidinyl, piperidinyl, morpholinyl, piperazinyl or azepinyl groups;

The N-linked heterocycle A represents optionally substituted imidazolyl, pyrrolidinyl, piperidinyl, hexahydroazepinyl, piperazinyl or morpholinyl groups.

Particularly useful compounds according to the present invention includes:

2-[[(4-Methoxy-3,5-dimethyl)pyridin-2-yl]methylthio]-6-fluoro-5-(imidazol-1-yl)-1H-benzimidazole;

2-[[3-Methyl-4-(2,2,2-trifluoroethoxy)pyridin-2-yl] methylthio]-6-fluoro-5-(imidazol-1-yl)-1H-benzimidazole;

2-[[(4-Methoxy-3-methyl)pyridin-2-ylmethylthio]-6-fluoro-5-(imidazol-1-yl)-1H-benzimidazole;

2-[[(4-(3-Methoxypropoxy)-3-methyl)pyridin-2-yl] methylthio]-6-fluoro-5-(imidazol-1-yl)-1H-benzimidazole;

2-[[(4-Methoxy)pyridin-2-yl]methylthio]-6-fluoro-5-(imidazol-1-yl)-1H-benzimidazole;

2-[[(4-Chloro-3-methyl)pyridin-2-yl]methylthio]-6-fluoro-5-(imidazol-1-yl)-1H-benzimidazole;

2-[[(4-Methoxy-3,5-dimethyl)pyridin-2-yl]methylthio]-6-fluoro-5-(morpholin-1-yl)-1H-benzimidazole;

2-[[3-Methyl-4-(2,2,2-trifluoroethoxy)pyridin-2-yl] methylthio]-6-fluoro-5-(morpholin-1-yl)-1H-benzimidazole;

2-[[(4-Methoxy-3-methyl)pyridin-2-yl]methylthio]-6-fluoro-5-(morpholin-1-yl)-1H-benzimidazole;
2-[[(4-(3-Methoxypropoxy)-3H-methyl)pyridin-2-yl]methylthio]-6-fluoro-5-(morpholin-1-yl)-1H-benzimidazole;
2-[[(4-Morpholin-1-yl)-3-methylpyridin-2-yl]methylthio]-6-fluoro-5-(morpholin-1-yl)-1H-benzimidazole;
2-[[(4-Piperidin-1-yl)-3-methylpyridin-2-yl]methylthio]-6-fluoro-5-(morpholin-1-yl)-1H-benzimidazole;
2-[[(4-Methylpiperazin-1-yl)-3-methylpyridin-2-yl]methylthio]-6-fluoro-5-(morpholin-1-yl)-1H-benzimidazole;
2-[[(3-Methyl)pyridin-2-yl]methylthio]-6-fluoro-5-(morpholin-1-yl)-1H-benzimidazole;
2-[[(4-Methoxy-3,5-dimethyl)pyridin-2-yl]methylthio]-6-fluoro-5-(piperidin-1-yl)-1H-benzimidazole;
2-[[3-Methyl-4-(2,2,2-trifluoroethoxy)pyridin-2-yl]methylthio]-6-fluoro-5-(piperidin-1-yl)-1H-benzimidazole;
2-[[(4-Methoxy-3-methyl)pyridin-2-yl]methylthio]-6-fluoro-5-(piperidin-1-yl)-1H-benzimidazole;
2-[[(4-Piperidin-1-y)-3-methylpyridin-2-yl]methylthio]-6-fluoro-5-(piperidin-1-yl)-1H-benzimidazole;
2-[[(4-Metroxy-3,5-dimethyl)pyridin-2-yl]methylthio]-6-fluoro-5-(4-methylpiperazin-1-yl)-1H-benzimidazole;
2-[[3-Methyl-4-(2,2,2-trifloethoxy)pyridin-2-yl]methylthio]-6-fluoro-5-(4-methylpiperazin-1yl)-1H-benzimidazole;
2-[[(4-Methoxy-3-methyl)pyridin-2-yl]methylthio]-6-fluoro-5-(4-methylpiperazin-1-yl)-1H-benzimidazole;
2-[[(3-Methyl)pyridin-2-yl]methylthio]-6-fluoro-5-(4-methylpiperazin-1-yl)-1H-benzimidazole;
2-[[(4-Methoxy-3,5-dimethyl)pyridin-2-yl]methylthio]-6-fluoro-5-(4-t-butyloxycarbonylpiperazin-1-yl)-1H-benzimidazole;
2-[[(4-Methoxy-3-methyl)pyridin-2-yl]methylthio]-6-fluoro-5-(4-t-butyloxycarbonylpiperazin-1-yl)-1H-benzimidazole;
2-[[(4-Methoxy-3-methyl)pyridin-2-yl]methylthio]-6-fluoro-5-(4-(ethylenedioxy)piperidin-1-yl)-1H-benzimidazole;
2-[[(4-Methoxy-3-methyl)pyridin-2-yl]methylthio]-6-fluoro-5-(4-piperidon-1-yl)-1H-benzimidazole);
2-[[(4-Methoxy-3-methyl)pyridin-2-yl]methylthio]-6-fluoro-5-(4-(hydroxyimino)piperidin-1-yl)-1H-benzimidazole;
2-[[(4-Methoxy-3-methyl)pyridin-2-yl]methylthio]-6-fluoro-5-[4-(hydroxy)piperidin-1-yl]-1H-benzimidazole;
2-[[(4-Methoxy-3-methyl)pyridin-2-yl]methylthio]-6-fluoro-5-(hexamethyleneimin-1-yl)-1H-benzimidazole;
2-[[(4-Morpholin-1-yl)-3-methylpyridin-2-yl]methylthio]-6-fluoro-5-(hexamethyleneimin-1-yl)-1H-benzimidazole;
2-[[(4-Methoxy-3-methyl)pyridin-2-yl]methylthio]-6-fluoro-5-(2-(methoxymethyl)pyrrolidin-1-yl)-1H-benzimidazole;
2-(4-Methoxy methyl)pyridin-2-yl]methylthio-6-fluoro-5-(pyrrolidin-1-yl)-1H-benzimidazole;
2-[[(4-Methoxy-3,5-dimethyl)pyridin-2-yl]methylthio]-5-(morpholin-1-yl)-1H-benzimidazole;
2-[[3-Methyl-4-(2,2,2-trifluoroethoxy)pyridin-2-yl]methylthio]-5-(morpholin-1-yl)-1H-benzimidazole;
2-[[(4-Methoxy-3-methyl)pyridin-2-yl]methylthio]-5-(morpholin-1-yl)-1H-benzimidazole;
2-[[(4-Methoxy-3,5-dimethyl)pyridin-2-yl]methylthio]-5-(4-methylpiperazin-1-yl)-1H-benzimidazole;
2-[[(4-Methoxy-3-methyl)pyridin-2-yl]methylthio]-5-(4-methylpiperazin-1-yl)-1H-benzimidazole;
2-[[(4-Methoxy-3-methyl)pyridin-2-yl]methylthio]-5-(4-t-butyloxycarbonylpiperazin-1-yl)-1H-benzimidazole;
2-[[(4-Methoxy-3-methyl)pyridin-2-yl]methylthio]-5-(piperidin-1-yl)-1H-benzimidazole;
2-[[(4-Methoxy-3-methyl)pyridin-2-yl]methylthio]-5-(hexamethyleneimin-1-yl)-1H-benzimidazole;
2-[[(4-Methoxy-3-methyl)pyridin-2-yl]methylthio]-4,6-difluoro-5-(morpholin-1-yl)-1H-benzimidazole;
2-[[(4-Methoxy-3,5-dimethyl)pyridin-2-yl]methylthio]-4,6-difluoro-5-(4-methylpiperazin-1-yl)-1H-benzimidazole;
2-[[(4-Methoxy-3,5-dimethyl)pyridin-2-yl]methylsulfinyl]-6-fluoro-5-(imidazol-1-yl)-1H-benzimidazole;
2-[[(4-Methoxy-3,5-dimethyl)pyridin-2-yl]methylsulfinyl]-6-fluoro-5-(imidazol-1-yl)-1H-benzimidazole, sodium salt;
2-[[(4-Methoxy-3,5-dimethyl)pyridin-2-yl]methylsulfonyl]-6-fluoro-5-(imidazol-1-yl)-1H-benzimidazole;
2-[[3-Methyl-4-(2,2,2-trifluoroethoxy)pyridin-2-yl]methylsulfinyl]-6-fluoro-5-(imidazol-1-yl)-1H-benzimidazole;
2-[[3-Methyl-4-(2,2,2-trifluoroethoxy)pyridin-2-yl]methylsulfinyl]-6-fluoro-5-(imidazol-1-yl)-1H-benzimidazole, sodium salt;
2-[[(4-Methoxy-3-methyl)pyridin-2-yl]methylsulfinyl]-6-fluoro-5-(imidazol-1-yl)-1H-benzimidazole;
2-[[(4-(3-Methoxypropoxy)-3-methyl)pyridin-2-yl]methylsulfinyl]-6-fluoro-5-(imidazol-1-yl)-1H-benzimidazole;
2-[[(4-Methoxy)pyridin-2-yl]methylsulfinyl]-6-fluoro-5-(imidazol-1-yl)-1H-benzimidazole;
2-[[(4-Methoxy)pyridin-2-yl]methylsulfinyl]-6-fluoro-5-(imidazol-1-yl)-1H-benzimidazole, sodium salt;
2-[[(4-Chloro-3-methyl)pyridin-2-yl]methylsulfinyl]-6-fluoro-5-(imidazol-1-yl)-1H-benzimidazole;
2-[[(4-Methoxy-3,5-dimethyl)pyridin-2-yl]methylsulfinyl]-6-fluoro-5-(morpholin-1-yl)-1H-benzimidazole;
2-[[(4-Methoxy-3,5-dimethyl)pyridin-2-yl]methylsulfinyl]-6-fluoro-5-(morpholin-1-yl)-1H-benzimidazole, sodium salt;
2-[[3-Methyl-4-(2,2,2-trifluoroethoxy)pyridin-2-yl]methylsulfinyl]-6-fluoro-5-(morpholin-1-yl)-1H-benzimidazole;
2-[[-Methyl-4-(2,2,2-trifluoroethoxy)pyridin-2-yl]methylsulfinyl]-6-fluoro-5-(morpholin-1-yl)-1H-benzimidazole, sodium salt;
2-[[(4-Methoxy-3-methyl)pyridin-2-yl]methylsulfinyl]-6-fluoro-5-(morpholin-1-yl)-1H-benzimidazole;
2-[[(4-Methoxy-3-methyl)pyridin-2-yl]methylsulfinyl]-6-fluoro-5-(morpholin-1-yl)-1H-benzimidazole, sodium salt;
2-[[(4-(3-Methoxypropoxy)-3-methyl)pyridin-2-yl]methylsulfinyl]-6-fluoro-5-(morpholin-1-yl)-1H-benzimidazole;
2-[[4-(Morpholin-1-yl)-3-methylpyridin-2-yl]methylsulfinyl]-6-fluoro-5-(morpholin-1-yl)-1H-benzimidazole;
2-[[4-(Morpholin-1-yl)-3-methylpyridin-2-yl]methylsulfinyl]-6-fluoro-5-(morpholin-1-yl)-1H-benzimidazole, sodium salt;
2-[[(4-Piperidin-1-yl)-3-methylpyridin-2-yl)methylsulfinyl]-6-fluoro-5-(morpholin-1-yl)-1H-benzimidazole;
2-[[(3-Methyl)pyridin-2-yl]methylsulfinyl]-6-fluoro-5-(morpholin-1-yl)-1H-benzimidazole;
2-[[(4-Methoxy-3,5-dimethyl)pyridin-2-yl]methylsulfinyl]-6-fluoro-5-(piperidin-1-yl)-1H-benzimidazole;
2-[[(4-Methoxy-3,5-dimethyl)pyridin-2-yl]methylsulfinyl]-6-fluoro-5-(piperidin-1-yl)-1H-benzimidazole, sodium salt;
2-[[3-Methyl-4-(2,2,2-trifluoroethoxy)pyridin-2-yl]methylsulfinyl]-6-fluoro-5-(piperidin-1-yl)-1H-benzimidazole;

2-[[(4-Methoxy-3-methyl)pyridin-2-yl]methylsulfinyl]-6-fluoro-5-(piperidin-1-yl)-1H-benzimidazole;
2-[[(4-Methoxy-3-methyl)pyridin-2-yl]methylsulfinyl]-6-fluoro-5-(piperidin-1-yl)-1H-benzimidazole, sodium salt;
2-[[(4-Piperidin-1-yl)-3-methyl)pyridin-2-yl]methylsulfinyl]-6-fluoro-5-(piperidin-1-yl)-1H-benzimidazole;
2-[[(4-Methoxy-3,5-dimethyl)pyridin-2-yl]methylsulfinyl]-6-fluoro-5-(4-methylpiperazin-1-yl)-1H-benzimidazole;
2-[[3-Methyl-4-(2,2,2-trifluoroethoxy)pyridin-2-yl]methylsulfinyl]-6-fluoro-5-(4-methylpiperazin-1-yl)-1H-benzimidazole;
2-[[(4-Methoxy-3,5-dimethyl)pyridin-2-yl]methylsulfinyl]-6-fluoro-5-(4-t-butyloxycarbonylpiperazin-1-yl)-1H-benzimidazole;
2-[[(4-Methoxy-3-methyl)pyridin-2-yl]methylsulfinyl]-6-fluoro-5-(4-t-butyloxycarbonylpiperazin-1-yl)-1H-benzimidazole;
2-[[(4-Methoxy-3-methyl)pyridin-2-yl]methylsulfinyl]-6-fluoro-5-(4-(ethylenedioxy)piperidin-1-yl)-1H-benzimidazole;
2-[[(4-Methoxy-3-methyl)pyridin-2-yl]methylsulfinyl]-6-fluoro-5-(4-(ethylenedioxy)piperidin-1-yl)-1H-benzimidazole, sodium salt;
2-[[(4-Methoxy-3-methyl)pyridin-2-yl]methylsulfinyl]-6-fluoro-5-(4-piperidon-1-yl)-1H-benzimidazole;
2-[[(4-Methoxy-3-methyl)pyridin-2-yl]methylsulfinyl]-6-fluoro-5-(4-piperidon-1-yl)-1H-benzimidazole, sodium salt;
2-[[(4-Methoxy-3-methyl)pyridin-2-yl]methylsulfinyl]-6-fluoro-5-(4-(hydroxyimino)piperidin-1-yl)-1H-benzimidazole;
2-[[(4-Methoxy-3-methyl)pyridin-2-yl]methylsulfinyl]-6-fluoro-5-(4-hydroxypiperidin-1-yl)-1H-benzimidazole;
2-[[(4-Methoxy-3-methyl)pyridin-2-yl]methylsulfinyl]-6-fluoro-5-(hexamethyleneimin-1-yl)-1H-benzimidazole;
2-[[(4-Methoxy-3-methyl)pyridin-2-yl]methylsulfinyl]-6-fluoro-5-(hexamethylenelmin-1-yl)-1H-benzimidazole, sodium salt;
2-[[(4-Morpholin-1-yl)-3-methyl)pyridin-2-yl]methylsulfinyl-6-fluoro-5-(hexamethyleneimin-1-yl)-1H-benzimidazole;
2-[[(4-Methoxy-3-methyl)pyridin-2-yl]methylsulfinyl]-6-fluoro-5-(2-methoxymethyl)pyrrolidin-1-yl)-1H-benzimidazole;
2-[[(4-Methoxy-3-methyl)pyridin-2-yl]methylsulfinyl]-6-fluoro-5-(pyrrolidin-1-yl)-1H-benzimidazole;
2-[[(4-Methoxy-3,5-dimethyl)pyridin-2-yl]methylsulfinyl]-5-(morpholin-1-yl)-1H-benzimidazole;
2-[[-Methyl-4-(2,2,2-trifluoroethoxy)pyridin-2-yl]methylsulfinyl]-5-(morpholin-1-yl)-1H-benzimidazole;
2-[[(4-Methoxy-3-methyl)pyridin-2-yl]methylsulfinyl]-5-(morpholin-1-yl)-1H-benzimidazole;
2-[[(4-Methoxy-3-methyl)pyridin-2-yl]methylsulfinyl]-5-(morpholin-1-yl)-1H-benzimidazole, sodium salt;
2-[[(4-Methoxy-3,5-dimethyl)pyridin-2-yl]methylsulfinyl]-5-(4-methylpiperazin-1-yl)-1H-benzimidazole;
2-[[(4-Methoxy-3-methyl)pyridin-2-yl]methylsulfinyl]-5-(4-t-butyloxycarbonylpiperazin-1-yl)-1H-benzimidazole;
2-[[(4-Methoxy-3-methyl)pyridin-2-yl]methylsulfinyl]-5-(hexamethyleneimin-1-yl)-1H-benzimidazole and
2-[[(4-Methoxy-3-methyl)pyridin-2-yl]methylsulfinyl]-4,6-difluoro-5-(morpholin-1-yl)-1H-benzimidazole.

The present invention provides a process for the preparation of novel antiulcer compounds especially pyridylmethylsulfinyl benzimidazole derivatives of the general formula (I) which comprises:

a) reacting a compound of general formula (III) wherein $R^1$, $R^2$, $R^3$, $R^4$ are as defined earlier in general formula (I) and L is a leaving group such as Cl, Br, I, p-toluenesulfonate, methanesulfonate, trifluoromethanesulfonate and the like with a compound of general formula (IV) where X, Y and A are as defined in general formula (I),

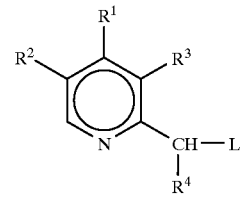

(III)

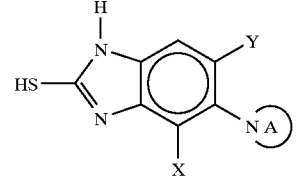

(IV)

in a suitable organic solvent in the presence of an appropriate base to give a compound of general formula (V),

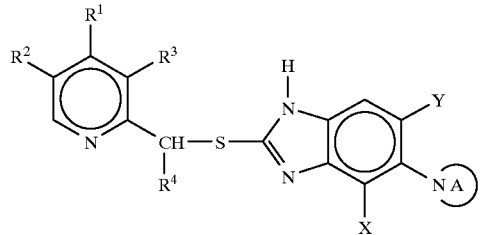

(V)

The compound of general formula (V) represents a compound of general formula (I) where n represents zero.

b) oxidizing the compound of general formula (V) with a suitable oxidizing agent to obtain a compound of general formula (I). The compound of general formula (I) can be either a sulfoxide (n=1) or a sulfone (n=2) depending on the nature and amount of oxidizing agent used.

The reaction of compound of general formula (III) with a compound of general formula (IV) to produce a compound of general formula (V) may be carried out in the presence of organic solvents such as methanol, ethanol, acetonitrile, tetrahydrofuran, dioxane, dimethyl formamide, dimethylsulfoxide or organic solvents mixed with water. The above reaction may be preferably carried out in the presence of a suitable base. The bases used include, alkali metal hydroxides such as NaOH and KOH, alkali metal carbonates such as $K_2CO_3$, $Na_2CO_3$, alkaline earth metal carbonate such as $CaCO_3$, alkali metal bicarbonates such as $NaHCO_3$ and the like, alkali metal hydrides such as NaH, KH. Organic bases such as triethylamine, ethyldiisopropyl amine and the like may also be used. Mixture of solvents and/or mixture of bases may be used. The reaction temperature may range from 0° C. to 150° C. preferably 30° C. to 100° C. The duration of the reaction may range from 1 to 24 h, preferably from 2 to 12 h.

The oxidation of compound of general formula (V) to compound of general formula (I) may be carried out using oxidizing agents generally used for this reaction and is not critical and include m-chloroperoxybenzoic acid, hydrogen peroxide, peroxyacetic acid, trifluoroperoxyacetic acid, vanadium pentoxide, sodium metaperiodate, peroxymaleic acid, monoperoxyphthalic acid, nitric acid, dinitrogen tetroxide, catalytic $OsO_4$ in the presence of excess of oxidizing agent, iodoxobenzene, chlorobenzotriazole, N-halosuccinimide, t-butylhypochlorite, sodium hypochlorite, $MnO_2$, $CrO_3$, ceric ammonium nitrate and the like. The reaction may be carried out either in organic solvent or in aqueous organic medium. Solvents used in the oxidation may be chlorinated hydrocarbons such as dichloromethane, chloroform, aromatic hydrocarbons such as benzene, toluene and the like, or lower alcohols such as methanol, ethanol and the like. The oxidation reaction may be carried out at a temperature in the range of −78° C. to 100° C. preferably from 30° C. to −70° C. The duration of the reaction may range from 5 min to 4 h preferably from 5 min to 2 h.

In another embodiment of the present invention, the compound of general formula (I) can also be prepared by reacting a compound of general formula (VI) where $R^1$, $R^2$, $R^3$ and $R^4$ are as defined earlier with a compound of general formula (VII) where X, Y and A are as defined earlier,

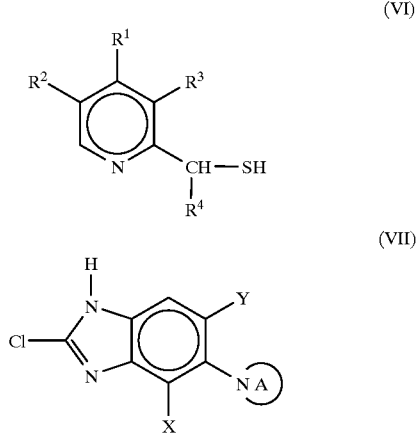

to yield a compound of general formula (V) as defined earlier which is further oxidized as described above.

The reaction of compound of general formula (VI) with a compound of general formula (VII) to produce a compound of general formula (V) may be carried out in the presence of organic solvents such as methanol, ethanol, acetonitrile, tetrahydrofuran, dioxane, dimethyl formamide, dimethylsulfoxide or organic solvents mixed with water. The above reaction may be preferably carried out in the presence of a suitable base. The bases used include, alkali metal hydroxides such as NaOH and KOH, alkali metal carbonates such as $K_2CO_3$, $Na_2CO_3$, alkaline earth metal carbonates such as $CaCO_3$, alkali metal bicarbonates such as $NaHCO_3$ and the like, alkali metal hydrides such as NaH, KH. Organic bases such as triethylamine, ethyldiisopropyl amine and the like may also be used. Mixture of solvents and/or mixture of bases may be used. The reaction temperature may range from 0° C. to 150° C. preferably 30° C. to 100° C. The duration of the reaction may range from 1 to 24 h, preferably from 2 to 12 h.

In yet another embodiment of the present invention, the compound of general formula (I) can also be prepared by reaction of a compound of general formula (VIII) where $R^1$, $R^2$, $R^3$ and $R^4$ are as defined earlier, with a compound of general formula (IX) where X, Y and A are as defined earlier, followed by oxidation of the resulting compound (V) as described earlier,

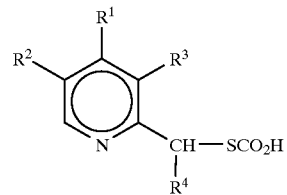

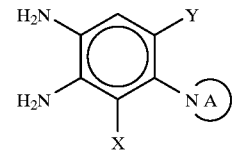

The reaction of compound of general formula (VIII) with a compound of general formula (IX) may be carried out in polar solvents such as HMPA, acetonitrile, water, acetic acid and the like in the presence of strong acids such as conc. HCl. Temperature in the range of 50° C. to 180° C. may be used.

Alternatively, the compound of formula (I) can also be prepared by reacting a compound of general formula (X) where $R^1$, $R^2$, $R^3$ are as defined earlier and Z represents a leaving group such as halogen, especially chlorine and bromine or a thioalkyl group, with a compound of general formula (XI) where X, Y, n, $R^4$ and A are as defined earlier, $R^7$ represents hydrogen or a nitrogen protecting group such as benzyl, acyl, alkoxycarbonyl, aryloxycarbonyl and the like, and M represents an alkali metal such as Li, Na, K and the like.

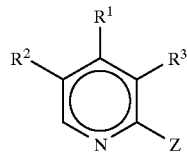

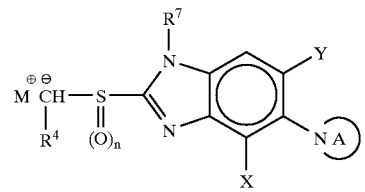

The protecting group is removed after the reaction.

The reaction of compound of general formula (X) with a compound of general formula (XI) may be carried out in an inert solvent such as ether, THF, DMSO, DMF and the like. Temperature in the range 0° C. to 150° C. may be used. The duration of the reaction may be 1–24 h especially 2–12 h.

The compound of the general formula (III) can be prepared by known methods (J. Med. Chem. 1992, 35, 1049–57) by using appropriately substituted pyridines.

The novel intermediate of the general formula (IV)

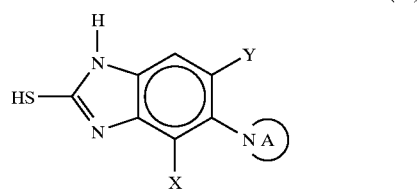
(IV)

where X and Y may be same or different and independently represent a hydrogen, halogen, optionally halogenated ($C_1$–$C_6$)alkoxy group, or optionally halogenated($C_1$–$C_6$) alkyl group;

A represents a substituted or unsubstituted, 3 to 7 membered nitrogen containing heterocycle excluding substituted or unsubstituted pyrroles; A may further contain one or more heteroatoms selected from N, O, S or a group $NR^5$ where $R^5$ represents hydrogen, ($C_1$–$C_6$)alkyl, aralkyl, acyl, alkoxycarbonyl, aryloxycarbonyl, or aralkoxycarbonyl groups; the heterocycle A, is linked specifically through N-atom to the benzimidazole moiety; the group A may be saturated or may contain one or more double bonds, used in the preparation of compound of general formula (I) in the processes described above may be prepared utilizing types of reactions known to one skilled in the art.

heterocycle of formula (XV), such as morpholine, piperidine, pyrrolidine, hexahydroazepine, 4-methylpiperazine, imidazole and the like mentioned earlier. The reaction may be carried out in the presence of a base such as alkalis like sodium hydroxide, potassium hydroxide, alkali metal carbonates like sodium carbonate, potassium carbonate and the like in solvents such as DMSO, DMF, DME and the like. The reagent may be used in 1 to 10 equivalents, preferably 3 to 5 equivalents. The reaction temperature may range from 0° C. to 150° C., preferably from 30° C. to 120° C. The reaction may be conducted for 1 to 24 h, preferably 6 to 12 h.

The compound of formula (XVI) may be converted to compound of formula (XVII) by using conventional hydrolysis under basic conditions using alkalis such as sodium hydroxide, potassium hydroxide and the like in presence of solvents such as alcohols like methanol, ethanol and the like. The reagent may be used in 1 to 10 equivalents, preferably 3 to 5 equivalents. The reaction temperature may range from −10° C. to 50° C., preferably from 0° C. to 30° C. and the duration of the reaction may range from 1 to 24 h, preferably 6 to 10 h. The base and solvent used for the reaction is not critical.

The compound of the formula (XVII) may be converted to a compound of formula (IX) under conventional reduction conditions. The reduction may be carried out in the presence of gaseous hydrogen and a catalyst such as Pd/C, Rh/C, Pt/C or using $SnCl_2$/HCl or iron/HCl. The reaction may also be

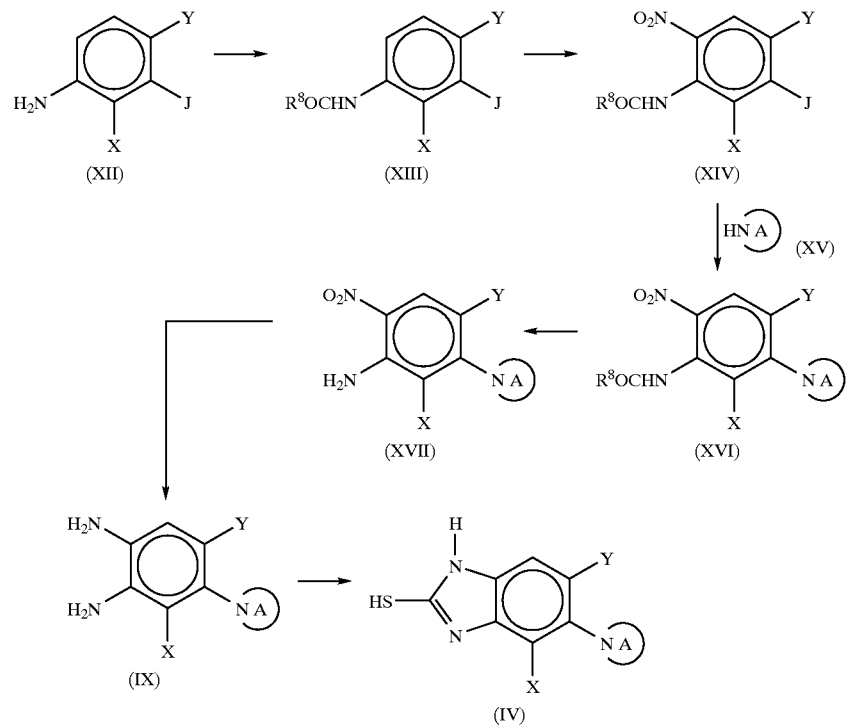

The compound of general formula (XII) where X and Y are as defined earlier, and J represents F or Cl atom may be converted to a compound of formula (XIV) where X, Y and J are as defined earlier and $R^8$ represents a lower alkyl group, by using known methods (Chem. Pharm. Bull., 37, 1517 (1989); U.S. Pat. No. 4,758,579)

The compound of formula (XIV) may be converted to a compound of formula (XVI) using a nitrogen containing conducted in the presence of solvents such as methanol, ethanol, ethyl acetate, dioxane and the like. The catalyst may be 5–10% of metal on carbon, the amount of catalyst may range from 10–20% w/w and the reaction may be carried out at atmospheric pressure.

The compound of formula (IX) may be converted to compound of formula (IV) by using potassium ethyl xanthate or carbon disulfide in the presence of an alkali such as sodium hydroxide or potassium hydroxide. The reaction may be conducted in the presence of solvents such as methanol or ethanol and the temperature may range from 0° C. to 150° C. preferably at 30° C. to 80° C. The duration of the reaction may range from 0.5 to 12 h, preferably 2 to 6 h.

The pharmaceutically acceptable salts are prepared by reacting the compound of formula (I) with 1 to 4 equivalents of a base such as sodium hydroxide, sodium methoxide, sodium hydride, potassium hydroxide, lithium hydroxide, potassium t-butoxide, calcium hydroxide, magnesium hydroxide and the like, in solvents like ether, acetone, THF, methanol, t-butanol, dioxane, isopropanol, ethanol etc. Mixture of solvents may be used. Organic bases like lysine, arginine, tryptophan, methionine, diethanolamine, choline, guanidine and their derivatives etc. may also be used. Alternatively, acid addition salts are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic, acid, hydroxynaphthoic acid, ascorbic acid, palmitic acid, succinic acid, benzoic acid, benzene sulfonic acid, tartaric acid, aminobenzoic acid, hydroxybenzoic acid, pyruvic acid, phenylacetic acid, and the like in solvents like ethyl acetate, ether, alcohols, acetone, THF, dioxane etc. Mixture of solvents may also be used.

The compound of formula (I) where n=1 is a chiral compound. Therefore, the present invention also relates to both the enantiomers, their mixtures or racemic mixture. The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid and the like or chiral bases such as brucine, cinchona alkaloids and their derivatives and the like.

The single enantiomers can also be obtained by the optical purification of the enantiomerically enriched mixture in which the racemate can be selectively precipitated from a suitable solvent. Preferable solvents for crystallization may be a ketone such as acetone or 2-butanone or an ester such as ethyl acetate, or an alcohol such as ethanol or a nitrile such as acetonitrile, or a hydrocarbon such as toluene or a mixture of organic solvents which may additionally comprise water.

Various polymorphs of compound of general formula (I) forming part of this invention may be prepared by crystallization of compound of formula (I) under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or slow cooling. The presence of polymorphs may be determined by solid probe NMR spectroscopy, IR spectroscopy, differential scanning calorimetry, powder X-ray diffraction or such other techniques.

The present invention also provides a pharmaceutical composition, containing the compounds of the general formula (I), as defined above, their derivatives, their analogs, their tautomeric forms, their stereoisomers, their polymorphs, their pharmaceutically acceptable salts, their pharmaceutically acceptable solvates in combination with the usual pharmaceutically employed carriers, diluents and the like, useful for prophylaxis and/or treatment of gastric and duodenal ulcers, as cytoprotective agents for gastrointestinal tract and as antibacterial agents more specifically as bactericides for Helicobacter pylori.

The pharmaceutical composition may be in the forms normally employed such as for oral use, tablets, capsules, powders, syrups, solutions, suspensions, sustained release formulations, enteric-coated capsules or for paranteral use, injections. These are normally prepared by using pharmaceutically acceptable additives, carriers, diluents, sterile media and the like by using methods well known to those skilled in the art.

The compound of the formula (I) as defined above are clinically administered to mammals, including man, via either oral or parenteral routes. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 1 mg to about 1000 mg (70 kg body weight) per day administered singly or as a divided dose. However, the optimum dosage for the individual subject being treated will be determined by the person responsible for treatment, generally smaller doses being administered initially and thereafter increments made to determine the most suitable dosage.

The dose may remarkably vary depending upon the patient, age and the kind of ulcers.

Suitable pharmaceutically acceptable carriers include solid fillers or diluents and sterile aqueous or organic solutions. The active compound will be present in such pharmaceutical compositions in the amounts sufficient to provide the desired dosage in the range as described above. Thus, for oral administration, the compounds can be combined with a suitable solid or liquid carrier or diluent to form capsules, tablets, powders, syrups, solutions, suspensions and the like. The pharmaceutical compositions, may, if desired, contain additional components such as flavourants, sweeteners, excipients and the like. For parenteral administration, the compounds can be combined with sterile aqueous or organic media to form injectable solutions or suspensions. For example, the injection can be prepared by mixing the active ingredient with pH adjusting buffers, stabilizers, solubilizing agent or the like.

The invention is explained in detail in the examples given below which are provided by way of illustration only and therefore should not be construed to limit the scope of the invention.

Preparation 1

6-Fluoro-5-(imidazol-1-yl)-2-mercapto-1H-benzimidazole:

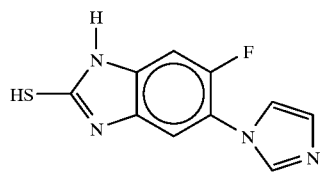

Step 1

Acetic anhydride (30 mL) was added at room temperature dropwise to 3-chloro-4-fluoroaniline (13.0 g, 0.1 mol) and stirred for 3 h. The reaction mixture was poured on ice (300 g) and the solid was filtered and dried to afford N-(3-chloro-4-fluorophenyl)acetamide (18.4 g, 98%) as a white solid. mp 96–97° C.; IR (KBr) 3303, 1671 cm$^{-1}$; $^1$H NMR (CDCl$_3$) δ 2.20 (s, 3H, CH$_3$), 7.05 (t, J=8.9 Hz, 1H), 7.28 (m,1H), 7.66 (d, J=4.6 Hz, 1H), 8.05 (s, 1H, NH); Mass (m/z) 187 (M$^+$).

Step 2

The compound (18.0 g, 0.1 mol) (obtained in step 1 above) was dissolved in dichloromethane (100 mL) and was added to a mixture of conc. HNO$_3$ (12 mL) and conc. H$_2$SO$_4$ (15 mL) (3 eq) dropwise at 0° C. and stirred for 10 h. The dichloromethane was removed under reduced pressure and the reaction mixture was poured on ice (300 g). The solid was filtered and dried to yield N-(2-nitro-4-fluoro-5-chlorophenyl)acetamide (18.5 g, 80%) as a yellow solid. mp 109–110° C.; IR (KBr) 3380, 1703, 1586 cm$^{-1}$; $^1$H NMR (CDCl$_3$) δ 2.30 (s, 3H, CH$_3$), 8.00 (d, J=6.6 Hz, 1H), 9.00 (d, J=6.8 Hz, 1H), 10.30 (s, 1H, NH); Mass (m/z) 232 (M+).

Step 3

The acetamide (18.5 g, 0.08 mol) (obtained in step 2 above) was dissolved in dimethyl sulfoxide (50 mL) and added to a well stirred mixture of imidazole (27.0 g, 0.4 mol), KOH (7.0 g, 0.12 mol) and dimethyl sulfoxide (50 mL). The mixture was stirred at 80° C. for 12 h and poured on ice (400 g). The resultant solid was filtered and dried to yield 2-nitro-4-fluoro-5-(imidazol-1-yl)aniline (12.5 g, 70%) as a brown solid. mp 122–123° C.; IR (KBr) 3473, 1528 cm$^{-1}$; $^1$H NMR (DMSO-d$_6$) δ 7.18 (d, J=5.8 Hz, 1H), 7.22 (d, J=6.9 Hz, 1H), 7.45 (brs, 2H, NH$_2$), 7.60 (s, 1H), 8.06 (m, 2H); Mass (m/z) 222 (M$^+$).

Step 4

The nitroaniline derivative (12.5 g, 0.056 mol) (obtained in step 3 above) was hydrogenated in ethanol (50 mL) over 10% Pd-C (1.0 g) in an atmosphere of hydrogen at ca 25° C. The catalyst was filtered through a celite bed and concentrated to afford 4-fluoro-5-(imidazol-1-yl)-1,2-phenylenediamine (7.0 g, 64%) as a brown viscous oil. IR (Neat) 3351 cm$^{-1}$; $^1$H NMR (DMSO-d$_6$) δ 5.00 (brs, 4H, 2×NH$_2$), 6.50 (d, J=9.6 Hz, 1H), 6.60 (d, J=6.3 Hz 1H), 7.08 (s, 1H), 7.32 (s, 1H), 7.80 (s, 1H); Mass (m/z) 192 (M$^+$.).

Step 5

The diamine (6.7 g, 0.035 mol) (obtained in step 4 above) was dissolved in ethanol (20 mL) and added to a stirred mixture of carbon disulfide (3.0 g, 0.04 mol), potassium hydroxide (2.3 g, 0.04 mol), water (5 mL) and ethanol (15 mL). The resultant solution was refluxed for 6 h. Animal charcoal (2.0 g) was added and further refluxed for 1 h. The mixture was filtered and washed with hot water. A mixture of acetic acid and water (1:2, 15 mL) was added to the filtrate slowly with vigorous stirring to separate 6-fluoro-5-(imidazol-1-yl)-2-mercapto-1H-benzimidazole (5.0 g, 60%) as a brown solid. mp 280° C. (decomp.); IR (KBr) 3078, 1481 cm$^{-1}$; $^1$H NMR (DMSO-d$_6$) δ 2.20 (s, 1H, SH), 7.10 (s, 1H), 7.24 (d, J=6.0 Hz, 1H), 7.26 (d, J=4.1 Hz, 1H), 7.56 (s, 1H), 8.00 (s, 1H), 12.90 (brs, 1H, NH); Mass (m/z) 234 (M$^+$.).

Preparation 2

6-Fluoro-5-(morpholin-1-yl)-2-mercapto-1H-benzimidazole:

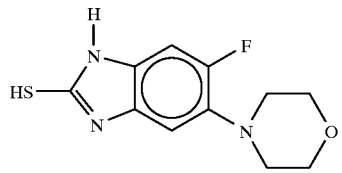

Step 1

2-Nitro-4-fluoro-5-(morpholin-1-yl)aniline (14.5 g, 70%) was prepared by an analogous procedure as described in preparation 1 (step 3) using N-(2-nitro-4-fluoro-5-chlorophenyl)acetamide (20.0 g, 0.086 mol), (obtained in preparation 1, step 2), morpholine (37.0 g, 0.43 mol), potassium hydroxide (5.8 g, 0.1 mol) and dimethyl sulfoxide (100 mL). mp 141–142° C.; IR (KBr) 3446, 1254 cm$^{-1}$; $^1$H NMR (CDCl$_3$) δ 3.20 (t, J=4.2 Hz, 4H, N(CH$_2$)$_2$), 3.90 (t, J=4.4 Hz, 4H, O(CH$_2$)$_2$), 6.00 (d, J=5.8 Hz, 1H), 6.10 (brs, 2H, NH$_2$), 7.80 (d, J=10.4 Hz, 1H); Mass (m/z) 241 (M$^+$).

Step 2

The nitroaniline derivative (14.0 g, 0.058 mol) (obtained in step 1 above) was hydrogenated using 10% Pd-C (3.0 g) in ethanol (75 mL) (as described in preparation 1, step 4) to yield 4-fluoro-5-(morpholin-1-yl)-1,2-phenylenediamine (11.0 g, 90%) as a brown viscous oil. IR (Neat) 3347 cm$^{-1}$; $^1$H NMR (DMSO-d$_6$) δ 3.12 (m, 4H, N(CH$_2$)$_2$), 3.80 (m, 4H, O(CH$_2$)$_2$), 4.80 (brs, 4H, 2×NH$_2$), 6.28 (d, J=5.9 Hz, 1H), 6.36 (d, J=9.8 Hz, 1H); Mass (m/z) 211 (M$^+$.).

Step 3

6-Fluoro-5-(morpholin-1-yl)-2-mercapto-1H-benzimidazole (10.0 g, 76%) was prepared by the procedure described in preparation 1 (step 5) using the diamine (11.0 g, 0.052 mol) (obtained in step 2 above), carbon disulfide (4.75 g, 0.062 mol), potassium hydroxide (3.5 g, 0.062 mol), ethanol (60 mL) and water (10 mL). mp 289° C. (decomp.); IR (KBr) 3124, 1485 cm$^{-1}$; $^1$H NMR (DMSO-d$_6$+CDCl$_3$) δ 2.28 (s, 1H, SH), 3.02 (m, 4H, N(CH$_2$)$_2$), 3.90 (m, 4H, O(CH$_2$)$_2$), 6.90 (d, J=5.6 Hz, 1H), 7.00 (d, J=10.2 Hz, 1H), 12.38 (brs, 1H, NH); Mass (m/z) 253 (M$^+$.).

Preparation 3

6-Fluoro-5-(piperidin-1-yl)-2-mercapto-1H-benzimidazole:

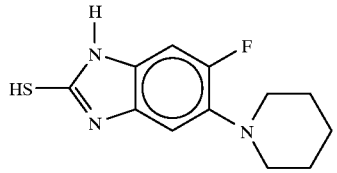

Step 1

2-Nitro-4-fluoro-5-(piperidin-1-yl)aniline (13.0 g, 52%) was prepared by an analogous procedure as described in preparation 1 (step 3) using N-(2-nitro-4-fluoro-5-chloro phenyl)acetamide (25.0 g, 0.107 mol) (obtained in preparation 1, step 2), piperidine (45.8 a, 0.537 mol), potassium hydroxide (9.0 g, 0.16 mol) and dimethyl sulfoxide (100 mL). mp 112–113° C. IR (KBr) 3472, 1234 cm$^{-1}$; $^1$H NMR (CDCl$_3$) δ 1.60 (m, 2H, CH$_2$), 1.70 (m, 4H, (CH$_2$)$_2$), 3.22 (m, 4H, N(CH$_2$)$_2$), 5.88 (d, J=7.6 Hz, 1H), 6.08 (brs, 2H, NH$_2$), 7.78 (d, J=14.2 Hz, 1H) ; Mass (m/z) 239 (M$^+$.).

Step 2

The nitroaniline derivative (6.2 g, 0.026 mol) (obtained in step 1 above) was hydrogenated using 10% Pd-C (1.0 g,) in ethanol (30 mL), using an analogous procedure as described in preparation 1 (step 4) to yield 4-fluoro-5-(piperidin-1-yl)-1,2-phenylenediamine (5.3 g 98%) as brown viscous oil. IR (Neat) 3346 cm$^{-1}$; $^1$H NMR (CDCl$_3$) δ 1.54 (m, 2H, CH$_2$), 1.70 (m, 4H, (CH$_2$)$_2$), 2.90 (m, 4H, N(CH$_2$)$_2$), 3.10 (brs, 4H, 2×NH$_2$), 6.40 (d, J=8.8 Hz, 1H), 6.48 (d, J=13.8 Hz, 1H); Mass (m/z) 209 (M$^+$.).

Step 3

6-fluoro-5-(tiperidin-1-yl)-2-mercapto-1H-benzimidazole (3.6 g, 64%) was prepared by a similar procedure as described in preparation 1 (step 5) using the diamine (4.5 g, 0.022 mol) (obtained in step 2 above), carbon disulfide (2.2 g, 0.029 mol), potassium hydroxide (1.6 g, 0.029 mol), ethanol (25 mL) and water (5 mL). mp 275° C. (decomp.); IR(KBr) 3122, 1486 cm$^{-1}$; $^1$H NMR (CD$_3$OD) δ 1.58 (m, 2H, CH$_2$), 1.76 (m, 4H, (CH$_2$)$_2$), 2.98 (t, J=5.6 Hz, 4H, N(CH$_2$)$_2$), 6.90 (d, J=7.4 Hz, 1H), 7.00 (d, J=11.6 Hz, 1H); Mass (m/z) 251 (M$^+$.)

Preparation 4

6-Fluoro-5-(4-methylpiperazin-1-yl)-2-mercapto-1H-benzimidazole:

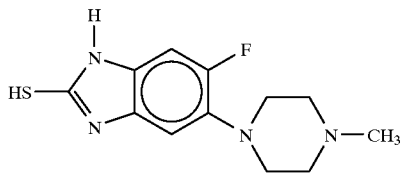

Step 1

N-[2-Nitro-4-fluoro-5-(methylpiperazin-1-yl)phenyl] acetamide (25.0 g, 80%) was prepared by an analogous procedure as described in preparation 1 (step 3) using N-(2-nitro-4-fluoro-5-chlorophenyl)acetamide (25.0 g, 0.107 mol) (obtained in preparation 1, step 2), 4-methylpiperazine (53.5 g, 0.535 mol), potassium hydroxide (9.05 g, 0.16 mol) and dimethyl sulfoxide (100 mL). mp 90–91° C.; IR (KBr) 3339, 1707, 1582 cm$^{-1}$; $^1$H NMR (CDCl$_3$) δ 2.24 (s, 3H, CH$_3$), 2.32 (s, 3H, CH$_3$), 2.56 (t, J=5.0 Hz, 4H, N(CH$_2$)$_2$), 3.42 (t, J=5.0 Hz, 4H, N(CH$_2$)$_2$), 7.90 (d, J=14.1 Hz, 1H), 8.36 (d, J=8.4 Hz, 1H), 10.70 (brs, 1H, NH); Mass (m/z) 296 (M$^+$.).

Step 2

The acetamide (25.0 g, 0.085 mol) (obtained in step 1 above) was dissolved in methanol (160 mL) and 6 M NaOH solution (42 nL) was added dropwise at ca 30° C. and stirred for 6 h. The mixture was cooled in an ice bath and water (300 mL) was added dropwise. The resultant precipitate was collected by filtration and dried to yield 2-nitro-4-fluoro-5-(4-methylpiperazin-1-yl)aniline (16.0 g, 75%) as a brown solid. mp 154–155° C.; IR (KBr) 3383, 1247 cm$^{-1}$; $^1$H NMR (CDCl$_3$) δ 2.32 (s, 3H, CH$_3$), 2.54 (t, J=5.0 Hz, 4H, N(CH$_2$)$_2$), 3.24 (t, J=4.6 Hz, 4H, N(CH$_2$)$_2$, 6.02 (d, J=7.5 Hz, 1H), 6.12 (brs, 2H, NH$_2$), 7.74 (d, J=14.0 Hz, 1H); Mass (m/z) 254 (M$^+$.).

Step 3

The nitroaniline derivative (16.0 g, 0.063 mol) (obtained in step 2 above) was hydrogenated using 10% Pd-C (2.5 g) in ethanol (60 mL) by an analogous procedure as described in preparation 1 (step 4) to yield 4-fluoro-5-(4-methylpiperazin-1-yl)-1,2-phenylenediamine (13.2 g, 94%) as a brown viscous oil. IR (Neat) 3332 cm$^{-1}$; $^1$H NMR (DMSO-d$_6$) δ 2.34 (s, 3H, CH$_3$), 2.62 (t, J=4.2 Hz, 4H, N(CH$_2$)$_2$), 3.08 (t, J=4.4 Hz, 4H, N(CH$_2$)$_2$), 3.30 (brs, 4H, 2×NH$_2$), 6.40 (d, J=8.2 Hz, 1H), 6.48 (d, J=12.8 Hz, 1H); Mass (m/z) 224 (M$^+$.).

Step 4

6-Fluoro-5-(4-methylpiperazin-1-yl)-2-mercapto-1H-benzimidazole (15.0 g, 94%) was prepared by a similar procedure to that described in preparation 1 (step 5) using the diamine (14.0 g, 0.06 mol) (obtained in step 3 above), carbon disulfide (6.1 g, 0.08 mol), potassium hydroxide (4.49 g, 0.08 mol), ethanol (70 mL) and water (10 mL). mp 290° C. (decomp.); IR (KBr) 3088, 1481 cm$^{-1}$; $^1$H NMR (DMSO-d$_6$) δ 2.24 (s, 3H, CH$_3$), 2.50 (t, J=4.3 Hz, 4H, N(CH$_2$)$_2$), 3.00 (t, J=4.4 Hz, 4H, N(CH$_2$)$_2$), 6.78 (d, J=7.3 Hz, 1H), 7.00 (d, J=11.9 Hz, 1H); Mass (m/z) 266 (M$^+$.).

Preparation 5

6-Fluoro-5-(4-t-butyloxycarbonylpiperazin-1-yl)-2-mercapto-1H-benzimidazole:

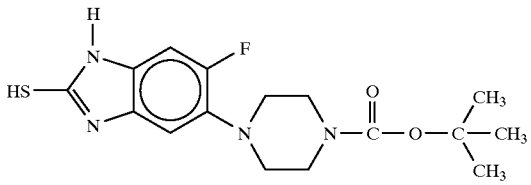

Step 1

2-Nitro-4-fluoro-5-(piperazin-1-yl)aniline (5.6 g, 77%) was prepared by a procedure analogous to that described in preparation 1 (step 3) using N-(2-nitro-4-fluoro-5-chlorophenyl)acetamide (7.4 g, 0.03 mol) (obtained in preparation 1, step 2), piperazine (27.2 g, 0.3 mol), potassium hydroxide (2.5 g, 0.045 mol) and dimethyl sulfoxide (30 mL). mp 120–121° C.; IR (KBr) 3334, 1504, 1251 cm$^{-1}$; $^1$H NMR (CDCl$_3$+CD$_3$OD) δ 3.00 (t, J=5.4 Hz, 4H, N(CH$_2$)$_2$); 3.20 (t, J=5.6 Hz, 4H, N(CH$_2$)$_2$), 3.82 (brs, 3H, NH), 6.18 (d, J=8.2 Hz, 1H), 7.74 (d, J=13.8 Hz, 1H); Mass (m/z) 240 (M$^+$.).

Step 2

The nitroaniline derivative (5.6 g, 0.023 mol) (obtained in step 1 above) was hydrogenated using 10% Pd-C (1.0 g) in ethanol (25 mL), using a procedure analogous to that described in preparation 1 (step 4) to yield 4-fluoro-5-(piperazin-1-yl)-1,2-phenylenediamine (4.7 g, 98%) as a brown viscous oil. IR (Neat) 3283 cm$^{-1}$; $^1$H NMR (CDCl$_3$) δ 2.80 (brs, 5H, NH), 2.94 (m, 4H, N(CH$_2$)$_2$), 3.06 (m, 4H, N(CH$_2$)$_2$), 6.42 (d, J=7.8 Hz, 1H), 6.47 (d, J=12.4 Hz, 1H); Mass (m/z) 210 (M$^+$.).

Step 3

6-Fluoro-5-(piperazin-1-yl)-2-mercapto-1H-benzimidazole (4.3 g, 80%) was prepared by an analogous procedure as described in preparation 1 (step 5) using the diamine (4.5 g, 0.021 mol) (obtained in step 2 above), carbon disulfide (1.9 g, 0.025 mol), potassium hydroxide (1.4 g, 0.025 mol), ethanol (25 mL) and water (5 mL). mp 100-10 1 ° C.; IR (KBr) 3133, 1482 cm$^{-1}$; $^1$H NMR (DMSO-d$_6$) δ 2.25 (s, 1H, SH), 2.90 (m, 4H, N(CH$_2$)$_2$), 4.10 (brs, 1H, NH), 4.48 (m, 4H, N(CH$_2$)$_2$), 6.80 (d, J=8.4 Hz, 1H), 7.00 (d, J=12.3 Hz, 1H), 12.30 (brs, 1H, NH); Mass (m/z) 252 (M$^+$.).

Step 4

A mixture of 6-fluoro-5-(piperazin-1-yl)-2-mercapto-1H-benzimidazole (4.3 g, 0.017 mol) (obtained in step 3 above), di-t-butyldicarbonate (4.4 g, 0.02 mol), 1N NaOH solution (20 mL, 0.02 mol) and dioxane (10 mL) was stirred for 12 h at ca 30° C. The reaction mixture was diluted with chloroform and washed with water and brine solution. The organic layer was dried over anhydrous $Na_2SO_4$ and concentrated under reduced pressure. The residue was purified by silica gel column chromatography using 1:3 EtOAc-pet. ether to afford 6-fluoro-5-(4-t-butyloxypiperazin-1-yl)-2-mercapto-1H-benzimnidazole (3.3 g, 55%) as a yellow solid. mp 111–112° C.; IR (KBr) 3084, 1701, 1485 $cm^{-1}$; $^1H$ NMR ($CDCl_3+CD_3OD$) δ 1.48 (s, 9H, 3×$CH_3$), 2.22 (s, 1H, SH), 3.00 (t, J=4.8 Hz, 4H, N($CH_2$)$_2$), 3.60 (t, J=4.7 Hz, 4H, N($CH_2$)$_2$), 6.80 (d, J=7.7 Hz, 1H), 7.00 (d, J=12.2 Hz, 1H), 11.52 (brs, 1H, NH); Mass (m/z) 352 ($M^+$.).

Preparation 6

6-Fluoro-(5-(4-ethylenedioxy)piperidin-1-yl)-2-mercapto-1H-benzimidazole:

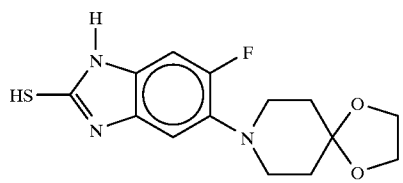

Step 1

N-[2-Nitro-4-fluoro-(5-(4-hydroxy)piperidin-1-yl) phenyl]acetamide (22.0 g, 86%) was prepared by an analogous procedure to that described in preparation 1 (step 3) using N-(2-nitro-4-fluoro-5-chlorophenyl)acetamide (20.0 g, 0.086 mol) (obtained in preparation 1, step 2), 4-hydroxypiperidine (34.4 g, 0.34 mol), potassium hydroxide (7.3 g, 0.13 mol) and dimethyl sulfoxide (80 mL). IR (KBr) 3432, 1682, 1518 $cm^{-1}$; $^1H$ NMR ($CDCl_3$) δd 1.65–1.78 (m, 2H, $CH_2$), 1.99–2.02 (m, 2H, $CH_2$), 2.28 (s, 3H, $CH_3$), 3.13–3.26 (m, 2H, $CH_2$), 3.66–3.77 (m, 2H, $CH_2$), 3.96–3.98 (m, 1H, CH), 7.90 (d, J=14.0 Hz, 1H), 8.42 (d, J=8.6 Hz, 1H), 10.76 (brs, 1H, NH); Mass (m/z) 297 ($M^+$.).

Step 2

The acetamide (10.0 g, 0.034 mol) (obtained in step 1 above) was dissolved in anhydrous dichloromethane (30 mL) and cooled to 0° C., to which a mixture of pyridinium chloro chromate (10.4 g, 0.05 mol) and celite (10 g) was added and stirred for 10 h. The reaction mixture was filtered through celite pad and the filtrate was washed with sodium bicarbonate solution, brine and dried over anhydrous sodium sulfate. Removal of solvent under reduced pressure afforded N-[2-nitro-4-fluoro-5-(4-piperidon-1-yl)phenyl]acetamide (10.0 g, 99%). mp 142–143° C.; IR (KBr) 1728, 1699, 1509 $cm^{-1}$; $^1H$ NMR ($CDCl_3$) δ 2.29 (s, 3H, $CH_3$), 2.64 (t, J=6.1 Hz, 4H, ($CH_2$)$_2$), 3.75 (t, J=5.8 Hz, 4H, N($CH_2$)$_2$), 8.00 (d, J=13.8 Hz, 1H), 8.50 (d, J=8.6 Hz, 1H), 10.72 (brs, 1H, NH); Mass (m/z) 295 ($M^+$.).

Step 3

A mixture of the above compound (5.0 g, 0.017 mol) (obtained in step 2 above), 1,2-ethanediol (1.0 g, 0.034 mol), p-toluenesulphonic acid (catalytic amount) and benzene (20 mL) was refluxed for 2 h using Dean-Stark apparatus. The reaction mixture was diluted with ethyl acetate (50 mL) and washed with sodium bicarbonate solution and brine. The organic layer was dried over $Na_2SO_4$ and concentrated to yield N-[2-nitro-4-fluoro-5-(4-(ethylenedioxy)piperidin-1-yl)phenyl]acetamide (5.5 g, 96%). mp 116–117° C.; IR (KBr) 3321, 1693, 1510 $cm^{-1}$; $^1H$ NMR ($CDCl_3$) δd 1.85 (t, J=5.6 Hz, 4H, ($CH_2$)$_2$), 2.27 (s, 3H, $CH_3$), 3.52 (t, J=5.6 Hz, 4H, N($CH_2$)$_2$), 3.99 (s, 4H, O($CH_2$)$_2$O), 7.88 (d, J=14.2 Hz, 1H), 8.40 (d, J=8.6 Hz, 1H), 10.75 (brs, 1H, NH); Mass (m/z) 339 ($M^+$.).

Step 4

The above compound (5.5 g, 0.016 mol) (obtained in step 3) was deacetylated by an analogous procedure to that described in preparation 4 (step 2) using 6 M NaOH solution (10 mL) and methanol (20 mL) to afford 2-nitro-4-fluoro-5-(4-ethylenedioxy)piperidin-1-yl)aniline (4.5 g, 95%). mp 136–137° C.; IR (KBr) 3336, 1633, 1514 $cm^{-1}$; $^1H$ NMR ($CDCl_3$) δd 1.85 (t, J=5.5 Hz, 4H, ($CH_2$)$_2$), 3.35 (t, J=5.7 Hz, 4H, N($CH_2$)$_2$), 4.00 (s, 4H, O($CH_2$)$_2$O), 6.00 (d, J=7.6 Hz, 1H), 6.02 (brs, 2H, $NH_2$), 7.79 (d, J=14.0 Hz, 1H); Mass (m/z) 297 ($M^+$.).

Step 5

The nitroaniline derivative (7.8 g, 0.026 mol) (obtained in step 4 above) was hydrogenated using 10% Pd-C (3.0 g) in ethyl acetate (50 mL) as described in preparation 1 (step 4) to yield 4-fluoro-5-(4-(ethylenedioxy)piperidin-1-yl)-1,2-phenylenediamine (6.8 g, 99%) as a brown viscous oil. IR (Neat) 3328, 1521 $cm^{-1}$; $^1H$ NMR ($CDCl_3$) δd 1.86 (t, J=5.6 Hz, 4H, ($CH_2$)$_2$), 2.95 (brs, 4H, 2×$NH_2$), 3.03 (t, J=5.7 Hz, 4H, N($CH_2$)$_2$), 4.00 (s, 4H, O($CH_2$)$_2$O), 6.40 (d, J=8.0 Hz, 1H), 6.46 (d, J=14.5 Hz, 1H); Mass (m/z) 267 ($M^+$.).

Step 6

6-Fluoro-5-(4-(ethylenedioxy)piperidin-1-yl)-2-mercapto-1H-benzimidazole (2.0 g, 43%) was prepared by a similar procedure to that described in preparation 1 (step 5) using above diamine (4.0 g, 0.015 mol) (obtained in step 5 above), carbon disulfide (2.2 g, 0.018 mol), ethanol (20 mL) and water (4 mL). mp 160–161° C.; IR (KBr) 3125, 1482 $cm^{-1}$; $^1H$ NMR ($CD_3OD$) δd 1.86 (t, J=5.8 Hz, 4H, ($CH_2$)$_2$), 3.10 (t, J=5.6 Hz, 4H, N($CH_2$)$_2$), 3.98 (s, 4H, O($CH_2$)$_2$O), 6.91 (d, J=7.5 Hz, 1H), 6.95 (d, J=11.6 Hz, 1H); Mass (m/z) 309 ($M^+$.).

Preparation 7

6-Fluoro-5-(4-piperidon-1-yl)-2-mercapto-1H-benzimidazole:

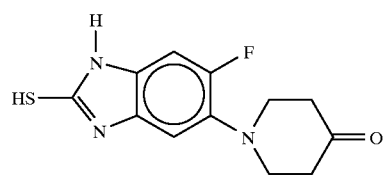

A mixture of 6-fluoro-(5-(4-ethylenedioxy)piperidin-1-yl)-2-mercapto-1H-benzimidazole (1.0 g, 0.0032 mol) (obtained in preparation 6, step 6), 6 N HCl (25 mL) and acetone (10 mL) was refluxed for 1 h. The reaction mixture was neutralized with cold sodium carbonate solution and extracted with ethyl acetate. The organic layer was washed with brine solution, dried and concentrated under reduced pressure to afford the title compound (0.5 g, 63%). mp 260° C. (decomp.); IR (KBr) 3069, 1706, 1482 $cm^{-1}$; $^1H$ NMR (DMSO-$d_6$) δ 2.52 (m, 4H, ($CH_2$)$_2$), 3.26 (m, 4H, N($CH_2$)$_2$), 6.82 (d, J=7.4 Hz, 1H), 7.02 (d, J=11.4 Hz, 1H), 12.52 (brs, 1H, NH); Mass (m/z) 265 ($M^+$.).

Preparation 8

6-Fluoro-5-(4-hydroxylimino)piperidin-1-yl)-2-mercapto-1H-benzimidazole:

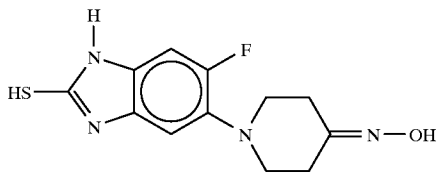

A mixture of 6-fluoro-5-(4-piperidon-1-yl)-2-mercapto-1H-benzimidazole (0.4 g, 0.0015 mol) (obtained in preparation 7), hydroxylamine hydrochloride (0.5 mL), pyridine (0.5 mL) and ethanol (5 mL) was refluxed for 1 h. Ethanol was removed under reduced pressure and water was added to the mixture. The solid separated was filtered and recrystallized from chloroform-methanol mixture to yield the title compound (0.3 g, 75%). mp 290° C. (decomp.); IR (KBr) 3450, 3135, 1486 cm$^{-1}$; $^1$H NMR (DMSO-d$_6$) δ 2.40 (m, 2H, CH$_2$), 2.64 (m, 2H, CH$_2$), 2.30 ) (m, 4H, N(CH$_2$)$_2$), 6.88 (d, J=7.4 Hz, 1H), 7.06 (d, J=1 1.4 Hz, 1H), 10.46 (brs, 1H, OH), 12.44 (brs, 1H, NH); Mass (m/z) 280 (M$^+$.).

Preparation 9

6-Fluoro-5-(4-hydroxypiperidin-1-yl)-2-mercapto-1H-benzimidazole:

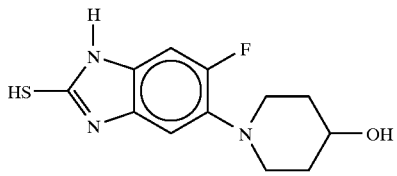

Step 1

N-[2-Nitro-4-fluoro-5-(4-hydroxypiperidin-1-yl)phenyl] acetamide (10.0 g, 0.034 mol) (obtained in preparation 6, step 1) was deacetylated using 6 N NaOH solution (20 mL) and methanol (30 mL) using an analogous procedure to that described in preparation 4 (step 2) to afford 2-nitro-4-fluoro-5-(4-hydroxypiperidin-1-yl) aniline (8.4 g, 80%). mp 238–239 ° C.; IR (KBr) 3357, 3326, 1641 cm$^{-1}$; $^1$H NMR (CDCl$_3$) δd 1.70–1.80 (m, 2H, CH$_2$), 1.99–2.08 (m, 2H, CH$_2$), 2.99–3.12 (m, 2H, NCH$_2$), 3.50–3.62 (m, 2H, NCH$_2$), 3.94 (m, 1H, CH), 6.0 (d, J=7.4 Hz, 1H), 6.02 (brs, 2H, NH$_2$), 7.80 (d, J=14.2 Hz, 1H); Mass (m/z) 255 (M$^+$.).

Step 2

The nitroaniline derivative (8.0 g, 0.03 mol) (obtained in Step 1 above) was hydrogenated using 10% Pd-C (2.0 g) in ethyl acetate (30 mL) by an analogous procedure to that described in preparation 1 (step 4) to yield 4-fluoro-5-(4-hydroxypiperidin-1-yl)-1,2-phenylene diamine (8.5 g, 99%) as a brown viscous oil. IR (Neat) 3426, 3270, 1620 cm$^{-1}$; $^1$H NMR (CDCl$_3$+DMSO-d$_6$) δd 1.60–1.78 (m, 2H, CH$_2$), 1.82–2.06 (m, 2H, CH$_2$), 2.62–2.78 (m, 2H, NCH$_2$), 3.14–3.22 (m, 2H, NCH$_2$), 3.50 (brs, 4H, 2×NH$_2$), 3.68–3.82 (m, 1H, CH), 6.40 (d, J=7.8 Hz, 1H), 6.48 (d, J=13.2 Hz, 1H); Mass (m/z) 225 (M$^+$.).

Step 3

6-Fluoro-5-(4-hydroxypiperidin-1-yl)-2-mercapto-1H-benzimidazole (4.5 g, 62%) was prepared by a similar procedure to that described in preparation 1 (step 5) using the diamine (6.0 g, 0.027 mol) (obtained in step 2 above), carbon disulfide (3.9 g, 0.052 mol), ethanol (30 mL) and water (5 mL). mp 268–269° C.; IR (KBr) 3397, 3124, 1487 cm$^{-1}$; $^1$H NMR (DMSO-d$_6$) δd 1.45–1.56 (m, 2H, CH$_2$), 1.60–1.87 (m, 2H, CH$_2$), 2.24 (s, 1H, SH), 2.64–3.92 (m, 2H, NCH$_2$), 3.11–3.17 (m, 2H, NCH$_2$), 3.30–3.60 (m, 1H, CH), 4.30 (brs, 1H, OH), 6.70 (d, J=7.4 Hz, 1H), 7.00 (d, J=12.6 Hz, 1H), 12.00 (brs, 1H, NH); Mass (m/z) 267 (M$^+$.).

Preparation 10

6-Fluoro-5-(hexamethyleneimin-1-yl)-2-mercapto-1H-benzimidazole:

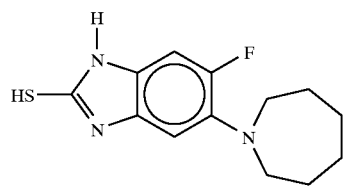

Step 1

2-Nitro-4-fluoro-5-(hexamethyleneimin-1-yl)aniline (8.2 g, 86%) was prepared by an analogous procedure to that described in preparation 1 (step 3) using N-(2-nitro-4-fluoro-5-chlorophenyl)acetamide (9.0 g, 0.038 mol) (obtained in preparation 1, step 1–2), hexamethyleneimine (9.16 g, 0.193 mol) and dimethyl sulfoxide (40 mL). mp 129–130° C.; IR (KBr) 3465, 3327, 1637, 1521 cm$^{-1}$; $^1$H NMR (CDCl$_3$) δd 1.60 (m, 4H, (CH$_2$)$_2$), 1.84 (m, 4H, (CH$_2$)$_2$), 3.48 (t, J=5.1 Hz, 4H, N(CH$_2$)$_2$), 5.82 (d, J=8.0 Hz, 1H), 6.04 (brs, 2H, NH$_2$), 7.74 (d, J=13.7 Hz, 1H); Mass (m/z) 253 (M$^+$.).

Step 2

The nitroaniline derivative (4.8 g, 0.019 mol) (obtained in step 1) was added in portions to a mixture of stannous chloride dihydrate (13.4 g, 0.59 mol) and conc. HCl (50 nmL) at 0° C. and stirred for 3 h at ca. 30° C. The reaction mixture was poured on crushed ice (100 g) and made it alkaline with solid potassium carbonate followed by ammonia solution and extracted with diethyl ether. The ether layer was dried over Na$_2$SO$_4$ and concentrated under reduced pressure to yield 4-fluoro-5-(hexamethyleneimin-1-yl)-1,2-phenylenediamine (4.0 g, 95%) as a viscous oil. IR (Neat) 3331, 1523 cm$^{-1}$; $^1$H NMR (CDCl$_3$) δd 1.62 (m, 4H, (CH$_2$)$_2$), 1.80 (m, 4H, (CH$_2$)$_2$), 3.10 (brs, 4H, 2×NH$_2$), 3.18 (m, 4H, N(CH$_2$)$_2$), 6.30 (d, J=8.5 Hz, 1H), 6.44 (d, J=13.5 Hz, 1H); Mass (m/z) 223 (M$^+$.).

Step 3

6-Fluoro-5-(hexamethyleneimin-1-yl)-2-mercapto-1H-benzimidazole (3.3 g. 70%) was prepared by a procedure similar to that described in preparation 1 (step 5) using the diamine (4.0 g, 0.018 mol) (obtained in step 2 above), carbon disulfide (2.72 g, 0.036 mol), potassium hydroxide (2.0 g, 0.036 mol), ethanol (30 mL) and water (5 mL). mp 301–302° C.; IR (KBr) 3128, 1485 cm$^{-1}$; $^1$H NMR (CDCl$_3$+DMSO-d$_6$) δd 1.64 (m, 4H, (CH$_2$)$_2$), 1.81 (m, 4H, (CH$_2$)$_2$), 2.54 (s, 1H, SH), 3.24 (t, J=5.1 Hz, 4H, N(CH$_2$)$_2$), 6.72 (d, J=7.6 Hz, 1H), 6.84 (d, J=12.1 Hz, 1H), 11.67 (brs, 1H, NH); Mass (m/z) 265 (M$^+$.).

Preparation 11

6-Fluoro-5-(2-methoxymethyl)pyrrolidin-1-yl)-2-mercapto-1H-benzimidazole:

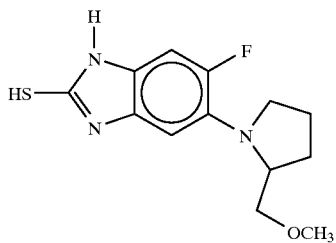

Step 1

2-Nitro-4-fluoro-(5-(2-methoxymethyl)pyrrolidin-1-yl) aniline (4.0 g, 71%) was prepared by a procedure similar to that described in preparation 1 (step 3)using, N-(2-nitro-4-fluoro-5-chlorophenyl)acetamide (5.0 g, 0.021 mol) (obtained in preparation 1, step 2), 2-methoxymethyl pyrrolidine (12.35 g, 0.11 mol), potassium hydroxide (1.8 g, 0.032 mol) and dimethyl sulfoxide (20 mL). mp 94–96° C.; IR (KBr) 3469, 1522 cm$^{-1}$; $^1$H NMR (CDCl$_3$) δd 1.92–2.08 (m, 4H, (CH$_2$)$_2$), 3.18–3.20 (mn, 2H, NCH$_2$), 3.30 (s, 3 H, OCH$_3$), 3.40–3.68 (mn, 2H, CH$_2$O), 4.20–4.32 (mn, 1H, CH), 5.78 (d, J=7.6 Hz, 1H), 6.08 (b)rs, 2H, NH$_2$), 7.78 (d, J=14.4 Hz, 1H); Mass (m/z) 269 (M$^+$.).

Step 2

The nitroaniline derivative (3.0 g, 0.011 mol) (obtained in step 1 above) was reduced by stannous chloride dihydrate (7.56 g, 0.033 mol) and conc. HCl (30 mL) as described in preparation 10 (step 2) to yield 4-fluoro-(5-(2-methoxymethyl)pyrrolidin-1-yl)-1,2-phenylenediamine (2.3 g, 88%) as a viscous oil. IR (Neat) 3343, 1523 cm$^{-1}$; $^1$H NMR (CDCl$_3$) δd 1.82–2.10 (m, 4H, (CH$_2$)$_2$), 3.06 (brs, 4H, 2×NH$_2$), 3.16–3.20 (m, 2H, NCH$_2$), 3.24 (s, 3H, OCH$_3$), 3.40–3.54 (m, 2H, CH$_2$O), 3.72–3.86 (m, 1H, CH), 6.26 (d, J=8.3 Hz, 1H), 6.48 (d, J=13.6 Hz, 1H); Mass (m/z) 239 (M$^+$.).

Step 3

6-Fluoro-(5-(2-methoxymethyl)pyrrolidin-1-yl)-2-mercapto-1H-benzimidazole (3.3 g, 66%) was prepared by a similar procedure to that described in preparation 1 (step 5) using diamine (4.3 g, 0.018 mol) (obtained in step 2 above), carbon disulfide (2.7 g, 0.036 mol), potassium hydroxide (2.0 g, 0.036 mol), ethanol (30 mL) and water (5 mL). mp 226–227° C.; IR (KBr) 3075, 1478 cm$^{-1}$; $^1$H NMR (CDCl$_3$) δd 1.90–2.14 (m, 4H, (CH$_2$)$_2$), 3.10–3.18 (m, 2H, NCH$_2$), 3.24 (s, 3H, OCH$_3$), 3.40–3.60 (m, 2H, CH$_2$O), 3.98–4.06 (m, 1H, CH), 6.62 (d, J=7.4 Hz, 1H), 6.90 (d, J=12.2 Hz, 1H), 10.12 (brs, 1H, NH); Mass (m/z) 281 (M$^+$.).

Preparation 12

6-Fluoro-5-(pyrrolidin-1-yl)-2-mercapto-1H-benzimidazole:

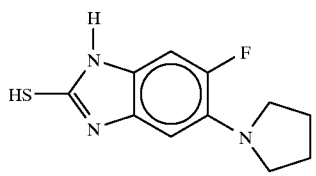

Step 1

2-Nitro-4-fluoro-5-(pyrrolidin-1-yl)aniline (12.3 g, 85%) was prepared by an analogous procedure to that described in preparation 1 (step 3) using N-(2-nitro-4-fluoro-5-chlorophenyl)acetamide (15.0 g, 0.064 mol) (obtained in preparation 1, step 2), pyrrolidine (22.9 g, 0.32 mol), potassium hydroxide (5.4 g, 0.096 mol) and dimethyl sulfoxide (60 mL). mp 115–116° C.; IR (KBr) 3478, 1536 cm$^{-1}$; $^1$H NMR (CDCl$_3$) δd 1.98 (m, 4H, (CH$_2$)$_2$), 3.50 (m, 4H, N(CH$_2$)$_2$), 5.64 (d, J=7.8 Hz, 1H), 6.09 (brs, 2H, NH$_2$), 7.72 (d, J=14.6 Hz, 1H); Mass (m/z) 225 (M$^+$.).

Step 2

The nitroaniline derivative (5.0 g, 0.022 mol) (obtained in step 1 above) was reduced using Fe powder (12.6 g, 0.22 mol), conc. HCl (33 mL) and ethanol (33 mL) as described in preparation 10 (step 2) to yield 4-fluoro-5-(pyrrolidin-1-yl)-1,2-phenylenediamine (4.2 g, 97%) as viscous oil. IR (Neat) 3340, 1524 cm$^{-1}$; $^1$H NMR (CDCl$_3$) δd 1.93 (m, 4H, (CH$_2$)$_2$), 3.24 (m, 4H, N(CH$_2$)$_2$), 3.56 (brs, 4H, 2×NH$_2$), 6.18 (d, J=7.2 Hz, 1H), 6.48 (d, J=13.2 Hz, 1H); Mass (m/z) 195 (M$^+$.).

Step 3

6-Fluoro-5-(pyrrolidin-1-yl)-2-mercapto-1H-benzimidazole (1.77 g, 33%) was prepared by the procedure described in preparation 1 (step 5) using the compound (obtained in step 2 above), (4.5 g, 0.023 mol), carbon disulfide (2.1 g, 0.027 mol), potassium hydroxide (1.56 g, 0.027 mol), ethanol (25 mL) and water (4 mL). mp 170–171° C.; IR (KBr) 3086, 1482 cm$^{-1}$; $^1$H NMR (DMSO-d$_6$) δd 1.88 (m, 4H, (CH$_2$)$_2$), 3.21 (m, 4H, N(CH$_2$)$_2$), 6.50 (d, J=7.8 Hz, 1H), 6.94 (d, J=13.9 Hz, 1H); Mass (m/z) 237 (M$^+$.).

Preparation 13

5-(Morpholin-1-yl)-2-mercapto-1H-benzimidazole:

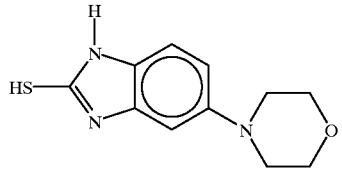

Step 1

3-Chloroaniline (75.0 g, 0.59 mol) was acetylated using acetic anhydride (250 mL, 2.95 mol) by an analogous procedure to that described in preparation 1 (step 1) to yield 3-chlorophenyl acetamide (90.0 g, 90%) as a white solid. mp 70–71° C.; IR (KBr) 3288, 1694 cm$^{-1}$; $^1$H NMR (CDCl$_3$) δ 2.20 (s, 3H, CH$_3$), 7.08 (d, J=8.8 Hz, 1H), 7.22 (t, J=8.2 Hz, 1H), 7.34 (d, J=7.9 Hz, 1H), 7.60 (s, 1H), 7.68 (brs, 1H, NH); Mass (m/z) 169 (M$^+$.).

Step 2

(5-Chloro-2-nitrophenyl)acetamide (35.0 g, 30%) was prepared from 3-chloro phenyl acetamide (90.0 g, 0.53 mol) (obtained in step 1 above), conc. HNO$_3$ (100 mL), conc. H$_2$SO$_4$ (156 mL) and dichloromethane (250 mL), by an analogous procedure to that described in preparation 1 (step 2). mp 115–116° C.; IR (KBr) 3329, 1693, 1504 cm$^{-1}$; $^1$H NMR (CDCl$_3$) δ 2.30 (s, 3H, CH$_3$), 7.12 (d, J=8.4 Hz, 1H), 7.28 (s, 1H), 8.20 (d, J=8.4 Hz, 1H), 10.48 (brs, 1H, NH); Mass (m/z) 214 (M$^+$.).

Step 3

2-Nitro-5-(morpholin-1-yl)aniline (12.0 g, 78%) was prepared by the above acetamide (15.0 g, 0.07 mol) (obtained in step 2 above), morpholine (34.0 g, 0.35 mol), potassium hydroxide (5.88 g, 0.105 mol) and dimethyl sulfoxide (100 mL) by an analogous procedure to that described in preparation 1 (step 3). mp 159–160° C.; IR (KBr) 3334, 1236 cm$^{-1}$; $^1$H NMR (CDCl$_3$) δ 3.30 (t, J=5.0 Hz, 4H, N(CH$_2$)$_2$), 3.80 (t, J=5.2 Hz, 4H, N(CH$_2$)$_2$), 5.96 (s, 1H), 6.12 (brs, 2H, NH$_2$), 6.30 (d, J=7.5 Hz, 1H), 8.08 (d, J=8.8 Hz, 1H); Mass (m/z) 223 (M$^+$.).

Step 4

The nitroaniline derivative (8.9 g, 0.04 mol) (obtained in step 3 above) was hydrogenated using 10% Pd-C (2.5 g) in ethanol (40 mL), by an analogous procedure to that described in preparation 1 (step 4) to yield 3-(morpholin-1-yl)-1,2-phenylenediamine (6.0 g, 78%) as a brown viscous oil. IR (Neat) 3372 cm$^{-1}$; $^1$H NMR (CDCl$_3$) δ 3.08 (t, J=4.5 Hz, 4H, N(CH$_2$)$_2$), 3.24 (brs, 4H, 2×NH$_2$), 3.84 (t, J=4.8 Hz, 4H, O(CH$_2$)$_2$), 6.30 (d, J=8.6 Hz, 1H), 6.38 (s, 1H), 6.68 (d, J=8.4 Hz, 1H) ; Mass (m/z) 193 (M$^+$.).

Step 5

5-(Morpholin-1-yl)-2-mercapto-1H-benzimidazole (5.5 g, 76%) was prepared by an analogous procedure to that described in preparation 1 (step 5) using the diamine (6.0 g, 0.031 mol) (obtained in step 4 above), carbon disulfide (2.83 g, 0.037 mol), potassium hydroxide (2.08 g, 0.037 mol), ethanol (40 mL) and water (10 mL). mp 270° C. (decomp.); IR (KBr) 3353, 1414 cm$^{-1}$; $^1$H NMR (DMSO-d$_6$) δ 2.45 (s, 1H, SH), 2.92 (t, J=4.2 Hz, 4H, N(CH$_2$)$_2$), 3.70 (t, J=4.4 Hz, 4H, O(CH$_2$)$_2$), 6.46 (d, J=8.2 Hz, 1H), 6.70 (s, 1H), 6.80 (d, J=8.3 Hz, 1H); Mass (m/z) 235 (M$^+$.).

Preparation 14

5-(4-Methylpiperazin-1-yl)-2-mercapto-1H-benzimidazole:

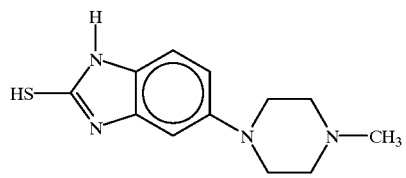

Step 1

5-(4-Methylpiperazin-1-yl)-2-nitroaniline (15.0 g, 93%) was prepared from (5-chloro-2-nitrophenyl)acetamide (15.0 g, 0.07 mol) (obtained in preparation 13, step 2), 4-methyl piperazine (35.0 g, 0.35 mol), potassium hydroxide (5.88 g, 0.105 mol) and dimethyl sulfoxide (100 mL), by an analogous procedure to that described in preparation 1 (step 3). mp 109–110° C.; IR (KBr) 3445, 1249 cm$^{-1}$; $^1$H NMR (CDCl$_3$) δ 2.36 (s,3H, CH$_3$), 2.52 (t, J=5.0 Hz, 4H, N(CH$_2$)$_2$), 3.38 (t, J=5.1 Hz, 4H, N(CH$_2$)$_2$), 5.98 (s, 1H), 6.12 (brs, 2H, NH$_2$), 6.30 (d, J=7.2 Hz, 1H), 8.02 (d, J=8.2 Hz, 1H) ; Mass (m/z) 236 (M$^+$.).

Step 2

The nitroaniline derivative (15.0 g, 0.063 mol) (obtained in step 1 above) was hydrogenated using 10% Pd-C (2.5 g) in ethanol (60 mL) by an analogous procedure to that described in preparation 1 (step 4) to yield 3-(4-methylpiperazin-1-yl)-1,2-phenylene diamine (12.0 g, 92%) as a brown viscous oil. IR (Neat) 3331 cm$^{-1}$; $^1$H NMR (DMSO-d$_6$) δ 2.40 (s, 3H, CH$_3$), 2.64 (t, J=5.4 Hz, 4H, N(CH$_2$)$_2$), 3.10 (t, J=5.3 Hz, 4H, N(CH$_2$)$_2$), 3.40 (brs, 4H, 2×NH$_2$), 6.40 (s, 1H), 6.68 (d, J=8.1 Hz, 1H), 6.80 (d, J=7.8 Hz, 1H); Mass (m/z) 206 (M$^+$.).

Step 3

5-(4-Methylpiperazin-1-yl)-2-mercapto-1H-benzimidazole (11.0 g, 77%) was prepared by an analogous procedure to that described in preparation 1 (step 5) using the diamine (12.0 g, 0.058 mol) (obtained in step 2 above), carbon disulfide (5.2 g, 0.069 mol), potassium hydroxide (3.8 g, 0.069 mol), ethanol (50 mL) and water (10 mL). mp 280° C. (decomp.) ; IR (KBr) 3080, 1480 cm$^{-1}$; $^1$H NMR (CD$_3$OD+CDCl$_3$) δ 2.10(s, 1H, SH), 2.40 (s, 3H, CH$_3$), 2.65 (t, J=4.2 Hz, 4H, N(CH$_2$)$_2$), 3.18 (t, J=4.5 Hz, 4H, N(CH$_2$)$_2$), 6.82 (s, 1H), 6.90 (d, J=8.2 Hz, 1H), 7.12 (d, J=8.7 Hz, 1H), 7.56 (brs, 1H, NH); Mass (m/z) 248 (M$^+$.).

Preparation 15

5-[4-t-Butyloxycarbonylpiperazin-1-yl)-2-mercapto-1H-benzimidazole:

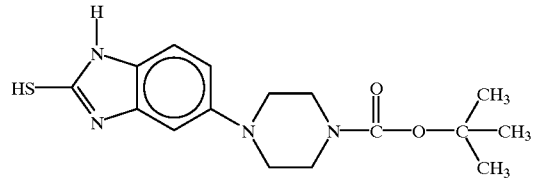

Step 1

5-(Piperazin-1-yl)-2-nitroaniline (10.0 g, 91%) was prepared from (5-chloro-2-nitrophenyl) acetamide (10.7 g, 0.05 mol) (obtained in preparation 13, step 2), piperazine (43.0 g, 0.5 mol), potassium hydroxide (4.2 g, 0.075 mol) and dimethyl sulfoxide (50 mL), by an analogous procedure to that described in preparation 1 (step 3). mp 159–160 ° C.; IR (KBr) 3314, 1624 cm$^{-1}$; $^1$H NMR (CD$_3$OD) δ2.90 (t, J=5.2 Hz, 4H, N(CH$_2$)$_2$), 3.32 (t, J=5–1Hz, 4H, N(CH$_2$)$_2$), 4.80 (brs, 3H, NH), 6.14 (s, 1H), 6.34 (d, J=9.2 Hz, 1H), 7.90 (d, J=9.6 Hz, 1H); Mass (m/z) 222 (M$^+$.).

Step 2

The nitroaniline derivative (10.0 g, 0.045 mol) (obtained in step 1 above) was hydrogenated using 10% Pd-C (1.5 g) in ethanol (45 mL), by an analogous procedure to that described in preparation 1 (step 4) to yield 4-(piperazin-1-yl)-1, 2-phenylenediamine (8.0 g, 93%) as a brown viscous oil. IR (Neat) 3342 cm$^{-1}$; $^1$H NMR (CDCl$_3$) δ 2.80 (brs, 5H, NH), 3.00 (m, 8H, 4×NCH$_2$), 6.30 (d, J=8.2 Hz, 1H), 6.38 (s, 1H), 6.62 (d, J=8.0 Hz, 1H); Mass (m/z) 192 (M$^+$.).

Step 3

5-(Piperazin-1-yl)-2-mercapto-1H-benzimidazole (7.9 g, 85%) was prepared by an analogous procedure to that described in preparation 1 (step 5) using the diamine (8.0 g, 0.04 mol) (obtained in step 2 above), carbon disulfide (3.6 g, 0.048 mol), ethanol (40 nmL) and water (4 nmL). mp 260–261° C.; IR (KBr) 3350, 1498 cm$^{-1}$; $^1$H NMR (DMSO-d$_6$) δ 2.40 (s, 1H, SH), 3.00 (t, J=4.4 Hz, 4H, N(CH$_2$)$_2$), 3.50 (brs, 1H, NH), 4.42 (t, J=4.5 Hz, 4H, N(CH$_2$)$_2$), 6.68 (s, 1H), 6.85 (d, J=8.0 Hz, 1H), 7.03 (d, J=8.4 Hz, 1H) ; Mass (m/z) 234 (M$^+$.).

Step 4

5-(4-t-Butyloxycarbonylpiperazin-1-yl)-2-mercapto-1H-benzimidazole (2.6 g, 52%) was prepared by an analogous procedure to that described in preparation 5 (step 4) using the benzimidazole (3.5 g, 0.015 mol) (obtained in step 3 above), di-t-butyldicarbonate (4.0 g, 0.018 mol), 1N NaOH solution (18 mL, 0.018 mol) and dioxane (10 mL). mp 219–220° C.; IR (KBr) 3093, 1698, 1477 cm$^{-1}$; $^1$H NMR (DMSO-d$_6$) δ 1.42 (s, 9H, 3×CH$_3$), 2.26 (s, 1H, SH), 3.00 (m, 4H, N(CH$_2$)$_2$), 3.48 (m, 4H, N(CH$_2$)$_2$), 6.68 (s, 1H), 6.88

(d, J=8.8 Hz, 1H), 7.16 (d, J=8.6 Hz, 1H), 12.40 (brs, 1H, NH); Mass (m/z) 334 (M⁺.).

Preparation 16

5-(Piperidin-1-yl)-2-mercapto-1H-benzimidazole:

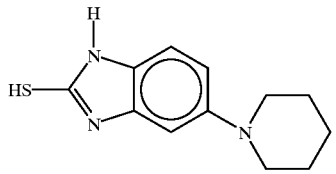

Step 1

5-(Piperidin-1-yl)-2-nitroaniline (14.8 g, 72%) was prepared from (5-chloro-2-nitro phenyl)acetamide (20.0 g, 0.093 mol) (obtained in preparation 13, step 2), piperidine (10.8 g, 0.24 mol), potassium hydroxide (3.9 g, 0.07 mol) and dimethyl sulfoxide (40 mL), by an analogous procedure to that described in preparation 1 (step 3). mp 100–101° C.; IR (KBr) 3461, 1239 cm⁻¹; ¹H NMR (CDCl₃) δd 1.56 (m, 2H, CH₂), 1.68 (m, 4H, (CH₂)₂), 3.40 (m, 4H, N(CH₂)₂) 5.90 (s, (s, 1H), 6.10 (brs, 2H, NH₂), 6.28 (d, J=8.2 Hz, 1H), 8.02 (d, J=8.0 Hz, 1H); Mass (m/z) 221 (M⁺.).

Step 2

The nitroaniline derivative (17.0 g, 0.076 mol) (obtained in step 1 above) was hydrogenated using 10% Pd-C (4.0 g) in ethanol (75 mL) by an analogous procedure to that described in preparation 1 (step 4) to yield 4-(piperidin-1-yl)-1, 2-phenylenediamine (13.8 g, 97%) as a viscous oil. IR (Neat) 3390, 1252 cm⁻¹; ¹H NMR (CDCl₃) 6d 1.52 (m, 2H, CH₂), 1.70 (t, J=4.7 Hz, 4H, (CH₂)₂), 2.90 (t, J=5.0 Hz, 4H, N(CH₂)₂), 3.00 (brs, 4H, 2×NH₂), 6.32 (d, J=8.3 Hz, 1H), 6.38 (s, 1H), 6.62 (d, J=8.1 Hz, 1H); Mass (m/z) 191 (M⁺.).

Step 3

5-(Piperidin-1-yl)-2-mercapto-1H-benzimidazole (10.0 g, 56%) was prepared by an analogous procedure to that described in preparation 1 (step 5) using the diamine (15.0 g, 0.078 mol) (obtained in step 2 above), carbon disulfide (7.16 g, 0.94 mol), potassium hydroxide (5.27 g, 0.094 mol), ethanol (70 mL) and water (10 mL); IR (KBr) 3125, 1497 cm⁻¹; ¹H NMR (DMSO-d₆) δd 1.50 (m, 2H, CH₂), 1.60 (t, J=4.2 Hz, 4H, (CH₂)₂), 3.02 (t, J=4.5 Hz, 4H, N(CH₂)₂), 6.66 (s, 1H), 6.72 (d, J=8.4 Hz, 1H), 7.00 (d, J=8.4 Hz, 1H); Mass (m/z) 233 (M⁺.).

Preparation 17

5-(Hexamethyleneimin-1-yl)-2-mercapto-1H-benzimidazole:

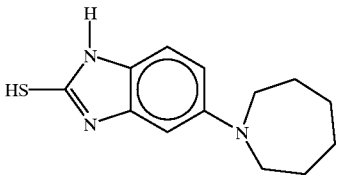

Step 1

5-(Hexamethyleneimin-1-yl)-2-nitroaniline (1.8 g, 33%) was prepared from (5-chloro-2-nitrophenyl)acetamide (5.0 g, 0.023 mol) (obtained in preparation 13, step 2), hexamethyleneimine (11.5 g, 0.12 mol), potassium hydroxide (1.95 g, 0.033 mol) and dimethyl sulfoxide (10 mL) using an analogous procedure to that described in preparation 1 (step 3). mp 97–98° C.; IR (KBr) 3460, 1253 cm⁻¹; ¹H NMR (CDCl₃) 5 1.56 (m, 4H, (CH₂)₂), 1.82 (m, 4H, (CH₂)₂), 3.48 (t, J=6.2 Hz, 4H, N(CH₂)₂), 5.74 (s, 1H), 6.14 (d, J=7.1 Hz, 1H), 6.10 (brs, 2H, NH₂), 7.98 (d, J=9.6 Hz, 1H); Mass (m/z) 235 (M⁺.).

Step 2

The nitroaniline derivative (1.8 g, 0.0076 mol) (obtained in step 1 above) was reduced using stannous chloride dihydrate (5.2 g, 0.023 mol) and Conc. HCl (20 mL) by an analogous procedure to that described in preparation 10 (step 2) to yield 4-(hexamethyleneimin-1-yl)-1,2-phenylenediamine (1.4 g, 90%) as a viscous oil. IR (Neat) 3364, 1257 cm⁻¹, ¹H NMR (CDCl₃) δd 1.52 (m, 4H, (CH₂)₂), 1.78 (m, 4H, (CH₂)₂), 3.37 (t, J=6.0 Hz, 4H, N(CH₂)₂), 3.56 (brs, 4H, 2×NH₂), 6.08 (d, J=8.4 Hz, 1H), 6.12 (s, 1H), 6.64 (d, J=7.4 Hz, 1H); Mass (m/z) 205 (M⁺.).

Step 3

5-(Hexamethyleneimin-1-yl)-2-mercapto-1H-benzimidazole (1.65 g, 98%) was prepared by an analogous procedure to that described in preparation 1 (step 5) using the diamine (1.4 g, 0.0068 mol) (obtained in step 2 above), carbon disulfide (1.03 g, 0.013 mol), potassium hydroxide (0.76 g, 0.013 mol), ethanol (10 mL) and water (2 mL). mp 275–276° C.; IR (KBr) 3092, 1498 cm⁻¹, ¹H NMR (CDCl₃+DMSO-d₆) δd 1.52 (m, 4H, (CH₂)₂), 1.90 (m, 4H, (CH₂)₂), 3.46 (t, J=6.3 Hz, 4H, N(CH₂)₂), 6.44 (s, 1H), 6.50 (d, J=8.9 Hz, 1H), 6.93 (d, J=8.8 Hz, 1H), 11.50 (brs, 1H, NH); Mass (m/z) 247 (M⁺.).

Preparation 18

4,6-Difluoro-5-(morpholin-1-yl)-2-mercapto-1H-benzimidazole:

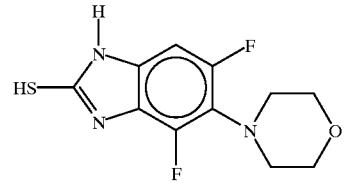

Step 1

2,3,4-Trifluoroaniline (36.7 g, 0.25 mol) was acetylated using acetic anhydride (105 mL, 1.25 mol), using an analogous procedure to that described in preparation 1 (step 1) to yield N-(2,3,4-trifluorophenyl)acetamide (39.0 g, 83%) as a white solid. mp 87–88° C. ; IR (KBr) 3271, 1673, 1514 cm⁻¹; ¹H NMR (CDCl₃) δ 2.16 (s, 3H, CH₃), 6.90 (q, J=4.3 Hz, 1H), 7.60 (brs, 1H, NH), 7.90 (m, 1H); Mass (m/z) 189 (M⁺.).

Step 2

N-(2,3,4-Trifluoro-6-nitrophenyl)acetamide (38.0 g, 82%) was prepared from the acetamide (37.8 g, 0.2 mmol) (obtained in step 1 above), conc. HNO3 (33 mL), conc H₂SO₄ (42 mL), by an analogous procedure to that described in preparation 1 (step 2). mp 96–97° C.; IR (KBr) 3265, 1683, 1502 cm⁻¹; ¹H NMR (CDCl₃) δ 2.30 (s, 3H, CH₃), 7.82 (t, J=4.6 Hz, 1H), 8.24 (brs, 1H, NH); Mass (m/z) 234 (M⁺.).

Step 3

2,4-Difluoro-3-(morpholin-1-yl)-6-nitroaniline (19.2 g, 74%) was prepared from the acetamide (23.0 g, 0.1 mol) (obtained in step 2 above), morpholine (43.5 g, 0.5 mol), potassium hydroxide (8.4 g, 0.15 mol) and dimethyl sulfoxide (100 mL), using an analogous procedure to that described in preparation 1 (step 3). mp 77–78° C.; IR (KBr) 3315, 1489 cm$^{-1}$; $^1$H NMR(CDCl$_3$) δ 3.40 (t, J=4.2 Hz, 4H, N(CH$_2$)$_2$), 3.86 (t, J=4.6 Hz, 4H, O(CH$_2$)$_2$), 6.00 (brs, 2H, NH$_2$), 7.68 (d, J=13.2 Hz, 1H); Mass (m/z) 259 (M$^+$.).

Step 4

The nitroaniline derivative (9.1 g, 0.035 mol) (obtained in step 3 above) was hydrogenated using 10% Pd-C (1.5 g) in ethanol (40 mL), by an analogous procedure to that described in preparation 1 (step 4) to yield 4,6-difluoro-5-(morpholin-1-yl)-1,2-phenylenediamine (7.8 g, 97%) as a brown viscous oil, which was directly converted to 4,6-difluoro-5-(morpholin-1-yl)-2-mercapto-1H-benzimidazole (6.6 g, 70%), following an analogous procedure to that described in preparation 1 (step 5) using carbon disulfide (3.2 g, 0.042 mol), potassium hydroxide (2.3 g, 0.042 mol) ethanol (30 mL) and water (10 mL). mp 119–120° C.; IR (KBr) 3072, 1476 cm$^{-1}$; $^1$H NMR (DMSO-d$_6$) δ 3.06 (t, J=4.4 Hz, 4H, N(CH$_2$)$_2$), 3.68 (t, J=4.6 Hz, 4H, O(CH$_2$)$_2$), 6.84 (d, J=12.8 Hz, 1H); Mass (m/z) 271 (M$^+$.).

Preparation 19

4,6-Difluoro-5-(4-methylpiperazin-1-yl)-2-mercapto-1H-benzimidazole:

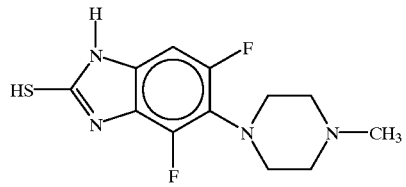

Step 1

2,4-Difluoro-3-(4-methylpiperazin-1-yl)-6-nitroaniline (12.0 g, 70%) was prepared from (2,3,4-trifluoro-6-nitro) acetamide (15.0 g, 0.064 mol) (obtained in preparation 18, step 2), 4-methylpiperazine (32.0 g, 0.032 mol), potassium hydroxide (5.4 g, 0.097 mol) and dimethyl sulfoxide (50 mL), by an analogous procedure to that described in preparation 1 (step 3). IR (Neat) 3475, 1249 cm$^{-1}$, $^1$H NMR (CDCl$_3$) δ 2.32 (s, 3H, CH$_3$), 2.54 (mn, 4H, N(CH$_2$)$_2$), 3.30 (m, 4H, N(CH$_2$)$_2$), 6.08 (brs, 2H, NH$_2$), 7.64 (d, J=13.8 Hz, 1H); Mass (m/z) 272 (M$^+$.).

Step 2

The nitroaniline derivative (10.0 g, 0.036 mol) (obtained in step 1 above) was hydrogenated using 10% Pd-C (2.0 g) in ethanol (40 mL), following an analogous procedure to that described in preparation 1 (step 4) to yield 4,6-difluoro-5-(4-methylpiperazin-1-yl)-1, 2-phenylenediamine (8.8 g, 98.7%) as a brown viscous oil, which was directly converted to 4,6-difluoro-5-(4-methylpiperazine-1-yl)-2-mercapto-1H-benzimidazole (6.7 g, 65%) by an analogous procedure to that described in preparation 1 (step 5) using carbon disulfide (5.5 g, 0.072 mol), potassium hydroxide (2.5 g, 0.043 mmol), ethanol (70 mL) and water (10 mL). mp 280–281° C.; IR (KBr) 3085, 1475 cm$^{-1}$; $^1$H NMR (DMSO-d$_6$) δd 2.22 (s, 3H, NCH$_3$), 2.44 (m, 4H, N(CH$_2$)$_2$), 3.02 (m, 4H, N(CH$_2$)$_2$), 6.86 (d, J=12.8 Hz, 1H), 12.90 (brs, 1H, NH); Mass (m/z) 284 (M$^+$.).

Preparation of Pyridinylmethylthio benzimidazole derivatives:

General Procedure:

2-Mercapto-1H-benzimidazole derivative (1.0 eq) (obtained in preparation 1–19) and sodium hydroxide (2.0 eq) were dissolved in ethanol (1.0 mL / 1.0 mmol) and stirred for 0.5 to 1 h at ca 30° C. To the resulting solution was added 2-chloromethylpyridine hydrochloride derivative (1.0 to 1.1 eq) (prepared by known methods, *J. Med. Chem.* 1992, 35, 1049–1057, U.S. Pat. No. 5,045,552). The mixture was stirred for 6 to 12 h at ca 60 ° C. After the reaction is complete, (monitored by TLC) the reaction mixture was filtered to remove insoluble salts and the filtrate was concentrated under reduced pressure. The residue was purified by silica gel column chromatography using a mixture of methanol and ethyl acetate (1:9 to 1:1) as eluent to afford the title compound.

Following compounds (Examples 1 to 42) were prepared according to the general procedure described above:

EXAMPLE 1

2-[[(4-Methoxy-3,5-dimethyl)pyridin-2-yl]methylthio]-6-fluoro-5-(imidazol-1-yl)-1H-benzimidazole:

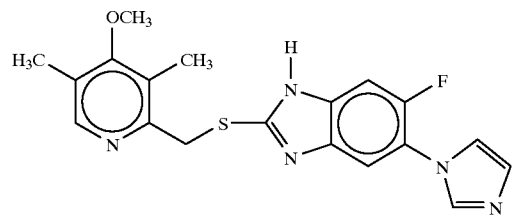

The title compound (2.8 g, 74%) was prepared by the general procedure using 6-fluoro-5-(imidazol-1-yl)-2-mercapto-1H-benzimidazole (2.4 g, 10.0 mmol) (obtained in preparation 1), 4-methoxy-3,5-dimethyl-2-chloromethylpyridine hydrochloride (2.4 g, 11.0 mmol), sodium hydroxide (0.8 g, 20.0 mmol) and ethanol (30 mL). mp 186–187° C.; IR (KBr) 3100, 1399 cm$^{-1}$; $^1$H NMR (CDCl$_3$+CD$_3$OD) δd 2.28 (s, 3H, CH$_3$), 2.40 (s, 3H, CH$_3$), 3.86 (s, 3H, OCH$_3$), 4.68 (s, 2H, SCH$_2$), (7.20 (s, 1H), 7.40 (d, J=4.0 Hz, H), 7.48 (s, 1H), 7.60 (d, J 5.8 Hz, 1H), 7.90 (s, 1H), 8.20 (s, 1H); Mass (m/z) 383 (M+.).

EXAMPLE 2

2-[[3-Methyl-4-(2,2,2-trifluoroethoxy)pyridin-2-yl]methyltio]-6-fluoro-5-(imidazol-1-yl)-1H-benzimidazole:

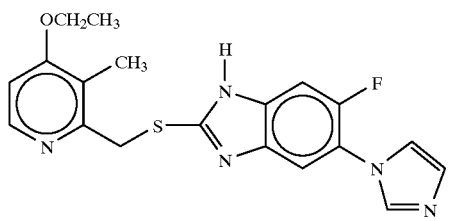

The title compound (2.7 g, 60%) was prepared by the general procedure using 6-fluoro-5-(imidazol-1yl)-2-mercapto-1H-benzimidazole (2.4 g, , 10.0 mmol) (obtained in preparation 1), 3 methyl-4-(2,2,2-trifluoroethoxy-2-chloromethylpyridine hydrochloride (3.0 g, 11.0 mmol), sodium hydroxide (0.8 g, 20.0 mmol) and ethanol (20 mL). mp 197–198° C. ; IR (KBr) 3436, 1255, 1112 cm$^{-1}$; $^1$H NMR (DMSO-d$_6$) δ 2.28 (s, 3H, CH$_3$), 4.78 (s, 2H, SCH$_2$), 4.98 (q, J=5.9 Hz, 2H, OCH$_2$CF$_3$), 7.00 (d, J=6.0 Hz, 1H), 7.08 (s, 1H), 7.52 (s, 1H), 7.60 (d, J=6.0 Hz, 1H), 7.68 (d, J=4.2 Hz, 1H), 8.00 (s, 1H), 8.30 (d, J=5.7 Hz, 1H), 13.15 (brs, 1H, NH); Mass (m/z) 437 (M⁺.).

EXAMPLE 3

2-[[(4-Methoxy-3-methyl)pyridin-2-yl]methylthio]-6-fluoro-5-(imidazol-1-yl)-1H-benzimidazole:

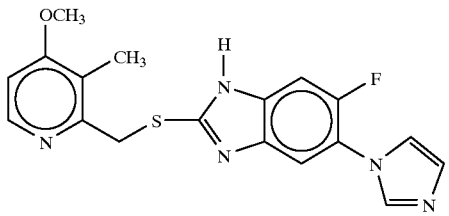

The title compound (0.5 g, 62%) was prepared by the general procedure using 6-fluoro-5-(imidazol-1-yl)-2-mercapto-1H-benzimidazole (0.41 g, 2.0 mmol) (obtained in preparation 1), 4-methoxy-3-methyl-2-chloromethylpyridine hydrochloride (0.5 g, 2.0 mmol), sodium hydroxide (0.16 g, 4.0 mmol) and ethanol (20 mL). mp 214–215 °C.; IR (KBr) 3101, 1582, 1437 cm⁻¹; ¹H NMR (CDCl₃+CD₃OD) δ 2.30 (s, 3H, CH₃), 3.90 (s, 3H, OCH₃), 4.60 (s, 2H, SCH₂), 6.88 (d, J=5.7 Hz, 1H), 7.20 (s, 1H), 7.32 (s, 1H), 7.42 (d, J=7.6 Hz, 1H), 7.56 (d, J=6.1 Hz, 1H), 7.82 (s, 1H), 8.30 (d, J=6.1 Hz, 1H); Mass (m/z) 369 (M⁺.).

EXAMPLE 4

2-[[(4-(3-Methoxypropoxy)-3-methyl)pyridin-2-yl]methylthio]-6-fluoro-5-(imidazol-1-yl)-1H-benzimidazole:

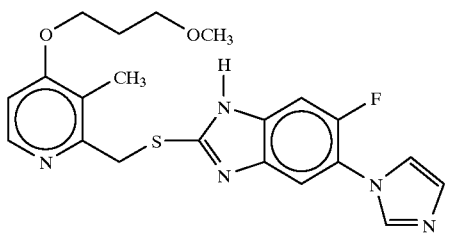

The title compound (0.46 g, 64%) was prepared by the general procedure using 6-fluoro-5-(imidazol-1-yl)-2-mercapto-1H-benzimidazole (0.40 g, 1.7 mmol) (obtained in preparation 1), 4-(3-methoxypropoxy)-3-methyl-2-chloromethylpyridine hydrochloride (0.45 g, 1.7 mmol), sodium hydroxide (0.14 g, 3.4 mmol) an d ethanol (20 mL). IR (KBr) 3435, 1582, 1428 cm⁻¹; ¹H NMR-(CDCl₃) δ 2.18 (2H, CH₂), 2.30 (s, 3H, CH₃), 3.40 (s, 3H, OCH₃), 3.60(t, J=5.7 Hz, 2H, OCH, ), 4.20 (t, J=5.9 Hz, 2H, OCH₂), 4.40 (s, 2H, SCH₂), 6.80 (d, J=6.1 Hz, 1H), 7.20 (s, 1H), 7.26 (s, 1H), 7.40 (d, J=7.8 Hz, 1H), 7.46 (d, J=10.2 Hz, 1H), 7.80 (s, 1H), 8.38 (d, J=5.9 Hz, 1H), 13.80 (brs, 1H, NH); Mass (m/z) 427 (M⁺.).

EXAMPLE 5

2-[[(4-Methoxy)pyridin-2-yl]methylthio]-6-fluoro-5-(imidazol-1-yl)-1H-benzimidazole:

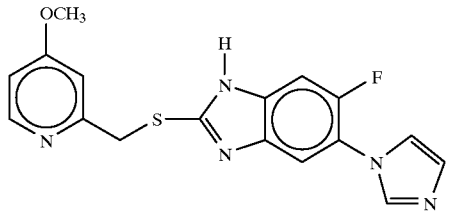

The title compound (1.9 g, 60%) was prepared by the general procedure using, 6-fluoro-5-(imidazol-1-yl)-2-mercapto-1H-benzimidazole (2.1 g, 9.0 mmol), (obtained in preparation 1) 4-methoxy-2-chloromethylpyridine hydrochloride (1.74 g, 9.0 mmol), sodium hydroxide (0.72 g, 18.0 mmol) and ethanol (25 mL). mp 86–87° C.; IR (KBr) 3443, 1600 cm⁻¹; ¹H NMR (CDCl₃) δ 3.90 (s, 3H, OCH₃), 4.38 (s, 2H, SCH₂), 6.92 (d, J=5.7 Hz, 1H), 6.96 (s, 1H), 7.30 (m, 2H), 7.42 (d, J=10.2 Hz, 1H), 7.58 (d, J=7.8 Hz, 1H), 7.80 (s, 1H), 8.50 (d, J=6.0 Hz, 1H), 14.00 (brs, 1H, NH); Mass (m/z) 355 (M⁺.).

EXAMPLE 6

2-[[(4-Chloro-3-methyl)pyridin-2-yl]methylthio]-6-fluoro-5-(imidazol-1-yl)-1H-benzimidazole:

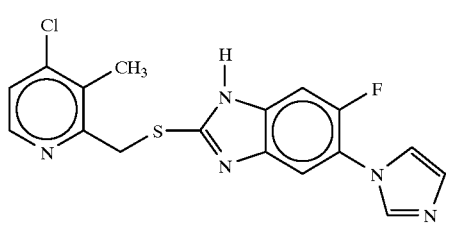

The title compound (0.72 g, 70%) was prepared by the general procedure using 6-fluoro-5-(imidazol-1-yl)-2-mercapto-1H-benzimidazole (0.65 g, 2.75 mmol) (obtained in preparation 1), 4-chloro-3-methyl-2-chloromethylpyridine hydrochloride (0.58 g, 2.75 mmol), sodium hydroxide (0.22 g, 5.5 mmol) and ethanol (25 mL). mp 131–132° C.; IR (KBr) 3392, 1502, 1437 cm⁻¹; ¹H NMR (CDCl₃) δ 2.60 (s, 3H, CH₃), 4.60 (s, 2H, SCH₂), 7.26 (d, J=5.6 Hz, 1H), 7.28 (s, 1H), 7.36 (s, 1H), 7.42 (d, J=10.3 Hz, 1H), 7.58 (d, J=7.8 Hz, 1H), 7.88 (s, 1H), 8.40 (d, J=5.9 Hz, 1H), 13.00 (brs, 1H, NH); Mass (m/z) 373 (M⁺).

EXAMPLE 7

2-[[(4-Methoxy-3,5-dimethyl)pyridin-2-yl]methylthio]-6-fluoro-5-(morpholin-1-yl)-1H-benzimidazole:

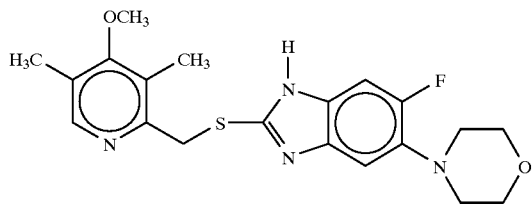

The title compound (2.6 g, 65%) was prepared by the general procedure using 6-fluoro-5-(morpholin-1-yl)-2-mercapto-1H-benzimidazole (2.55 g, 10.0 mmol) (obtained in preparation 2), 4-methoxy-3,5-dimethyl-2-chloromethylpyridine hydrochloride (2.0 g, 11.0 mmol), sodium hydroxide (0.8 g, 20.0 mmol) and ethanol (20 mL). mp 176–177° C.; IR (KBr) 3427, 1476, 1428 cm$^{-1}$; $^1$H NMR (DMSO-d$_6$) δ 2.20 (s, 3H, CH$_3$), 2.28 (s, 3H, CH$_3$), 3.38 (t, J=4.2 Hz, 4H, N(CH$_2$)$_2$), 3.70 (s, 3H, OCH$_3$), 3.78 (t, J=4.4 Hz, 4H, O(CH$_2$)$_2$), 4.64 (s, 2H, SCH$_2$), 7.20 (d, J=8.2 Hz, 1H), 7.38 (d, J=10.3 Hz, 1H), 8.20 (s, 1H), 12.60 (brs, 1H, NH); Mass (m/z) 402 (M+.).

EXAMPLE 8

2-[[3-Methyl-4-(2,2,2-trifluoroethoxy)pyridin-2-yl]methylthio]-6-fluoro-5-(morpholin-1-yl)-1H-benzimidazole:

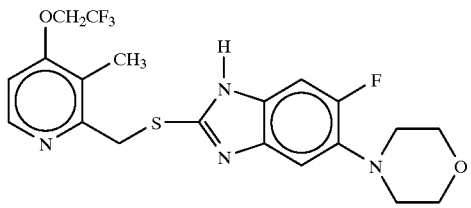

The title compound (2.1 g, 58%) was prepared by the general procedure using 6-fluoro-5-(morpholin-1-yl)-2-mercapto-1H-benzimidazole (2.0 g, 8.0 mmol) (obtained in preparation 2), 3-methyl-4-(2,2,2-trifluoroethoxy)-2-chloromethylpyridine hydrochloride (2.2 g, 8.0 mmol), sodium hydroxide (0.64 g, 16.0 mmol) and ethanol (20 mL). mp 205–206° C.; IR (KBr) 3340, 1584, 1269 cm$^{-1}$; $^1$H NMR (CD$_3$OD) δ 2.28 (s, 3H, CH$_3$), 3.08 (t, J=4.0 Hz, 4H, N(CH$_2$)$_2$), 3.90 (t, J=4.5 Hz, 4H, O(CH$_2$)$_2$), 4.60 (s, 2H, SCH$_2$), 4.70 (q, J=6.1 Hz, 2H, OCH$_2$CF$_3$), 7.00 (d, J=5.9 Hz, 1H), 7.12 (d, J=8.2 Hz, 1H), 7.20 (d, J=12.4 Hz, 1H), 8.26 (d, J=5.7 Hz, 1H); Mass (m/z) 456 (M$^+$.).

EXAMPLE 9

2-[[(4-Methoxy-3-methyl)pyridin-2-yl]methylthio]-6-fluoro-5-(morpholin-1-yl)-1H-benzimidazole:

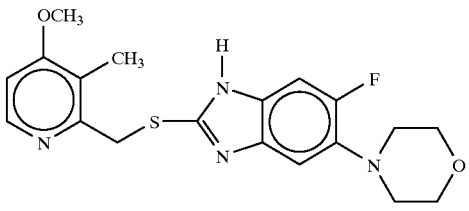

The title compound (0.58 g, 75%) was prepared by the general procedure using 6-fluoro-5-(morpholin-1-yl)-2-mercapto-1H-benzimidazole (0.51 g, 2.0 mmol) (obtained in preparation 2), 4-methoxy-3-methyl-2-chloromethylpyridine hydrochloride (0.42 g, 2.0 mmol), sodium hydroxide (0.16 g, 4.0 mmol) and ethanol (10 mL). mp 106–107° C.; IR (KBr) 3340, 1582, 1428 cm$^{-1}$; $^1$H NMR (CDCl$_3$) δ 2.30 (s, 3H, CH$_3$), 3.10 (t, J=4.6 Hz, 4H, N(CH$_2$)$_2$), 3.90 (m, 7H, OCH$_3$+OCH$_2$)$_2$), 4.38 (s, 2H, SCH$_2$), 6.80 (d, J=5.6 Hz, 1H), 7.10 (d, J=7.8 Hz, 1H), 7.26 (d, J=10.2 Hz, 1H), 8.36 (d, J=6.0 Hz, 1H); Mass (m/z) 388 (M$^+$.).

EXAMPLE 10

2-[[(4-(3-Methoxypropoxy)-3-methyl)pyridin-2-yl]methylthio]-6-fluoro-5-(morpholin-1-yl)-1H-benzimidazole:

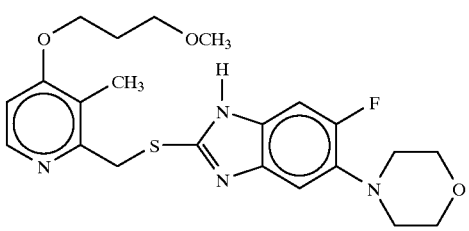

The title compound (0.22 g, 62%) was prepared by the general procedure using 6-fluoro-5-(morpholin-1-yl)-2-mercapto-1H-benzimidazole (0.19 g, 0.76 mmol) (obtained in preparation 2), 4-(3-methoxypropoxy)-3-methyl-2-chloromethylpyridine hydrochloride (0.2 g, 0.76 mmol), sodium hydroxide (0.06 g, 1.52 mmol) and ethanol (5 mL). IR (KBr) 3431, 1584, 1428 cm$^{-1}$; $^1$H NMR (CDCl$_3$) δ 2.10 (m, 2H, CH$_2$), 2.28 (s, 3H, CH$_3$), 3.08 (t, J=4.5 Hz, 4H, N(CH$_2$)$_2$), 3.38 (s, 3H, OCH$_3$), 3.60 (t, J=5.6 Hz, 2H, OCH$_2$), 3.90 (t, J=4.8 Hz, 4H, (OCH$_2$)$_2$), 4.18 (t, J=6.0 Hz, 2H, OCH$_2$), 4.38 (s, 2H, SCH$_2$), 6.80 (d, J=5.7 Hz, 1H), 7.10 (d, J=7.8 Hz, 1H), 7.26 (d, J=10.4 Hz, 1H), 8.38 (d, J=5.6 Hz, 1H); Mass (m/z) 446 (M$^+$.).

EXAMPLE 11

2-[[(4-Morpholin-1-yl)-3-methylpyridin-2-yl]methylthio]-6-fluoro-5-(morpholin-1-yl)-1H-benzimidazole:

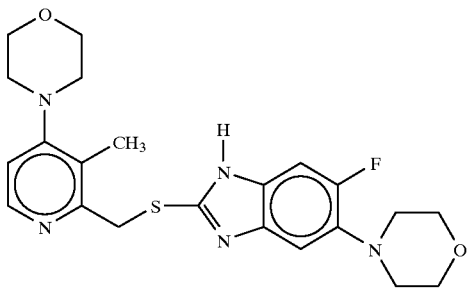

The title compound (0.4 g, 25%) was prepared by the general procedure using 6-fluoro-5-(morpholin-1-yl)-2-mercapto-1H-benzimidazole (0.9 g, 3.6 mmol) (obtained in preparation 2), 4-(morpholin-1-yl)-3-methyl-2-chloromethylpyridine hydrochloride (1.06 g, 3.9 mmol), sodium hydroxide (0.36 g, 9.1 mmol) and ethanol (10 mL). mp 102–103° C.; IR (KBr) 3440, 1471 cm$^{-1}$; $^1$H NMR (CDCl$_3$) δ 2.34 (s, 3H, CH$_3$), 3.02 (t, J=4.6 Hz, 4H, N(CH$_2$)$_2$, 3.08 (t, J=4.5 Hz, 4H, N(CH$_2$)$_2$), 3.90 (m, 8H, 2×O(CH$_2$)$_2$), 4.36 (s, 2H, SCH$_2$), 6.86 (d, J=5.6 Hz, 1H), 7.12 (d, J=7.2 Hz, 1H), 7.24 (d, J=10.3 Hz, 1H), 8.40 (d, J=5.6 Hz, 1H); Mass (m/z) 443 (M$^+$).

EXAMPLE 12

2-[[(4-Piperidin-1-yl)-3-methylpyridin-2-yl]methylthio]-6-fluoro-5-(morpholin-1-yl)-1H-benzimidazole:

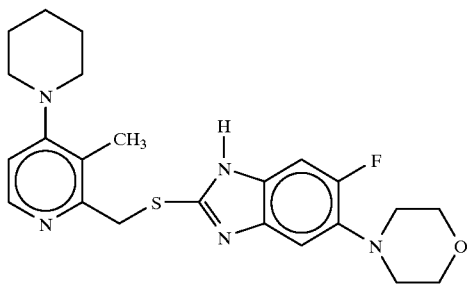

The title compound (2.7 g, 50%) was prepared by the general procedure using 6-fluoro-5-(morpholin-1-yl)-2-mercapto-1H-benzimidazole (0.30 g, 1.2 mmol) (obtained in preparation 2), 4-(piperidin-1-yl)-3-methyl-2-chloromethylpyridine hydrochloride (0.31 g, 1.2 mmol), sodium hydroxide (0.10 g, 2.4 mmol) and ethanol (1 0 mL). mp 289–290° C.; IR (KBr) 3429, 1580, 1474 cm$^{-1}$; $^1$H NMR (CDCl$_3$) δ 1.50–1.84 (m, 6H, (CH$_2$)$_3$), 2.30 (s, 3H, CH$_3$), 2.98 (t, J=5.4 Hz, 4H, N(CH$_2$)$_2$), 3.08 (t, J=4.6 Hz, 4H, N(CH)), 3.92 (t, J=4.5 Hz, 4H, O(CH$_2$)$_2$), 4.32 (s, 2H, SCH$_2$), 6.82 (d, J=5.5 Hz, 1H), 7.12 (d, J=7.4 Hz, 1H), 7.26 (d, J 12.0 Hz, 1H), 8.30 (d, J=5.7 Hz, 1H); Mass (m/z) 441 (M$^+$.).

EXAMPLE 13

2-[[4-(4-Methylpiperazin-1-yl)-3-methylpyridin-2-yl]methylthio]-6-fluoro-5-(morpholin-1-yl)-1H-benzimidazole:

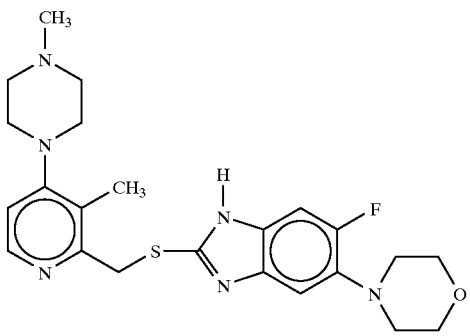

The title compound (0.5 g, 27%) was prepared by the general procedure using 6-fluoro-5-(morpholin-1-yl)-2-mercapto-1H-benzimidazole (1.02 g, 4.0 mmol) (obtained in preparation 2), 4-(4-methylpiperazin-1-yl)-3-methyl-2-chloromethylpyridine hydrochloride (1.1 g, 4.0 mmol), sodium hydroxide (0.24 g, 8.0 mmol) and ethanol (10 mL). mp 289–290° C.; IR (KBr) 3440, 1581, 1429 cm$^{-1}$; $^1$H NMR (CDCl$_3$) δ 2.30 (s, 3H, CH$_3$), 2.40 (s, 3H, CH)$_3$ 2.60 (m, 4H, N(CH$_2$)$_2$), 3.00 (m, 8H, 2×(CH$_2$)$_2$), 3.90 (t, J=4.5 Hz, 4H, O(CH$_2$)$_2$), 4.32 (s, 2H, SCH$_2$), 6.84 (d, J=5.6 Hz, 1H), 7.10 (d, J=7.6 Hz, 1H), 7.22 (d, J=11.2 Hz, 1H), 8.32 (d, J=5.7 Hz, 1H); Mass (m/z) 456 (M+.).

EXAMPLE 14

2-[[(3-Methyl)pyridin-2-yl]methylthio]-6-fluoro-5-(morpholin-1-yl)-1H-benzimidazole:

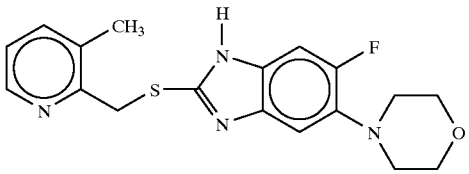

The title compound (0.1 g, 71%) was prepared by the general procedure using 6-fluoro-5-(morpholin-1-yl)-2-mercapto-1H-benzimidazole (0.1 g, 0.4 mmol) (obtained in preparation 2), 3-methyl-2-chloromethylpyridine hydrochloride (0.07 g, 0.4 mmol), sodium hydroxide (0.05 g, 1.2 mmol) and ethanol (5 mL). IR (KBr) 2972, 1428 cm$^{-1}$; $^1$H NMR (CDCl$_3$) δ 2.42 (s, 3H, CH$_3$), 3.08 (t, J=4.4 Hz, 4H, N(CH$_2$)$_2$), 3.90 (t, J=4.4 Hz, 4H, O(CH$_2$)$_2$), 4.36 (s, 2H, SCH$_2$), 7.10 (d, J=7.4 Hz, 1H), 7.20–7.28 (m, 2H), 7.60 (d, J=7.5 Hz, 1H), 8.48 (d, J=5.6 Hz, 1H); Mass (m/z) 358 (M$^+$.).

EXAMPLE 15

2-[[(4-Methoxy-3,5-dimethyl)pyridin-2-yl]methylthio]-6-fluoro-5-(piperidin-1-yl)-1H-benzimidazole:

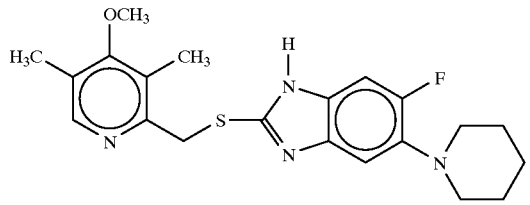

The title compound (0.48 g, 60%) was prepared by the general procedure using, 6-fluoro-5-(piperidin-1-yl)-2-mercapto-1H-benzimidazole (0.5 g, 2.0 mmol) (obtained in preparation 3), 4-methoxy-3,5-dimethyl-2-chloromethylpyridine hydrochloride (0.37 g, 2.0 mmol), sodium hydroxide (0.16 g, 4.0 mmol) and ethanol (10mL). mp 100–101° C.; IR (KBr) 3100, 1475, 1427 cm$^{-1}$; $^1$H NMR (CDCl$_3$) δ 1.60 (m, 2H, CH$_2$), 1.80 (m, 4H, (CH$_2$)$_2$), 2.30 (s, 3H, CH$_3$), 2.38 (s, 3)H, CH$_3$), 3.00 (t, J=5.4 Hz, 4H, N(CH$_2$)$_2$), 3.82 (s, 3 H, OCH$_3$), 4.34 (s, 2H, SCH$_2$), 7.12 (d, J=6.9 Hz, 1H), 7.22 (d, J=12.0 Hz, 1H), 8.30 (s, 1H); Mass (m/z) 400 (M$^+$.).

EXAMPLE 16

2-[[3-Methyl-4-(2,2,2-trifluoroethoxy)pyridin-2-yl]methylthio]-6-fluoro-5-(piperidin-1-yl)-1H-benzimidazole:

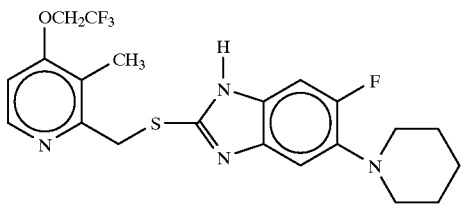

The title compound (0.45 g, 50%) was prepared by the general procedure using 6-fluoro-5-(piperidin-1-yl)-2-mercapto-1H-benzimidazole (0.5 g, 2.0 mmol) (obtained in preparation 3), 3-methyl-4-(2,2,2,-trifluoroethoxy)-2-chloromethylpyridine hydrochloride (0.47 g, 2.0 mmol), sodium hydroxide (0.16 g, 4.0 mmol) and ethanol (10 mL). mp 160–161° C.; 1R (KBr) 3122, 1585, 1432 cm$^{-1}$; $^1$H NMR (CDCl$_3$) δ 1.60 (m, 2H, CH$_2$), 1.80 (m, 4H, (CH$_2$)$_2$), 2.38 (s, 3H, CH$_3$), 3.00 (m, 4H, N(CH$_2$)$_2$), 4.40 (s, 2H, SCH$_2$), 4.46 (q, J=7.8 Hz, 2H, OCH$_2$CF$_3$), 6.74 (d, J=5.5 Hz, 1H), 7.18 (d, J=7.6 Hz, 1H), 7.26 (d, J=10.0 Hz, 1H), 8.42 (d, J=5.5 Hz, 1H), 12.50 (s, 1H, NH); Mass (m/z) 454 (M$^+$).

EXAMPLE 17

2-[[(4-Methoxy-3-methyl)pyridin-2-yl]methylthio]-6-fluoro-5-(piperidin-1-yl)-1H-benzimidazole:

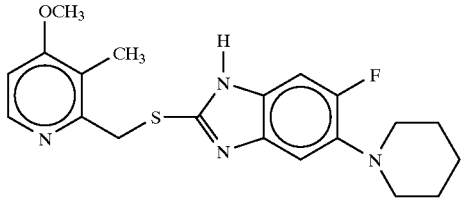

The title compound (0.5 g, 65%) was prepared by the general procedure using 6-fluoro-5-(piperidin-1-yl)-2-mercapto-1H-benzimidazole (0.5 g, 2.0 mmol) (obtained in preparation 3), 4-methoxy-3-methyl-2-chloromethylpyridine hydrochloride (0.4 g, 2.0 mmol), sodium hydroxide (0.16 g, 4.0 mmol) and ethanol (10 mL). mp 170–171° C.; IR (KBr) 3121, 1582, 1170 cm$^{-1}$; $^1$H NMR (CDCl$_3$) δ 1.60 (m, 2H, CH$_2$), 1.80 (m, 4H, (CH$_2$)$_2$), 2.26 (s, 3H, CH$_3$), 3.00 (m, 4H, N(CH$_2$)$_2$), 3.94 (s, 3H, OCH$_3$), 4.40 (s, 2H, SCH$_2$), 6.80 (d, J=5.4 Hz, 1H), 7.18 (d, J=7.2 Hz, 1H), 7.24 (d, J=10.6 Hz, 1H), 8.40 (d, J=5.6 Hz, 1H); Mass (m/z) 386 (M$^+$).

EXAMPLE 18

2-[[(4-Piperidin-1-yl)-3-methylpyridin-2-yl]methylthio]-6-fluoro-5-(piperidin-1-yl)-1H-benzimidazole:

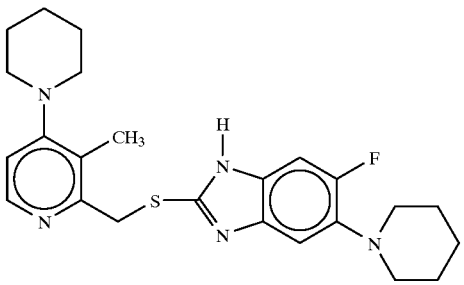

The title compound (0.95 g, 63%) was prepared by the general procedure using, 6-fluoro-5-(piperidin-1-yl)-2-mercapto-1H-benzimidazole (0.70 g, 2.8 mmol) (obtained in preparation 3), 4-(piperidin-1-yl)-3 )-methyl-2-chloromethylpyridine hydrochloride (0.91 g, 3.5 mmol), sodium hydroxide (0.30 g, , 7.7 mmol) and ethanol (15 mL). mp 161–162° C.; IR (KBr) 3430, 1581, 1429 cm$^{-1}$; $^1$H NMR (CDCl$_3$) δ 1.60 (m, 4H, 2×CH$_2$), 1.74 (m, 8H, 2×(CH$_2$)$_2$), 2.30 (s, 3)H, CH$_3$), 3.00 (m, 8H, 2×N(CH$_2$)$_2$), 4.32 (s, 2H, SCH$_2$), 6.82 (d, J=5.4 Hz, 1H), 7.12 (d, J=7.7 Hz, 1H), 7.24 (d, J=12.1 Hz, 1H), 8.28 (d, J=5.5 Hz, 1H); Mass (m/z) 439 (M$^+$).

EXAMPLE 19

2-[[(4-Methoxy-3,5-dimethyl)pyridin-2-yl]methylthio]-6-fluoro-5-(4-methylpiperazin-1-yl)-1H-benzimidazole:

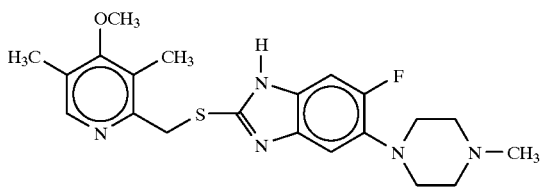

The title compound (1.8 g, 60%) was prepared by the general procedure using 6-fluoro-5-(4-methylpiperazin-1-yl)-2-mercapto-1H-benzimidazole (2.0 g, 7.5 mmol) (obtained in preparation 4), 4-methoxy-3,5-dimethyl-2-chloromethylpyridine hydrochloride (1.52 g, 8.2 mmol), sodium hydroxide (0.6 g, 15.0 mmol) and ethanol (30 mL). mp 120–121° C.; IR (KBr) 3390, 1475, 1427 cm$^{-1}$; $^1$H NMR (CDCl$_3$) δ 2.30 (s, 3H, CH$_3$), 2.32 (s, 3H, CH$_3$), 2.70 (s, 3H, CH$_3$), 3.10 (m, 4H, N(CH$_2$)$_2$), 3.36 (m, 4H, N(CH$_2$)$_2$), 3.80 (s, 3H, OCH$_3$), 4.34 (s, 2H, SCH$_2$), 7.12 (d, J=7.5 Hz, 1H), 7.22 (d, J=8.4 Hz, 1H), 8.32 (s, 1H); Mass (m/z) 415 (M$^+$).

EXAMPLE 20

2-[[3-Methyl-4-(2,2,2-trifluoroethoxy)pyridin-2-yl]methylthio]-6-fluoro-5-(4-methylpiperazin-1-yl)-1H-benzimidazole:

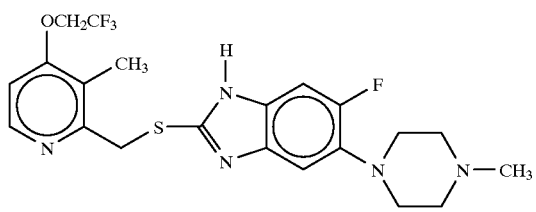

The title compound (1.48 g, 64%) was prepared by the general procedure using 6-fluoro-5-(4-methylpiperazin-1-yl)-2-mercapto-1H-benzimidazole (1.33 g, 5.0 mmol) (obtained in preparation 4), 3-methyl-4-(2,2,2-trifluoroethoxy)-2-chloromethylpyridine hydrochloride (1.5 g, 5.5 mmol), sodium hydroxide (0.4 g, 10.0 mmol) and ethanol (25 mL). mp 109–110° C.; IR (KBr) 3397, 1584, 1258 cm$^{-1}$; $^1$H NMR (DMSO-d$_6$) δ 2.38 (s, 3H, CH$_3$), 2.80 (s, 3H, CH$_3$), 3.12 (m, 4H, N(CH$_2$)$_2$), 3.40 (m, 4H, N(CH$_2$)$_2$), 4.48 (q, J=7.9 Hz, 2H, OCH$_2$CF$_3$), 4.60 (s, 2H, SCH$_2$), 6.80 (d, J=5.8 Hz, 1H), 7.14 (d, J=7.1 Hz, 1H), 7.24 (d, J=11.7 Hz, 1H), 8.40 (d, J=5.5 Hz, 1H); Mass (m/z) 469 (M$^+$).

EXAMPLE 21

2[[(4-Methoxy-3-methyl)pyridin-2-yl]methylthio]-6-fluoro-5-(4-methylpiperazin-1-yl)-1H-benzimidazole:

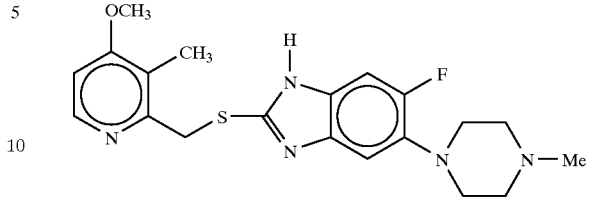

The title compound (2.5 g, 78%) was prepared by the general procedure using 6-fluoro-5-(4-methylpiperazin-1-yl)-2-mercapto-1H-benzimidazole (2.12 g, 8.0 mmol) (obtained in preparation 4), 4-methoxy-3-methyl-2-chloromethylpyridine hydrochloride (1.6 g, 8.0 mmol), sodium hydroxide (0.64 g, , 16.0 mmol) and ethanol (30 mL). mp 118–120° C.; IR (KBr) 3432, 1585, 1296 cm$^{-1}$; $^1$H NMR (DMSO-d$_6$) δ 2.20 (s, 3H, CH$_3$), 2.38 (s, 3H, CH$_3$), 2.60 (m, 4H, N(CH$_2$)$_2$), 3.00 (m, 4H, N(CH$_2$)$_2$), 3.86 (s, 3H, OCH$_3$), 4.68 (s, 2H, SCH$_2$), 6.98 (d, J=5.6 Hz, 1H), 7.12 (d, J=7.1 Hz, 1H), 7.28 (d, J=11.2 Hz, 1H), 8.30 (d, J=5.8 Hz, 1H), 12.76 (b, rs, 1H, NH); Mass (m/z) 401 (M$^+$).

EXAMPLE 22

2-[[(3-Methyl)pyridin-2-yl]methylthio]-6-fluoro-5-(4-methylpiperazin-1-yl)-1H-benzimidazole:

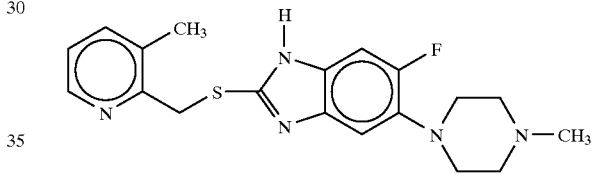

The title compound (0.6 g, 22%) was prepared by the general procedure using 6-fluoro-5-(4-methylpiperazin-1-yl)-2-mercapto-1H-benzimidazole (2.0 g, 7.5 mmol) (obtained in preparation 4), 3-methyl-2-chloromethylpyridine hydrochloride (1.0 g, 7.5 mmol), sodium hydroxide (0.36 g, 9.0 mmol) and ethanol (15 mL). IR (Neat) 3150, 1429 cm$^{-1}$; $^1$H NMR (CDCl$_3$) δ 2.42 (s, 3H, CH$_3$), 2.50 (s, 3H, CH$_3$), 2.90 (m, 4H, N(CH$_2$)$_2$), 3.20 (m, 4H, N(CH$_2$)$_2$), 4.38 (s, 2H, SCH$_2$), 7.12 (d, J=7.6 Hz, 1H), 7.20–7.26 (m, 2H), 7.58 (d, J=7.4 Hz, 1H), 8.46 (d, J=4.6 Hz, 1H); Mass (m/z) 371 (M$^+$.).

EXAMPLE 23

2-[[(4-Methoxy-3,5-dimethyl)pyridin-2-yl]methylthio]-6-fluoro-5-(4-t-butyloxycarbonyl piperazin-1-yl)-1H-benzimidazole:

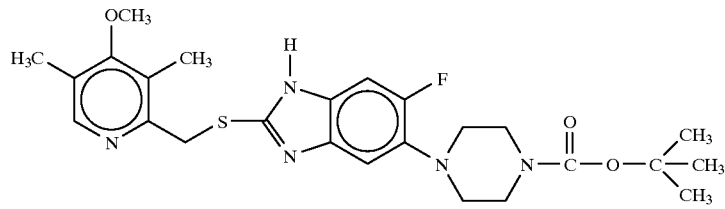

The title compound (1.5 g, 52%) was prepared by the general procedure using 6-fluoro-5-(4-t- butyloxycarbonylpiperazin-1-yl)-2-mercapto-1H-benzimidazole (2.0 g, 5.7 mmol) (obtained in preparation 5), 4-methoxy-3-methyl-2-chloromethylpyridine hydrochloride (1.0 g, 5.7 mmol), sodium hydroxide (0.34 g, 8.52 mmol) and ethanol (20 mL). mp 147–148° C.; IR (KBr) 3066, 1696, 1462 cm$^{-1}$; $^1$H NMR (CDCl$_3$) δ 1.50 (s, 9H, 3×CH$_3$), 2.28 (s, 3H, CH$_3$), 2.34 (s, 3H, CH$_3$), 3.00 (m, 4H, N(CH$_2$)$_2$), 3.60 (m, 4H, N(CH$_2$)$_2$), 3.80 (s. 3H, OCH$_3$), 4.38 (s, 2H, SCH$_2$), 7.10 (d, J=7.6 Hz, 1H), 7.22 (d, J=11.0 Hz, 1H), 8.24 (s, 1H); Mass (m/z) 501 (M$^+$).

EXAMPLE 24

2-[[(4-Methoxy-3-methyl)pyridin-2-yl]methylthiol-]-6-fluoro-5-(4-t-butyloxycarbonylpiperazin-1-yl)-1H-benzimidazole:

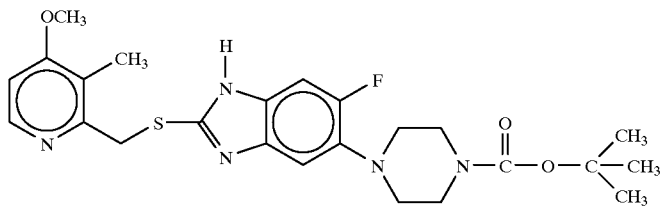

The title compound (0.65 g, 66%) was prepared by the general procedure using 6-fluoro-5-(4-t-butyloxycarbonylpiperazin-1-yl)-2-mercapto-1H-benzimidazole (0.70 g, 2.0 mmol) (obtained in preparation 5), 4-methoxy-3-methyl-2-chloromethylpyridine hydrochloride (0.42 g, 2.0 mmol), sodium hydroxide (0.16 g, 4.0 mmol) and ethanol (10 mL). mp 84–85° C.; IR (KBr) 3431, 1684, 1427 cm$^{-1}$; $^1$H NMR (CDCl$_3$) δ 1.50 (s, 9H 3×CH$_3$), 2.26 (s, 3H, CH$_3$), 3.00 (m, 4H, N(CH$_2$)$_2$), 3.68 (m, 4H, N(CH$_2$)$_2$), 3.90 (s, 3H, OCH$_3$), 4.40 (s, 2H, SCH$_2$), 6.78 (d,J=5.6Hz, 1H), 7.10 (d,J=7.3 Hz, 1H), 7.24 (d,J=10.8 Hz, 1H), 8.40 (d,J=5.7Hz, 1H); Mass (m/z) 487 (M$^+$).

EXAMPLE 25

2-[[(4-Methoxy-3-methyl)pyridin-2-yl]methylthio]-6-fluoro-5-(4-(ethylenedioxy)piperidin-1-yl)-1H-benzimidazole:

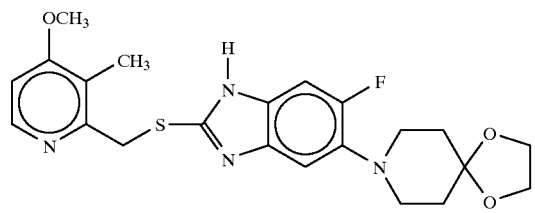

The title compound (1.3 g, 46%) was prepared by the general procedure using 6-fluoro-5-(4-ethylenedioxy)piperidin-1-yl)-2-mercapto-1H-benzimidazole (2.0 g, 6.4 mmol) (obtained in preparation 6), 4-methoxy-3-methyl-2-chloromethylpyridine hydrochloride (1.2 g, 6.6 mmol), sodium hydroxide (0.78 g, 8.4 mmol) and ethanol (20 mL). mp 70–71 ° C.; IR (KBr) 3416, 1582, 1097 cm$^{-1}$; $^1$H NMR (CDCl$_3$) δ 1.92 (t,J=5.4 Hz, 4H, (CH$_2$)$_2$), 2.24 (s, 3H, CH$_3$), 3.16 (t,J=5.2 Hz, 4H, N(CH$_2$)$_2$), 3.92 (s, 3H, OCH$_3$), 4.02 (s, 4H, O(CH$_2$)$_2$O), 4.32 (s, 2H, SCH$_2$), 6.76 (d,J=5.8Hz, 1H), 7.04 (d,J=6.8Hz, 1H), 7.22 (d,J=10.8 Hz, 1H), 8.36 (d,J=5.8Hz, 1H), 12.50 (brs, 1H, NH); Mass (m/z) 444 (M+).

EXAMPLE 26

2-[[(4-Methoxy-3-methyl)pyridin-2-yl]methylthio]-6-fluoro-5-(4-piperidon-1-yl)-1H-benzimidazole):

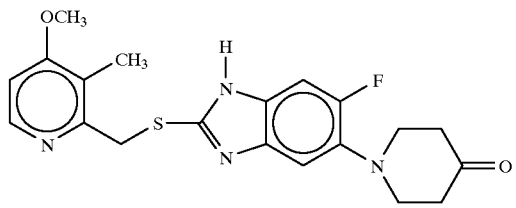

A mixture of $^2$-[[(4-methoxy-3-methyl)pyridin-2-yl] methylthio]-6-fluoro-5-(4-(ethylenedioxy)piperidin-1-yl)-1H-benzimidazole (0.7 g, 1.8 mmol) (obtained in Example 25), 6N HCl (20 mL) and acetone (25 mL) was refluxed for 12 h. The acetone was removed under reduced pressure and the residue was dissolved in ethyl acetate. The organic phase was washed with saturated NaHCO$_3$ solution, brine and dried over Na$_2$SO$_4$ and concentrated under reduced pressure to afford the title compound (0.3 g, 50%). mp 128–129 ° C.; IR (KBr) 3337, 1710, 1433 cm$^{-1}$; $^1$H NMR (CDCl$_3$) δ 2.28 (s, 3H, CH$_3$), 2.66 (t,J=5.8 Hz, 4H, (CH$_2$)$_2$), 3.38 (t,J =5.8 Hz, 4H, N(CH$_2$)$_2$), 3.90 (s, 3H, OCH$_3$), 4.34 (s, 2H, SCH$_2$), 6.78 (d,J=5.8 Hz, 1H), 7.12 (d,J=7.8 Hz, 1H), 7.24 (d,J=11.4 Hz, 1H), 8.36 (d,J=5.8 Hz, 1H), 13.00 (brs, 1H, NH); Mass (m/z) 400 (M$^{+)}$·

EXAMPLE 27

2-[[(4-Methoxy-3-methyl)pyridin-2-yl]methylthio]-6-fluoro-5-(4-(hydroxyimino)piperidin-1-yl)-1H-benzimidazole:

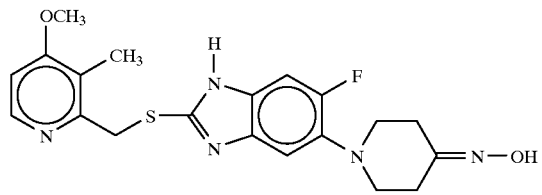

The title compound (1.0 g, 84%) was prepared by the general procedure using 6-fluoro-5-(4-(hydroxyimino) piperidin-1-yl)-2-mercapto-1H-benzimidazole (0.8 g, 2.8 mmol) (obtained in preparation 8), 4-methoxy-3-methyl-2-chloromethylpyridine hydrochloride (0.6 g, 2.8 mmol), sodium hydroxide (0.23 g, 5.6 mmol) and ethanol (10 mL). mp 210–211° C.; IR (KBr) 3450, 3052, 1582, 1478 cm$^{-1}$; $^1$H NMR (DMSO-d$_6$) δ 2.22 (s, 3H, CH$_3$), 2.44 (t,J=5.4 Hz, 2H, CH$_2$), 2.68 (t,J=5.4 Hz, 2H, CH$_2$), 3.08 (t,J=6.2 Hz, 4H, N(CH$_2$)$_2$), 3.88 (s, 3H, OCH$_3$), 4.68 (s, 2H, SCH$_2$), 6.98 (d,J=6.6 Hz, 1H), 7.22 (d,J=7.8 Hz, 1H), 7.26 (d,J=9.3 Hz, 1H), 8.28 (d,J=6.6 Hz, 1H), 10.44, (s, 1H, OH), 12.60 (s, 1H, NH); Mass (m/z) 415 (M$^+$).

EXAMPLE 28

2-[[(4-Methoxy-3-methyl)pyridin-2-yl]methylthio]-6-fluoro-5-[4-(hydroxy)piperidin-1-yl]-1H-benzimidazole:

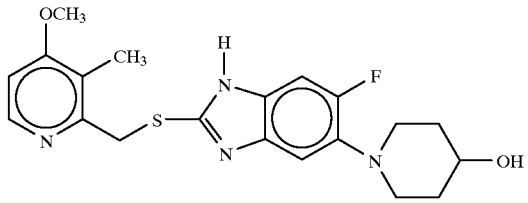

The title compound (1.5 g, 83%) was prepared by the general procedure using 6-fluoro-5-(4-hydroxypiperidin-1-yl)-2-mercapto-1H-benzimidazole (1.28 g, 4.17 mmol) (obtained in preparation 9), 4-methoxy-3-methyl-2-chloromethylpyridine hydrochloride (0.88 g, 4.17 mmol), sodium hydroxide (0.4 g, 10.4 mmol) and ethanol (30 mL). mp 116–117° C.; IR (KBr) 3450, 3156, 1075 cm$^{-1}$; $^1$H NMR (CDCl$_3$) δ 1.68–1.72 (m, 2H, CH$_2$), 1.92–2.08 (m, 2H, CH$_2$), 2.22 (s, 3H, CH$_3$), 2.80 (t,J=5.7 Hz, 2H, NCH$_2$), 3.24 (t,J=5.6 Hz, 2H, NCH$_2$), 3.88 (s, 3H, OCH$_3$), 3.80–3.92 (m, 2H, CHOH), 4.32 (s, 2H, SCH$_2$), 6.72 (d,J=5.8 Hz, 1H), 7.08 (d,J=7.2 Hz, 1H), 7.20 (d,J=12.0 Hz, 1H), 8.32 (d,J=5.8 Hz, 1H), 13.00 (brs, 1H, NH); Mass (m/z) 402 (M$^+$).

EXAMPLE 29

2-[[(4-Methoxy-3-methyl)pyridin-2-yl]methylthio]-6-fluoro-5-(hexamethyleneimin-1-yl)-1H-benzimidazole:

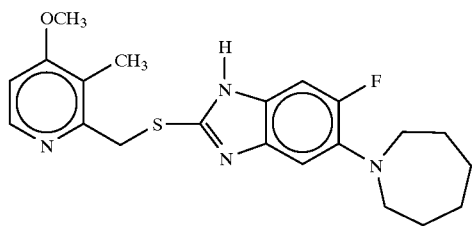

The title compound (0.5 g, 41%) was prepared by the general procedure using 6-fluoro-5-(hexamethyleneimin-1-yl)-2-mercapto-1H-benzimidazole (0.82 g, 3.1 mmol) (obtained in preparation 10), 4-methoxy-3-methyl-2-chloromethylpyridine hydrochloride (0.58 g,3.4 mmol), sodium hydroxide (0.25 g, 6.2 mmol) and ethanol (15 mL). mp 73–74° C.; IR (KBr) 3075, 1582, 1478 cm$^{-1}$; $^1$H NMR (CDCl$_3$) δ 1.67 (m, 4H, (CH$_2$)$_2$), 1.86 (m, 4H, (CH$_2$)$_2$), 2.26 (m, 3H, CH$_3$), 3.30 (t,J=5.8 Hz, 4H, N(CH$_2$)$_2$), 3.92 (s, 3H, OCH$_3$), 4.34 (s, 2H, SCH$_2$), 6.78 (d,J=5.8 Hz, 1H), 7.04 (d,J=9.9 Hz, 1H), 7.20 (d,J=12.8 Hz, 1H), 8.38 (d,J=5.7 Hz, 1H); Mass (m/z) 400 (M+).

EXAMPLE 30

2-[[(4-Morpholin-1-yl)-3-methyl)pyridin-2-yl]methylthio]-6-fluoro-5-(hexamethyleneimin-1-yl)-1H-benzimidazole:

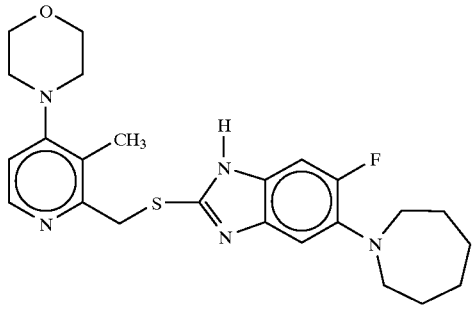

The title compound (0.47 g, 27%) was prepared by the general procedure using 6-fluoro-5-(hexamethyleneimin-1-yl)-2-mercapto-1H-benzimidazole (1.0 g, 3.77 mmnol) (obtained in preparation 10), 4-(morpholin-1-yl)-3-methyl-2-chloromethylpyridine hydrochloride (0.99 g, 3.77 mmol), sodium hydroxide (0.3 g, 7.54 mmol) and ethanol (10 mL). mp 141–142° C.; IR (KBr) 3438, 1579 cm$^{-1}$ ; $^1$HNMR (CDCl$_3$) δ 1.68 (m, 4H, (CH$_2$)$_2$), 1.82 (m, 4H, (CH$_2$)$_2$), 2.32 (s, 3H, CH$_3$), 2.98 (t,J=4.6 Hz, 4H, N(CH$_2$)$_2$), 3.28 (t,J=5.0 Hz, 4H, N(CH$_2$)$_2$), 3.88 (t,J=4.2 Hz, 4H, O(CH$_2$)$_2$), 4.34 (s, 2H, SCH$_2$), 6.84 (d,J=5.6 Hz, 1H), 7.02 (d,J=7.8 Hz, 1H), 7.18 (d,J=12.9 Hz, 1H), 8.36 (d,J=5.5 Hz, 1H); Mass (m/z) 455 (M$^+$).

EXAMPLE 31

2-[[4-(Methoxy-3-methyl)pyridin-2-yl]methylthiol]-6-fluoro-5-(2 (methoxymethyl)pyrrolidin-1-yl)-1H-benzimidazole:

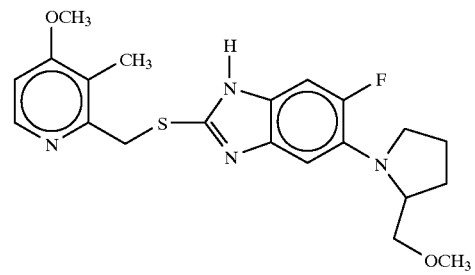

The title compound (1.1 g, 68%) was prepared by the general procedure using 6-fluoro-5-(2-(methoxymethyl)pyrrolidin-1-yl)-2-mercapto-1H-benzimidazole (1.0 g, 3.55 mmol) (obtained in preparation 11), 4-methoxy-3-methyl-2-chloromethylpyridine hydrochloride (0.67 g, 3.9 mmol), sodium hydroxide (0.28 g, 7.11 mmol) and ethanol (10 mL). IR (Neat) 2930, 1582, 1477 cm$^{-1}$; $^1$H NMR (CDCl$_3$) δ 1.90–2.04 (m, 4H, (CH$_2$)$_2$), 2.26 (s, 3H, CH$_3$), 3.10–3.24 (m, 2H, NCH$_2$), 3.30 (s, 3H, OCH$_3$), 3.48–3.70 (m, 2H, OCH$_2$), 3.92 (s, 3H, OCH$_3$), 4.00–4.10 (m, 1H, CH), 4.36 (s, 2H, SCH$_2$), 6.78 (d,J=6.6 Hz, 1H), 6.98 (d,J=7.6 Hz, 1H), 7.24 (d,J=13.1 Hz, 1H), 8.38 (d,J=5.9 Hz, 1H); Mass (m/z) 416 (M$^+$).

EXAMPLE 32

2-[[(4-Methoxy-3-methyl)pyridin-2-yl]methylthio]-6-fluoro-5-(pyrrolidin-1-yl)-1H-benzimidazole:

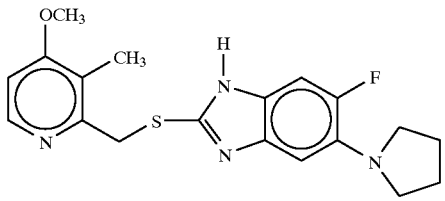

The title compound (0.85 g, 54%) was prepared by the general procedure using 6-fluoro-5-(pyrrolidin-1-yl)-2-mercapto-1H-benzimidazole (0.95 g, 4.2 mmol) (obtained in preparation 12), 4-methoxy-3-methyl-2-chloromethylpyridine hydrochloride (0.81 g, 4.2 mmol), sodium hydroxide (0.34 g, 8.4 mmol) and ethanol (10 mL). mp 120–121° C.; IR (Neat) 3145, 1582, 1433 cm$^{-1}$; $^1$H NMR (CDCl$_3$) δ 1.96 (m, 4H, (CH$_2$)$_2$), 2.24 (s, 3H, CH$_3$), 3.32 (m, 4H, N(CH$_2$)$_2$), 3.88 (s, 3H, OCH$_3$), 4.36 (s, 2H, SCH$_2$), 6.76 (d,J=5.6 Hz, 1H), 6.84 (d,J=7.8 Hz, 1H), 7.20 (d,J=13.1 Hz, 1H), 8.34 (d,J=5.8 Hz, 1H); Mass (m/z) 372 (M$^+$).

EXAMPLE 33

2-[[(4-Methoxy-3,5-dimethyl)pyridin-2-yl]methylthiol-]-5-(morpholin-1-yl)-1H-benzimidazole:

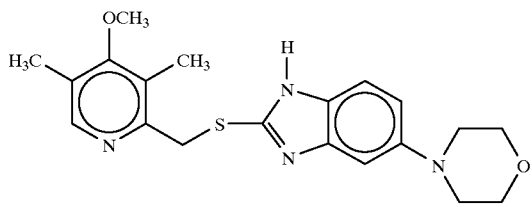

The title compound (1.05 g, 66%) was prepared by the general procedure using 5-(morpholin-1-yl)-2-mercapto-1H-benzimidazole (1.0 g, 4.2 mmol) (obtained in preparation 13), 4-methoxy-3,5-dimethyl-2-chloromethylpyridine hydrochloride (0.9 g, 4.2 mmol), sodium hydroxide (0.34 g, 8.4 mmol) and ethanol (10 mL). IR (KBr) 3427, 1446, 1288 cm$^{-1}$; $^1$H NMR (CDCl$_3$) δ 2.28 (s, 3H, CH$_3$), 2.32 (s, 3H, CH$_3$), 3.14 (t,J=4.6 Hz, 4H, N(CH$_2$)$_2$), 3.80 (s, 3H, OCH$_3$), 3.88 (t, J=4.8 Hz, 4H, O(CH$_2$)$_2$), 4.38 (s, 2H, SCH$_2$), 6.90 (d,J=6.7 Hz, 1H), 7.08 (s, 1H), 7.46 (d, J=8.8 Hz, 1H), 8.24 (s, 1H), 10.8 (brs, 1H, NH); Mass (m/z) 384 (M$^+$).

EXAMPLE 34

2-[[3-Methyl-4-(2,2,2-trifluoroethoxy)pyridin-2-yl]methylthio]-5-(morpholin-1-yl)-1H-benzimidazole:

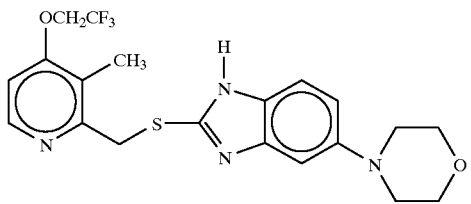

The title compound (1.05 g, 61%) was prepared by the general procedure using 5-(morpholin-1-yl)-2-mercapto-1H-benzimidazole (1.0 g, 4.2 mmol) (obtained in preparation 13), 3-methyl-4-(2,2,2-trifluoroethoxy)-2-chloromethylpyridine hydrochloride (1.15 g, 4.2 mmol), sodium hydroxide (0.34 g, 8.4 mmol) and ethanol (10 mL). IR (Neat) 3432, 1582, 1282 cm$^{-1}$; 1H NMR (CDCl$_3$) δ 2.30 (s, 3H, CH$_3$), 3.14 (t,J=4.6 Hz, 4H, N(CH$_2$)$_2$), 3.90 (t,J=4.8 Hz, 4H, O(CH$_2$)$_2$), 4.42 (q,J=4.6 Hz, 2H, OCH$_2$CF$_3$), 4.48 (s, 2H, SCH$_2$), 6.70 (d,J=5.9 Hz, 1H), 6.90 (d,J=6.7 Hz, 1H), 7.08 (s, 1H), 7.48 (d,J=8.7 Hz, 1H), 8.40 (d,J=5.8 Hz, 1H), 8.50 (brs, 1H, NH); Mass (m/z) 438 (M$^+$).

EXAMPLE 35

2-[[(4-Methoxy-3-methyl)pyridin-2-yl]methylthio]-5-(morpholin-1-yl)-1H-benzimidazole:

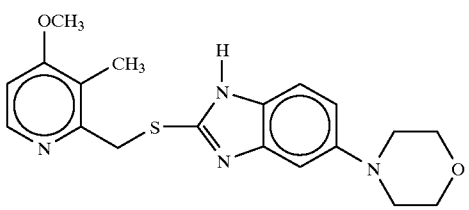

The title compound (1.0 g, 55%) was prepared by the general procedure using 5-(morpholin-1-yl)-2-mercapto-1H-benzimidazole (1.2 g, 5.0 mmol) (obtained in preparation 13), 4-methoxy-3-methyl-2-chloromethylpyridine hydrochloride (1.0 g, 5.0 mmol), sodium hydroxide (0.4 g, 10.0 mmol) and ethanol (30 mL). mp 60–61° C.; IR (KBr) 3150, 1581, 1295 cm$^{-1}$; $^1$H NMR (CDCl$_3$) δ 2.18 (s, 3H, CH$_3$), 3.12 (t,J4.5 Hz, 4H, N(CH$_2$)$_2$), 3.86 (t,J=4.6 Hz, 4H, O(CH$_2$)$_2$), 3.90 (s, 3H, OCH$_3$), 4.54 (s, 2H, SCH$_2$), 6.92 (d,J=5.8 Hz, 1H), 6.98 (d,J=8.9 Hz, 1H), 7.02 (s, 1H), 7.40 (d,J=9.2 Hz, 1H), 8.20 (d,J=5.8 Hz, 1H) ; Mass (m/z) 370 (M$^+$).

EXAMPLE 36

2-[[(4-Methoxy-3,5-dimethyl)pyridin-2-yl]methylthio]-5-(4-methylpiperazin-1-yl)-1H-benzimidazole:

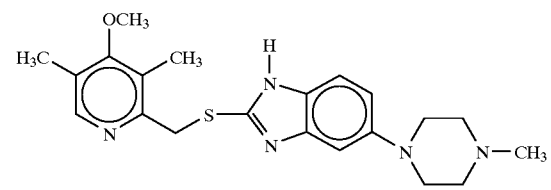

The title compound (1.4 g, 60%) was prepared by the general procedure using 5-[4-methylpiperazin-1-yl)-2-mercapto-1H-benzimidazole (1.5 g, 6.0 mmol) (obtained in preparation 14), 4-methoxy-3,5-dimethyl-2-chloromethylpyridine hydrochloride (1.0 g, 6.0 mmol), sodium hydroxide (0.48 g, 12.0 mmol) and ethanol (30 mL). IR (Neat) 3404, 1446 cm$^{-1}$; $^1$H NMR (CDCl$_3$) δ 2.30 (s, 3H, CH$_3$), 2.38 (s, 3H, CH$_3$), 2.52 (s, 3H, NCH$_3$), 2.90 (t,J=4.6 Hz, 4H, N(CH$_2$)$_2$), 3.32 (t,J=5.0 Hz, 4H, N(CH$_2$)$_2$), 3.80 (s, 3H, OCH$_3$), 4.34 (s, 2H, SCH$_2$), 6.90 (d, J=6.7 Hz, 1H), 7.08 (s, 1H), 7.44 (d,J=8.7 Hz, 1H), 8,30 (s, 1H). Mass (m/z) 397 (M$^+$).

EXAMPLE 37

2-[[(4-Methoxy-3-methyl)pyridin-2-yl]methylthio]-5-(4-methylpiperazin-1-yl)-1H-benzimidazole:

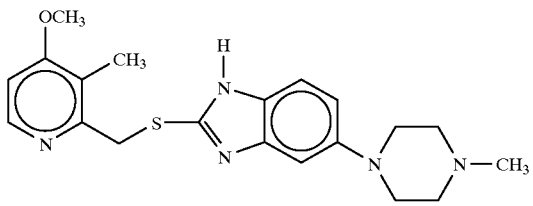

The title compound (0.96 g, 64%) was prepared by the general procedure using 5-(4-methylpiperazin-1-yl)-2-mercapto-1H-benzimidazole (0.99 g, 4.0 mmol) (obtained in preparation 14), 4-methoxy-3-methyl-2-chloromethylpyridine hydrochloride (0.83 g, 4.0 mmol), sodium hydroxide (0.32 g, 8.0 mmol) and ethanol (20 mL). mp 134–135° C.; IR (KBr) 3440, 1441 cm$^{-1}$; $^1$H NMR (DMSO-d$_6$) δ 2.20 (s, 3H, CH$_3$), 2.24 (s, 3H, CH$_3$), 2.52 (t,J=5.4 Hz, 4H, N(CH$_2$)$_2$), 3.08 (t,J=5.6 Hz, 4H, N(CH$_2$)$_2$), 3.84 (s, 3H, OCH$_3$), 4.60 (s, 2H, SCH$_2$), 6.82 (d, J=6.2 Hz, 1H), 6.90 (s, 1H), 7.00 (d,J=7.6 Hz, 1H), 7.40 (d,J=8.9 Hz, 1H), 8.24 (d,J=5.9 Hz, 1H), 12.60 (brs, 1H, NH); Mass (m/z) 383 (M$^+$).

EXAMPLE 38

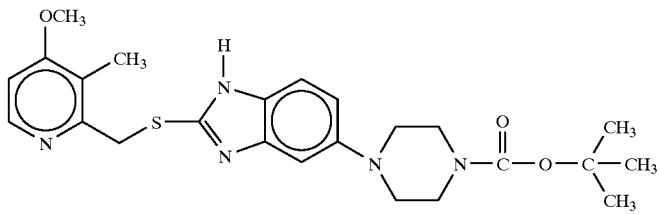

The title compound (0.93 g, 66%) was prepared by the general procedure using 5-[4-t-butyloxycarbonylpiperazin-1-yl)-2-mercapto-1H-benzimidazole (1.0 g, 3.0 mmol) (obtained in preparation 15), 4-methoxy-3-methyl-2-chloromethylpyridine hydrochloride (0.74 g, 3.5 mmol), sodium hydroxide (0.24 g, 6.0 mmol) and ethanol (30 mL). mp 180–181° C.; IR (KBr) 3247, 1694, 1421 cm$^{-1}$; $^1$H NMR (CD$_3$OD) δ 1.50 (s, 9H, 3×CH$_3$), 2.16 (s, 3H, CH$_3$). 3.1 0 (t,J=4.8 Hz, 4H, N(CH$_2$)$_2$), 3.60 (t,J=4.5 Hz, 4H, N(CH$_2$)$_2$), 3.90 (s, 3H, OCH$_3$), 4.36 (s, 2H, SCH$_2$), 6.76 (d,J=5.6 Hz, 1H), 6.98 (d,J=6.8 Hz, 1H), 7.04 (s, 1H), 7.42 (d,J=8.7 Hz, 1H), 8.36 (d, J=5.8 Hz, 1H); Mass (m/z) 469 (M$^+$).

EXAMPLE 39

2-[[(4-Methoxy-3-methyl)pyridin-2-yl]methylthio]-5-(piperidin-1-yl)-1H-benzimidazole:

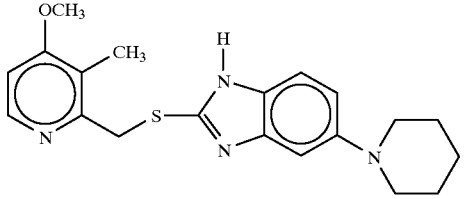

The title compound (2.2 g, 62%) was prepared by the general procedure using 5-(piperidin-1-yl)-2-mercapto-1H-benzimidazole (2.5 g,10.0 mmol) (obtained in preparation 16),4-methoxy-3-methyl-2-chloromethylpyridine hydrochloride (2.4 g, 11.0 mmol), sodium hydroxide (0.8 g, 20.0 mmol) and ethanol (30 mL). mp 210–211° C.; IR (KBr) 3340, 1581, 1479 cm$^{-1}$; $^1$H NMR (CDCl$_3$) δ 1.56 (m, 2H, CH$_2$), 1.74 (m, 4H, (CH$_2$)$_2$), 2.22 (s,3H, CH$_3$), 3.10 (t,J=5.4 Hz, 4H, N(CH$_2$)$_2$), 3.86 (s, 3H, OCH$_3$), 4.36 (s, 2H, SCH$_2$), 6.72 (d,J=5.9 Hz, 1H), 6.96 (d,J=11.2 Hz, 1H), 7.10 (s, 1H), 7.44 (d,J=9.8 Hz, 1H), 8.36 (d,J=5.8 Hz, 1H); Mass (m/z) 368 (M$^+$).

EXAMPLE 40

2-[[(4-Methoxy-3-methyl)pyridin-2-yl]methylthiol-]-5-(hexamethyleneimin-1-yl)-1H-benzimidazole:

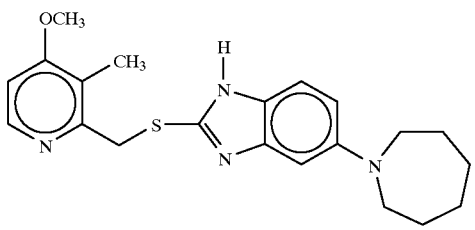

The title compound (0.9 g, 39%) was prepared by the general procedure using 5-(hexamethyleneimin-1-yl)-2-mercapto-1H-benzimidazole (1.5 g, 6.1 mmol) (obtained in preparation 17), 4-methoxy-3-methyl-2-chloromethylpyridine hydrochloride (1.3 g, 6.1 mmol), sodium hydroxide (0.48 g, 12.2 mmol) and ethanol (20 mL). mp 151–152° C.; IR (KBr) 3338, 1528, 1452 cm$^{-1}$; $^1$H NMR (CDCl$_3$) δ 1.54 (m, 4H, (CH$_2$)$_2$), 1.82 (m, 4H, (CH$_2$)$_2$), 2.24 (s, 3H, CH$_3$), 3.50 (t,J=5.8 Hz, 4H, N(CH$_2$)$_2$), 3.88 (s, 3H, OCH$_3$), 4.34 (s, 2H, SCH$_2$), 6.66 (d,J=11.2Hz, 1H), 6.72 (d,J=5.4 Hz, 1H), 6.76 (s, 1H), 7.36 (d,J=9.0Hz, 1H), 8.36 (d,J=5.8 Hz, 1H); Mass (m/z) 382 (M$^+$).

EXAMPLE 41

2-[[(4-Methoxy-3-methyl)pyridin-2-yl]methylthio]-4,6-difluoro-5-(morpholin-1-yl)-1H-benzimidazole:

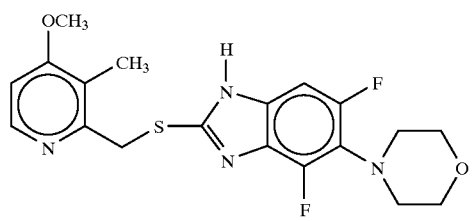

The title compound (1.1 g, 73%) was prepared by the general procedure using 4,6-difluoro-5-(morpholin-1-yl)-2-mercapto-1H-benzimidazole (1.0 g, 3.7 mmol) (obtained in preparation 18), 4-methoxy-3)-methyl-2-chloromethylpyridine hydrochloride (0.92 g, 4.4 mmol), sodium hydroxide (0.3 g, 7.4 mmol) and ethanol (20 mL). mp 138–139° C.; IR (KBr) 3268, 1438 cm$^{-1}$; $^1$H NMR (CDCl$_3$) δ 2.28 (s, 3H, CH$_3$), 3.20 (m, 4H, N(CH$_2$)$_2$), 3.84 (m, 4H, O(CH$_2$)$_2$), 3.90 (s, 3H, OCH$_3$), 4.36 (s, 2H, SCH$_2$), 6.78 (d,J=4.8 Hz, 1H), 7.04 (d,J=9.7 Hz, 1H), 8.34 (d, J=5.7 Hz, 1H); Mass (m/z) 406 (M$^+$).

EXAMPLE 42

2-[[(4-Methoxy-3,5-dimethyl)pyridin-2-yl]methylthio]-4,6-difluoro-5-(4-methylpiperazin-1-yl)-1H-benzimidazole:

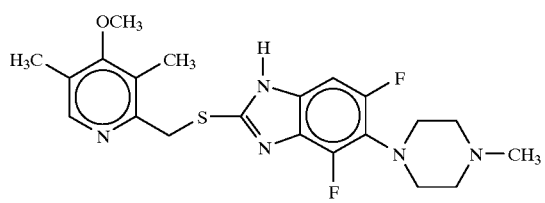

The title compound (0.8 g, 87%) was prepared by the general procedure using 4,6-difluoro-5-(4-methylpiperazin-1-yl)-2-mercapto-1H-benzimidazole (0.60 g, 2.1 mmol) (obtained in preparation 19), 4-methoxy-3,5-dimethyl-2-chloromethylpyridine hydrochloride (0.47 g, 2.5 mmol), sodium hydroxide (0.17 g, 4.2 mmol) and ethanol (10 mL). mp 176–177° C.; IR (KBr) 3320, 1582, 1438 cm$^{-1}$; $^1$H NMR (DMSO-d$_6$) δ 2.08 (s, 3H, CH$_3$), 2.12 (s, 3H, CH$_3$), 2.22 (s, 31H, CH$_3$), 2.42 (m,4H, N(CH$_2$)$_2$), 3.04 (m,4H, N(CH$_2$)$_2$), 3.66 (s, 3H, OCH$_3$), 4.62 (s, 2H, SCH$_2$), 7.08 (d,J=7.6 Hz, 1Hz), 8.12 (s, 1H), 12.70 (brs, 1H, NH); Mass (m/z) 433 (M$^{30}$.).

Preparation of Pyridylmethylsulfinyl benzimidazole derivatives and their sodium salts:

General procedure:

A solution of pyridylmethylthio benzimidazole derivative (1.0 eq) (see examples 1–42) in dichloromethane or chloroform (5.0 mL /1.0 mmol of substrate) was cooled to −40° to −50° C. A solution of m-chloroperbenzoic acid (50%, 0.9 to 1.5 eq) in dichloromethane or chloroform (1.0 mL /1.0 mmol of substrate) was cooled to −40° to −50° C. and added dropwise to the above solution. The reaction mixture was stirred for 0.5 to 5 h at the same temperature and quenched with triethylamine (1.5 to 2.0 eq). The mixture was slowly warmed to −10° C., followed by the addition of an aqueous solution of sodium carbonate and stirred for 30 minutes. The mixture was extracted with chloroform and the extracts were washed with brine; dried over anhydrous sodium sulfate and the solvent was removed under reduced pressure. The residue was purified by column chromatography over alumina using a mixture of methanol—ethyl acetate (1:9 to 4:1) as eluent. The syrupy oil was crystallised from diethyl ether or acetone to obtain the title compound.

To the compound obtained above (1.0 eq) was added 0.1N NaOH solution (1.0 eq) and stirred for 1 h at ca 30° C. Ethanol was added and distilled to remove water as an azeotropic mixture with ethanol under reduced pressure. The residue obtained was crystallised from diethyl ether or acetone.

Following compounds (Examples 43–92 ) were prepared according to the general procedure described above.

EXAMPLE 43

2-[[(4-Methoxy-3,5-dimethyl)pyridin-2-yl]methylsulfinyl]-6-fluoro-5-(imidazol-1-yl)-1H-benzimidazole:

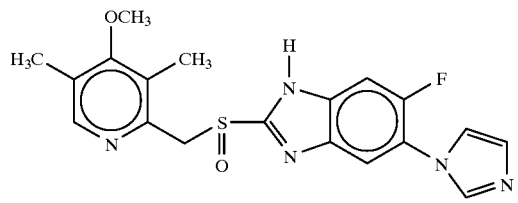

The title compound (0.24 g, 46%) was prepared according to the above general procedure using 2-[[(4-methoxy-3,5-dimethyl)pyridin-2-yl]methylthio]-6-fluoro-5-(imidazol-1-yl)-1H-benzimidazole (0.5 g, 1.3 mmol) (obtained in example 1), m-chloroperbenzoic acid (50%, 0.54 g, 1.56 mmol) and chloroform (30 mL). mp 190–191° C.; IR (KBr) 3440, 1044 cm$^{-1}$; $^1$H NMR (DMSO-d$_6$) δ 2.20 (s, 6H, 2×CH$_3$), 3.80 (s, 3H, OCH$_3$), 4.80 (s, 2H, SOCH$_2$), 7.18 (s, 1H), 7.60 (s, 1H), 7.80 (d,J=9.6 Hz, 1H), 7.90 (d,J=7.8 Hz, 1H), 8.08 (s, 1H), 8.20 (s, 1H); Mass (m/z) 399 (M$^+$.).

EXAMPLE 44

2-[[(4-Methoxy-3,5-dimethyl)pyridin-2-yl]methylsulfinyl]-6-fluoro-5-(imidazol-1-yl)-1H-benzimidazole, sodium salt:

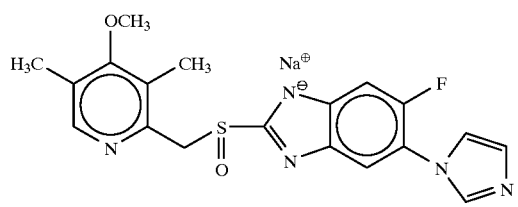

The title compound (0.04 g, 95%) was prepared by the above general procedure using 2-[[(4-methoxy-3,5-dimethyl)pyridin-2-yl]methylsulfinyl]-6-fluoro-5-(imidazol-1-yl)- 1H-benzimidazole (0.04 g, 0.1 mmol) (obtained in example 43) and 0.1N NaOH solution (1.0 mL, 0.1 mmol). mp 239–240° C.; IR (KBr) 1440, 1040 cm$^{-1}$; $^1$H NMR (CD$_3$OD) δ 2.12 (s, 3H, CH$_3$), 2.30 (s, 3H, CH$_3$), 3.70 (s, 3H, OCH$_3$), 4.90 (s, 2H, SOCH$_2$), 7.18 (s, 1H), 7.40 (s, 1H), 7.50 (d,J=10.8 Hz, 1H), 7.70 (d,J=7.6 Hz, 1H), 7.90 (s, 1H), 8.20 (s, 1H).

EXAMPLE 45

2-[[(4-Methoxy-3,5-dimethyl)pyridin-2-yl]methylsulfonyl]-6-fluoro-5-(imidazol-1-yl)-1H-benzimidazole:

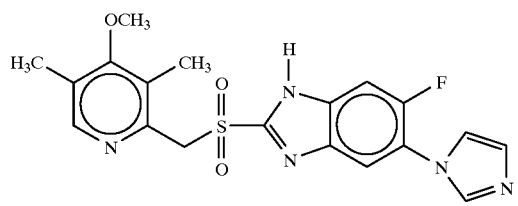

The title compound (0.22 g, 53%) was prepared by the above general procedure using 2-[[(4-methoxy-3,5- dimethyl)pyridin-2-yl]methylthio]-6-fluoro-5-(imidazol-1-yl)-1H-benzimidazole (0.38 g, 1.0 mmol) (obtained in example 1), m-chloroperbenzoic acid (50%, 1.0 g, 3.0 mmol) and chloroform (20 mL). mp 160–161° C.; IR (KBr) 3434, 1136 cm$^{-1}$; $^1$H NMR (DMSO-d$_6$) δ 2.18 (s, 3H, CH$_3$), 2.24 (s, 3H, CH$_3$), 3.74 (s, 3H, OCH$_3$), 5.38 (s, 2H, SO$_2$CH$_2$), 7.10 (s, 1H), 7.54 (s,1H), 7.68 (d,J=10.2 Hz, 1H), 7.86 (d,J=7.6 Hz, 1H), 8.00 (s,1H), 8.10 (s, 1H); Mass (m/z) 383 (M −32).

EXAMPLE 46

2-[[3-Methyl-4-(2,2,2-trifluoroethoxy)pyridin-2-yl] methylsulfinyl]-6-fluoro-5-(imidazol-1-yl)-1H-benzimidazole:

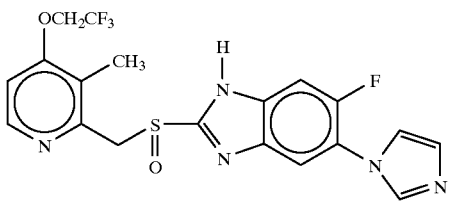

The title compound (0.24 g, 45%) was prepared by the above general procedure using 2-[[3-methyl-4-(2,2,2-trifluoroethoxy)pyridin-2-yl]methylthio]-6-fluoro-5-(imidazol-1-yl)-1H-benzimidazole (0.5 g, 1.14 mmol) (obtained in example 2), m-chloroperbenzoic acid (50%, 0.47 g, 1.4 mmol) and dichloromethane (10 mL). mp 234–235° C.; IR (KBr) 3449, 1049 cm$^{-1}$; $^1$H NMR (CD$_3$OD+CDCl$_3$) δ 2.28 (s, 3H, CH$_3$), 4.42 (q,J=6.3 Hz, 2H, OCH$_2$CF$_3$), 4.74 (ABq, J=9.6 Hz, Δv=6.2 Hz, 2H, SOCH$_2$), 6.74 (d,J=5.6 Hz, 1H), 7.20 (m, 2H), 7.52 (d,J=10.8 Hz, 1H), 7.70 (d,J=7.6 Hz, 1H), 7.86 (s, 1H), 8.30 (d,J=5.6 Hz, 1H); Mass (m/z) 453 (M$^+$).

EXAMPLE 47

2-[[3-Methyl-4-(2,2,2-trifluoroethoxy)pyridin-2-yl] methylsulfinyl]-6-fluoro-5-(imidazol-1-yl)-1H-benzimidazole, sodium salt:

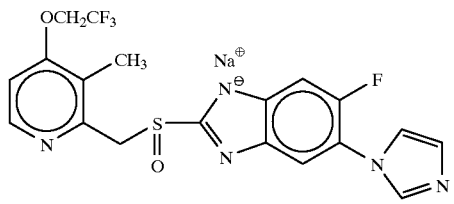

The title compound (0.04 g, 88%) was prepared by the above general procedure using 2-[[3-methyl-4-(2,2,2-trifluoroethoxy)pyridin-2-yl]methylsulfinyl]-6-fluoro-5-(imidazol-1-yl)-1H-benzimidazole (0.045 g, 0.1 mmol) (obtained in example 46) and 0.1N NaOH solution (1.0 mL, 0.1 mmol). mp 240–241° C.; IR (KBr) 1466, 1040 cm$^{-1}$; $^1$H NMR (DMSO-d$_6$) δ 2.22 (s, 3H, CH$_3$), 4.60 (ABq,J=10.4 Hz, Δv=54.0 Hz, 2H, SOCH$_2$), 4.90 (q,J=5.8 Hz, 2H, OCH$_2$CF$_3$), 7.08 (m, 2H), 7.40 (d,J=8.2 Hz, 1H), 7.46 (s, 1H), 7.68 (d,J=6.7 Hz, 1H), 7.90 (s, 1H), 8.38 (d,J=5.4 Hz, 1H).

EXAMPLE 48

2-[[(4-Methoxy-3-methyl)pyridin-2-yl]methylsulfinyl]-6-fluoro-5-(imidazol-1-yl)-1H-benzimidazole:

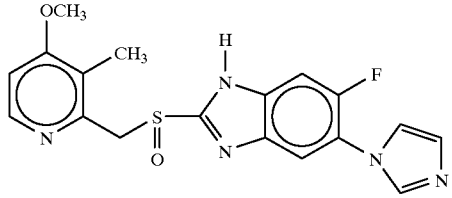

The title compound (0.1 g, 64%) was prepared by the above general procedure using 2-[[(4-methoxy-3-methyl) pyridin-2-yl]methylthio]-6-fluoro-5-(imidazol-1-yl)-1H-benzimidazole (0.15 g, 0.4 mmol) (obtained in example 3), m-chloroperbenzoic acid (50%, 0.17 g, 0.48 mmol) and dichloromethane (10 mL). mp208–209° C.; IR (KBr) 3450, 1049 cm$^{-1}$; $^1$H NMR (CD$_3$OD) δ 2.14 (s, 3H, CH$_3$), 3.88 (s, 3H, OCH$_3$), 4.80 (s, 2H, SOCH$_2$), 6.90 (d,J=5.8 Hz, 1H), 7.12 (s, 1H), 7.44 (s, 1H), 7.60 (d,J=10.3 Hz, 1H), 7.80 (d,J=7.6 Hz, 1H), 8.98 (s, 1H), 8.10 (d,J=5.7 Hz, 1H); Mass (m/z) 369 (M −16).

EXAMPLE 49

2-[[(4-(3-Methoxypropoxy)-3-methyl)pyridin-2-yl] methylsulfinyl]-6-fluoro-5-(imidazol-1-yl)-1H-benzimidazole:

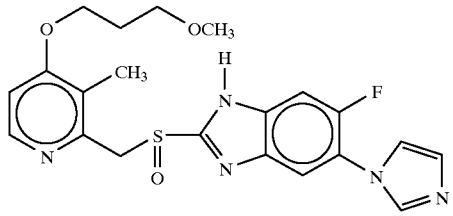

The title compound (0.093 g, 55%) was prepared by the above general procedure using 2-[[(4-(3-methoxypropoxy)-3-methyl-pyridin-2-yl]methylthio]-6-fluoro-5-(imidazol-1-yl)-1H-benzimidazole (0.15 g, 0.35 mmol) (obtained in example 4), m-chloroperbenzoic acid (50%, 0.15 g, 0.42 mmol) and dichloromethane (20 mL). mp 150–151° C.; IR (KBr) 3435, 1044 cm$^{-1}$; $^1$H NMR (CDCl$_3$) δ 2.10 (m, 2H, CH$_2$), 2.24 (s, 3H, CH$_3$), 3.38 (s, 3H, OCH$_3$), 3.56 (t,J=5.8 Hz, 2H, OCH$_2$), 4.10 (t,J=5.7 Hz, 2H, OCH$_2$), 4.80 (ABq, J=10.6 Hz, Δv=18.2 Hz, 2H, SOCH$_2$), 6.74 (d,J=6.1 Hz, 1H), 7.24 (m, 2H), 7.50 (d,J=10.8 Hz, 1H), 7.68 (d,J=7.6 Hz, 1H), 7.82 (s, 1H), 8.28 (d,J=6.0 Hz, 1H); Mass (m/z) 427 (M −16)

EXAMPLE 50

2-[[(4-Methoxy)pyridin-2-yl]methylsulfinyl]-6-fluoro-5-(imidazol-1-yl)-1H-benzimidazole:

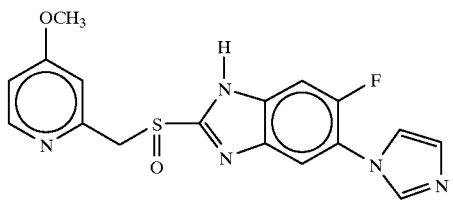

The title compound (0.32 g, 58%) was prepared by the above general procedure using 2-[[(4-methoxy)pyridin-2-yl]

methylthio]-6-fluoro-5-(imidazol-1-yl)-1H-benzimidazole (0.53 g, 1.5 mmol) (obtained in example 5), m-chloroperbenzoic acid (50%, 0.62 g, 1.8 mmol) and dichloromethane (20 mL). IR (KBr) 3500, 1048 cm$^{-1}$; $^{1}$H NMR (CD$_3$OD) δ 3.86 (s, 3H, OCH$_3$), 4.72 (ABq,J=10.8 Hz, Δv=15.6 Hz, 2H, SOCH$_2$), 6.94 (m, 2H), 7.22 (s, 1H), 7.52 (s, 1H), 7.68 (d,J=10.8 Hz, 1H), 7.88 (d,J=7.6 Hz, 1H), 8.08 (s, 1H), 8.26 (d,J=5.6 Hz, 1H); Mass (m/z) 371 (M$^+$.).

EXAMPLE 51

2-[[(4-Methoxy)pyridin-2-yl]methylsulfinyl]-6-fluoro-5-(imidazol-1-yl)-1H-benzimidazole, sodium salt:

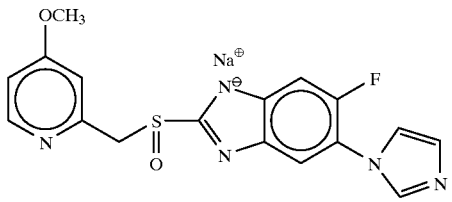

The title compound (0.04 g, 78%) was prepared by the above general procedure using 2-[[(4-methoxy)pyridin-2-yl]methylsulfinyl]-6-fluoro-5-(imidazol-1-yl)-1H-benzimidazole (0.05 g, 0.13 mmol) (obtained in example 50) and 0.1N NaOH solution (1.3 mL, 0.13 mmol). mp 142–143° C.; IR (KBr) 1601, 1038 cm$^{-1}$; $^{1}$H NMR (CD$_3$OD) δ 3.64, (s, 3H, OCH$_3$), 4.90 (ABq,J=10.0 Hz, Δv=14.0 Hz, 2H, SOCH$_2$), 6.60 (s, 1H), 6.89 (d,J=5.6 Hz, 1H), 7.20 (s, 1H), 7.40 (s, 1H), 7.50 (d,J=10.8 Hz, 1H), 7.70 (d,J=7.6 Hz, 1H), 7.98 (s, 1H), 8.32 (d,J=7.6 Hz, 1H).

EXAMPLE 52

2-[[(4-Chloro-3-methyl)pyridin-2-yl]methylsulfinyl]-6-fluoro-5-(imidazol-1-yl)-1H-benzimidazole:

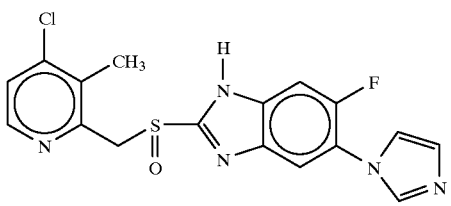

The title compound (0.3 g, 50%) was prepared by the above general procedure using 2-[[(4-chloro-3-methyl)pyridin-2-yl]methylthio-6-fluoro-5-(imidazol-1-yl)-1H-benzimidazole (0.37 g, 1.0 mmol) (obtained in example 6), m-chloroperbenzoic acid (50%, 0.4 g, 1.2 mmol) and dichloromethane (20 mL). mp 58–60° C.; IR (KBr) 3429, 1044 cm$^{-1}$; $^{1}$H NMR (CDCl$_3$) δ 2.40 (s, 3H, CH$_3$), 4.88 (ABq, J=10.2 Hz, Δv=19.6 Hz, 2H, SOCH$_2$), 7.26 (m, 3H), 7.56 (d,J=8.2 Hz, 1H), 7.68 (d,J=6.0 Hz, 1H), 7.90 (s, 1H), 8.20 (d,J=5.8 Hz, 1H); Mass (m/z) 373 (M –16).

EXAMPLE 53

2-[[(4-Methoxy-3,5-dimethyl)pyridin-2-yl]methylsulfinyl]-6-fluoro-5-(morpholin-1-yl)-1H-benzimidazole:

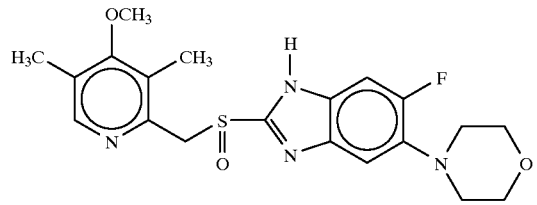

The title compound (0.2 g, 40%) was prepared by the above general procedure using 2-[[(4-methoxy-3,5-dimethyl)pyridin-2-yl]methylthio]-6-fluoro-5-(morpholin-1-yl)-1H-benzimidazole (0.5 g, 1.24 mmol) (obtained in example 7), m-chloroperbenzoic acid (50%, 0.52 g, 1.5 mmol) and chloroform (20 mL). mp 179–180° C.; IR (KBr) 3431, 1042 cm$^{-1}$; $^{1}$H NMR (CDCl$_3$) δ 2.20 (s, 3H, CH$_3$), 2.28 (s, 3H, CH$_3$), 3.18 (m, 4H, N(CH$_2$)$_2$), 3.72 (s, 3H, OCH$_3$), 3.98 (m, 4H, O(CH$_2$)$_2$), 4.78 (ABq,J=10.0 Hz, Δv=8.0 Hz, 2H, SOCH$_2$), 7.18 (d,J=8.2 Hz, 1H), 7.26 (d, J=10.6 Hz, 1H), 8.24 (s, 1H), 12.20 (brs, 1H, NH); Mass (m/z) 402 (M –16).

EXAMPLE 54

2-[[(4-Methoxy-3,5-dimethyl)pyridin-2-yl]methylsulfinyl]-6-fluoro-5-(morpholin-1-yl)-1H-benzimidazole, sodium salt:

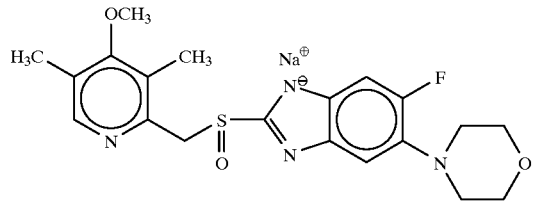

The title compound (0.04 g, 90%) was prepared by the above general procedure using 2-[[(4-methoxy-3,5-dimethyl)pyridin-2-yl]methylsulfinyl]-6-fluoro-5-(morpholin-1-yl)-1H-benzimidazole (0.04 g, 0.1 mmol) (obtained in example 53) and 0.1N NaOH solution (1.0 mL, 0.1 mmol). mp 184–185° C.; IR (KBr) 1489, 1075 cm$^{-1}$; $^{1}$H NMR (DMSO-d$_6$) δ 2.22 (s, 6H, 2×CH$_3$), 3.00 (m, 4H, N(CH$_2$)$_2$), 3.72 (s, 3H, OCH$_3$), 3.80 (m, 4H, O(CH$_2$)$_2$), 4.58 (ABq,J =10.6 Hz, Δv=54.0 Hz, 2H, SOCH$_2$), 7.10 (d,J=7.6 Hz, 1H), 7.20 (d,J=10.3 Hz, 1H), 8.25 (s, 1H).

EXAMPLE 55

2-[[3-Methyl-4-(2,2,2-trifluoroethoxy)pyridin-2-yl]methylsulfinyl]-6-fluoro-5-(morpholin-1-yl)-1H-benzimidazole:

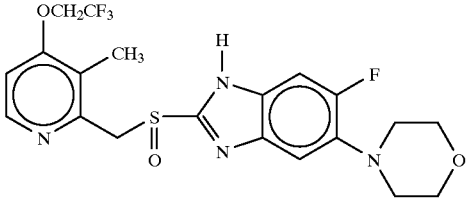

The title compound (0.2 g, 42%) was prepared by the above general procedure using 2-[[3-methyl-4-(2,2,2- trifluoroethoxy)pyridin-2-yl]methylthio]-6-fluoro-5-(morpholin-1-yl)-1H-benzimidazole (0.5 g, 1.0 mmol) (obtained in example 8), m-chloroperbenzoic acid (50%, 0.45 g, 1.3 mmol) and chloroform (20 mL). mp 104–105° C.; IR (KBr) 3417, 1070 cm$^{-1}$; $^1$H NMR (CDCl$_3$) δ 2.20 (s, 3H, CH$_3$), 3.08 (m, 4H, N(CH$_2$)$_2$), 3.92 (m, 4H, O(CH$_2$)$_2$), 4.40 (q, J=6.1 Hz, 2H, OCH$_2$CF$_3$), 4.80 (ABq,J=10.2 Hz, Δv=6.0 Hz, 2H, SOCH$_2$), 6.72 (d,J=5.6 Hz, 1H), 7.18 (d,J=8.0 Hz, 1H), 7.28 (d,J=9.6 Hz, 1H), 8.38 (d,J=5.7 Hz, 1H), 12.00 (brs, 1H, NH); Mass (m/z) 472 (M$^+$.).

EXAMPLE 56

2-[[3-Methyl-4-(2,2,2-trifluoroethoxy)pyridin-2-yl]methylsulfinyl]-6-fluoro-5-(morpholin-1-yl)-1H-benzimidazole, sodium salt:

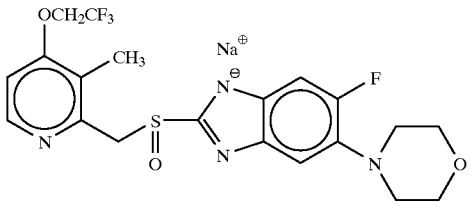

The title compound (0.04 g, 82%) was prepared by the above general procedure using 2-[[3-methyl-4-(2,2,2-trifluoroethoxy)pyridin-2-yl]methylsulfnyl]-6-fluoro-5-(morpholin-1-yl)-1H-benzimidazole (0.047 g, 0.1 mmol) (obtained in example 55) and 0.1N NaOH solution (1.0 mL, 0.mmol). mp 141–142° C.; IR (KBr) 1452, 1021 cm$^{-1}$; $^1$H NMR (DMSO-d$_6$) δ 2.28 (s, 3H, CH$_3$), 3.00 (m, 4H, N(CH$_2$)$_2$), 3.82 (m, 4H, O(CH$_2$)$_2$), 4.60 (ABq,J=10.0 Hz, Δv=54.0 Hz, 2H, SOCH$_2$), 4.92 (q,J=5.6 Hz, 2H, OCH$_2$CF$_3$), 7.06 (d,J=5.2 Hz, 1H), 7.12 (d,J=7.6 Hz, 1H), 7.22 (d,J=9.8 Hz, 1H), 8.32 (d,J=5.4 Hz, 1H).

EXAMPLE 57

2-[[(4-Methoxy-3-methyl)pyridin-2-yl]methylsulfinyl]-6-fluoro-5-(morpholin-1-yl)-1H-benzimidazole:

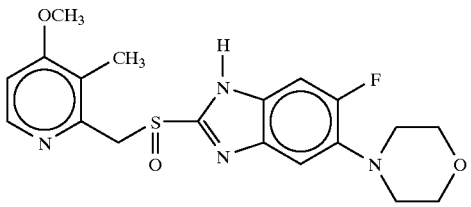

The title compound (0.18 g, 60%) was prepared by the above general procedure using 2-[[(4-methoxy-3-methyl)pyridin-2-yl]methylthio]-6-fluoro-5 -(morpholin-1-yl)-1H-benzimidazole (0.29 g, 0.75 mmol) (obtained in example 9), m-chloroperbenzoic acid (50%, 0.31 g, 0.9 mmol) and dichloromethane (25 mL). mp 183–184° C.; IR (KBr) 3431, 1044cm$^{-1}$; $^1$H NMR (CDCl$_3$) δ 2.20 (s, 3H, CH$_3$), 3.12 (m, 4H, N(CH$_2$)$_2$), 3.80 (s, 3H, OCH$_3$), 3.98 (m, 4H, O(CH$_2$)$_2$), 4.80 (ABq,J=10.2 Hz, Δv=12.6 Hz, 2H, SOCH$_2$), 6.78 (d,J=5.4 Hz, 1H), 7.22 (d,J=7.6 Hz, 1H), 7.34 (d,J=9.8 Hz, 1H), 8.38 (d,J=5.6 Hz, 1H), 12.20 (brs, 1H, NH); Mass (m/z) 404 (M$^+$.).

EXAMPLE 58

2-[[(4-Methoxy-3-methyl)pyridin-2-yl]methylsulfinyl]-6-fluoro-5-(morpholin-1-yl)-1H-benzimidazole, sodium salt:

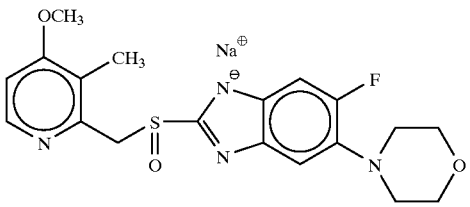

The title compound (0.05 g, 78%) was prepared by the above general procedure using 2-[[(4-methoxy-3-methyl)pyridin-2-yl]methylsulfinyl]-6-fluoro-5-(morpholin-1-yl)-1H-benzimidazole (0.06 g, 0.15 mmol) (obtained in example 57) and 0.1N NaOH solution (1.5 mL, 0.15 mmol). mp 270–271° C.; IR (KBr) 1451, 1040 cm$^{-1}$; $^1$H NMR (DMSO-d$_6$) δ 2.18 (s, 3H, CH$_3$), 2.90 (m, 4H, N(CH$_2$)$_2$), 3.74 (m, 4H, O(CH$_2$)$_2$), 3.88 (s, 3H, OCH$_3$), 4.90 (ABq,J=10.0 Hz, Δv=48.0 Hz, 2H, SOCH$_2$), 6.92 (d,J=5.6 Hz, 1H), 7.10 (d,J=7.6 Hz, 1H), 7.18 (d,J=9.5 Hz, 1H), 8.32 (d,J5.4 Hz, 1H).

EXAMPLE 59

2-[[(4-(3-Methoxypropoxy)-3-methyl)pyridin-2-yl]methylsulfinyl]-6-fluoro-5-(morpholin-1-yl)-1H-benzimidazole:

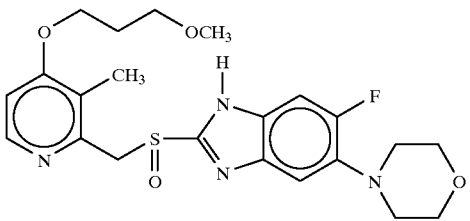

The title compound (0.06 g, 56%) was prepared by the above general procedure using 2-[[(4-(3-methoxypropoxy)-3 -methyl)pyridin-2-yl]methylthio]-6-fluoro-5-(morpholin-1-yl)-1H-benzimidazole (0.1 g, 0.23 mmol) (obtained in example 10), m-chloroperbenzoic acid (50%, 0.1 g, 0.27 mmol) and chloroform (10 mL). mp 158–159° C.; IR (KBr) 3429, 1020 cm$^{-1}$; $^1$H NMR (CD$_3$OD) δ 2.08 (m, 2H, CH$_2$), 2.20 (s, 3H, CH$_3$), 3.10 (m, 4H, N(CH$_2$)$_2$), 3.32 (s, 3H, OCH$_3$),3.58 (t,J=4.6 Hz, 2H, OCH$_2$), 4.88 (m, 4H, O(CH$_2$)$_2$), 4.16 (t,J=4.6 Hz, 2H, OCH$_2$), 5.18 (ABq,J=10.0 Hz, Δv=12.0 Hz, 2H, SOCH$_2$), 6.92 (d,J=5.6 Hz, 1H), 7.20 (d,J=7.2 Hz, 1H), 7.40 (d,J=9.8 Hz, 1H), 8.00 (d,J=5.4 Hz, 1H); Mass (m/z) 462 (M$^+$).

EXAMPLE 60

2-[[4-(Morpholin-1-yl)-3-methylpyridin-2-yl]methylsulfinyl]-6-fluoro-5-(morpholin-1-yl)-1H-benzimidazole:

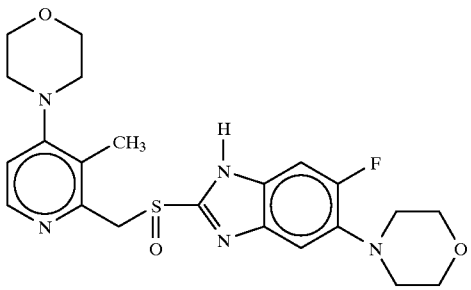

The title compound (0.13 g, 36%) was prepared by the above general procedure using 2-[[(4-morpholin-1-yl)-3-methylpyridin-2-yl]methylthio]-6-fluoro-5-(morpholin-1-yl)-1H-benzimidazole (0.35 g, 0.8 mmol) (obtained in example 11), m-chloroperbenzoic acid (50% 0.21 g, 0.63 mmol) and dichloromethane (20 mL). mp 102–103° C.; IR (KBr) 3436, 1580, 1018 cm$^{-1}$; $^1$HNMR (CDCl$_3$) δ 2.24 (s, 3H, CH$_3$), 2.90 (t,J=4.3 Hz, 4H, N(CH$_2$)$_2$), 3.08 (t, J=4.4 Hz, 4H, N(CH$_2$)$_2$), 3.82 (t,J=4.3 Hz, 4H, (OCH$_2$)$_2$), 3.92 (t,J=4.2 Hz, 4H, O(CH$_2$)$_2$), 4.70 (ABq,J=14.0 Hz, Δν=12.6 Hz, 2H, SOCH$_2$), 6.82 (d,J=5.5 Hz, 1H), 7.16 (d,J=6.7 Hz, 1H), 7.32 (d,J=12.1 Hz, 1H), 8.32 (d,J=5.4 Hz, 1H); Mass (m/z) 443 (M −16).

EXAMPLE 61

2-[[4-(Morpholin-1-yl)-3-methylpyridin-2-yl]methylsulfinyl]-6-fluoro-5-(morpholin-1-yl)-1H-benzimidazole, sodium salt:

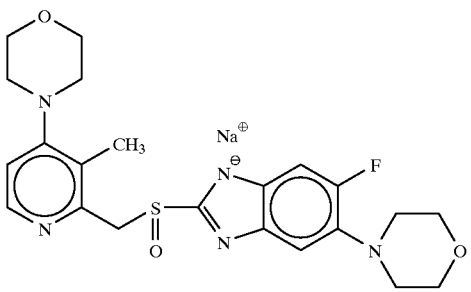

The title compound was prepared by the above general procedure using 2-[[4-(morpholin-1-yl)-3-methylpyridin-2-yl]methylsulfinyl]-6-fluoro-5-(morpholin-1-yl)-1H-benzimidazole (0.04 g, 0.8 mmol) (obtained in example 60) and 0.1N NaOH solution (0.8 mL, 0.08 mmol). mp 229–230° C.; IR (KBr) 1582, 1032 cm$^{-1}$; $^1$H NMR (DMSO-d$_6$) δ 2.26 (s, 3H, CH$_3$), 2.90 (m, 8H, 2×N(CH$_2$)$_2$), 3.80 (m, 8H, 2×O(CH$_2$)2), 4.60 (ABq,J=9.8 Hz, Δν=60.0 Hz, 2H, SOCH$_2$), 6.72 (d,J=5.4Hz, 1H), 7.12 (d,J=7.2Hz, 1H), 7.18 (d,J=10.4Hz, 1H), 8.30 (d,J=5.3 Hz, 1H).

EXAMPLE 62

2-[(4-(Piperidin-1-yl)-3-methylpyridin-2-yl)methylsulfinyl]-6-fluoro-5-(morpholin-1-yl)-1H-benzimidazole:

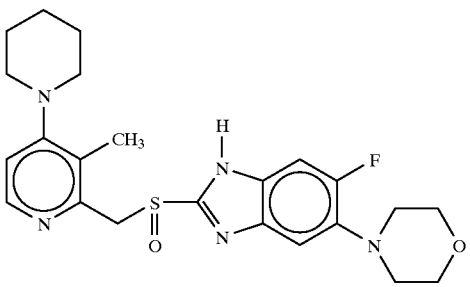

The title compound (0.1 g, 22%) was prepared by the above general procedure using 2-[[4-(piperidin-1-yl)-3-methylpyridin-2-yl]methylthio]-6-fluoro-5-(morpholin-1-yl)-1H-benzimidazole (0.44 g, 1.0 mmol) (obtained in example 12), m-chloroperbenzoic acid (50%, 0.4 g, 1.1 mmol) and dichloromethane (10 mL). mp 116–117° C.; IR (KBr) 3422, 1580, 1041 cm$^{-1}$; $^1$H NMR (CDCl$_3$) δ 1.50–1.75 (m, 6H, (CH$_2$)$_3$), 2.19 (s, 3H, CH$_3$), 2.82 (t,J=5.2 Hz, 4H, N(CH$_2$)$_2$), 3.08 (t,J=4.3 Hz, 4H, N(CH$_2$)$_2$), 3.90 (t,J=4.4 Hz, 4H, N(CH$_2$)$_2$), 4.76 (ABq,J=9.5 Hz, Δν=15.9 Hz, 2H, SOCH$_2$), 6.78 (d,J=5.4 Hz, 1H), 7.14 (d,J=7.6 Hz, 1H), 7.28 (d, J=12.0 Hz, 1H), 8.24 (d,J=5.4 Hz, 1H); Mass (m/z) 457 (M$^+$.).

EXAMPLE 63

2-[[(3-Methyl)pyridin-2-yl]methylsulfinyl]-6-fluoro-5-(morpholin-1-yl)-1H-benzimidazole:

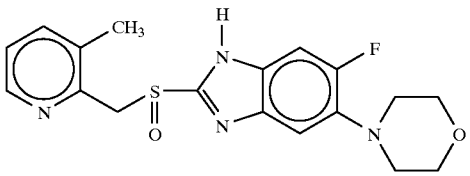

The title compound (0.2 g, 80%) was prepared by the above general procedure using 2-[[(3-methyl)pyridin-2-yl]methylthio]-6-fluoro-5-(morpholin-1-yl)-1H-benzimidazole (0.2 g, 0.55 mmol) (obtained in example 14), m-chloroperbenzoic acid (50%, 0.2 g, 0.5 mmol) and dichloromethane (10 mL). mp 158–159° C.; IR (KBr) 3437, 1449, 1046 cm$^{-1}$; $^1$H NMR (CDCl$_3$) δ 2.36 (s, 3H, CH$_3$),3.10 (t,J=4.6Hz, 4H, N(CH$_2$)$_2$),3.92 (t,J=4.6 Hz, 4H, O(CH$_2$)$_2$), 4.70 (ABq,J=13.8 Hz, Δν=23.1 Hz, 2H, SOCH$_2$), 7.28–7.32 (m, 3H), 7.52 (d,J=7.4 Hz, 1H), 8.42 (d,J=4.4 Hz, 1H), 11.40 (brs, 1H, NH); Mass (m/z) 374 (M+.).

EXAMPLE 64

2-[[(4-Methoxy-3,5-dimethyl)pyridin-2-yl]methylsulfinyl]-6-fluoro-5-(piperidin-1-yl)-1H-benzimidazole:

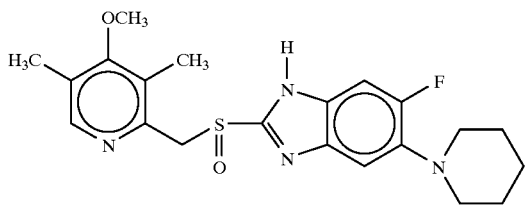

The title compound (0.2 g, 77%) was prepared by the above general procedure using 2-[[(4-methoxy-3,5-dimethyl)pyridin-2-yl]methylthio]-6-fluoro-5-(piperidin-1-yl)-1H-benzimidazole (0.2 g, 0.5 mmol) (obtained in example 15), m-chloroperbenzoic acid (50%, 0.2 g, 0.6 mmol) and chloroform (20 mL). mp 95–96° C.; IR (KBr) 3422, 1077 cm$^{-1}$; $^1$H NMR (DMSO-d$_6$) δ 1.58 (m, 2H, CH$_2$), 1.70 (m, 4H, (CH$_2$)$_2$), 2.18 (s, 3H, CH$_3$), 2.22 (s, 3H, CH$_3$), 3.00 (m, 4H, N(CH$_2$)$_2$), 3.70 (s, 3H, OCH$_3$), 4.76 (ABq,J=13.3 Hz, Δv=15.2 Hz, 2H, SOCH$_2$), 7.20 (d, J=8.0 Hz, 1H), 7.46 (d,J12.4 Hz, 1H), 8.20 (s, 1H); Mass (m/z) 416 (M$^+$).

EXAMPLE 65

2-[[(4-Methoxy-3,5-dimethyl)pyridin-2-yl]methylsulfinyl]-6-fluoro-5-(piperidin-1-yl)-1H-benzimidazole, sodium salt:

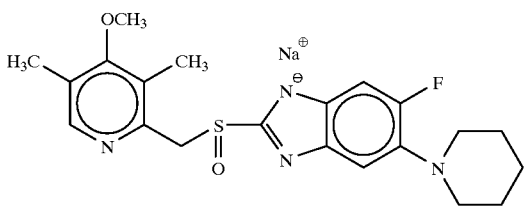

The title compound (0.07 g, 95%) was prepared by the above general procedure using 2-[[4-methoxy-3,5-dimethylpyridin-2-yl]methylsulfinyl]-6-fluoro-5-(piperidin-1-yl)-1H-benzimidazole, (0.07 g, 0.17 mmol) (obtained in example 64), 0.1N NaOH solution (1.7 mL, 0.17 mmol). IR (KBr) 1470, 1027 cm$^{-1}$; $^1$H NMR (DMSO-d$_6$) δ 1.56 (m, 2H, CH$_2$), 1.70 (m, 4H, (CH$_2$)$_2$), 2.24 (s, 3H, CH$_3$), 2.92 (s, 3H, CH$_3$), 3.46 (m, 4H, N(CH$_2$)$_2$), 3.72 (s, 3H, OCH$_3$), 4.54 (ABq,J=13.0 Hz, Δv=50.0 Hz,2H, SOCH$_2$), 7.12 (d,J=5.0Hz, 1H), 7.16 (d,J=8.4 Hz, 1H), 8.26 (s, 1H).

EXAMPLE 66

2-[[3-Methyl-4-(2,2,2-trifluoroethoxy)pyridin-2-yl]methylsulfinyl]-6-fluoro-5-(piperidin-1-yl)-1H-benzimidazole:

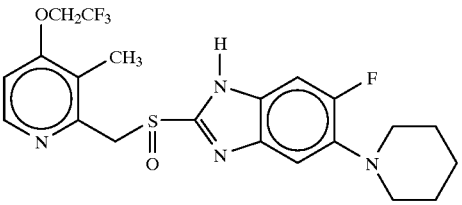

The title compound (0.18 g, 78%) was prepared by the above general procedure using 2-[[3-methyl-4-(2,2,2-trifluoroethoxy)pyridin-2-yl]methylthio]-6-fluoro-5-(piperidin-1-yl)-1H-benzimidazole (0.23 g, 0.5 mmol) (obtained in example 16), m-chloroperbenzoic acid (50%, 0.2 g, 0.6 mmol) and chloroform (20 mL). mp 99–100° C.; IR (KBr) 3413, 1070 cm$^{-1}$; $^1$H NMR (DMSO-d$_6$) δ 1.52 (m, 2H, CH$_2$), 1.70 (m, 4H, (CH$_2$)$_2$), 2.20 (s, 3H, CH$_3$) 3.98 (t,J=4.5 Hz, 4H, N(CH$_2$)$_2$), 4.80 (ABq,J=12.9 Hz, Δv=9.1 Hz, 2H, SOCH$_2$), 4.94 (q,J=8.1 Hz, 2H, OCH$_2$CF$_3$), 7.12 (d,J=5.8 Hz, 1H), 7.18 (d,J=7.8 Hz, 1H), 7.44 (d,J=12.7 Hz, 1H), 8.32 (d,J=5.5 Hz, 1H); Mass (m/z) 454 (M −16).

EXAMPLE 67

2-[[(4-Methoxy-3-methyl)pyridin-2-yl]methylsulfinyl]-6-fluoro-5-(piperidin-1-yl)-1H-benzimidazole:

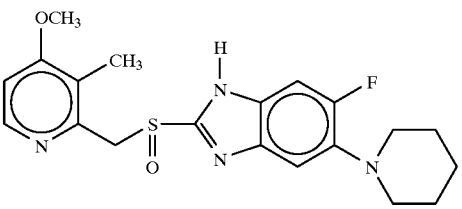

The title compound (0.1 g, 50%) was prepared by the above general procedure using 2-[[(4-methoxy-3-methyl)pyridin-2-yl]methylthlo]-6-fluoro-5-(piperidin-1-yl)-1H-benzimidazole(0.19 g, 0.5 mmol) (obtained in example 17), m-chloroperbenzoic acid (50%, 0.2 g, 0.6 mmol) and chloroform (20 mL). mp 168–169° C.; IR (KBr) 3432, 1096 cm$^{-1}$; $^1$H NMR (CD$_3$OD) δ 1.60 (m, 2H, CH$_2$),1.80 (m, 4H, (CH$_2$)$_2$), 2.18 (s, 3H, CH$_3$), 3.00 (t,J=4.6 Hz, 4H, N(CH$_2$)$_2$), 3.80 (s, 3H, OCH$_3$), 4.80 (ABq,J=13.8 Hz, Δv=4.2 Hz, 2H, SOCH$_2$), 6.74 (d,J=5.7 Hz, 1H), 7.12 (d,J=7.6Hz, 1H), 7.28 (d,J=11.8 Hz, 1H), 8.32 (d,J=5.7 Hz, 1H); Mass (m/z) 402 (M$^+$).

EXAMPLE 68

2-[[(4-Methoxy-3-methyl)pyridin-2-yl]metlhylsulfinyl]-6-fluoro-5-(piperidin-1-yl)-1H-benzimidazole, sodium salt:

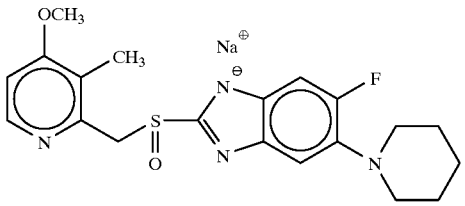

The title compound (0.02 g, 46%) was prepared by the above general procedure using 2-[[4-(methoxy-3-methyl) pyridin-2-yl]methylsulfinyl]-6-fluoro-5-(piperidin-1-yl)-1H-benzimidazole (0.04 g, 0.1 mmol) (obtained in example 67) and 0.1N NaOH solution (1.0 mL, 0.1 mmol). mp 164–165° C.; IR (KBr) 1583, 1022 cm$^{-1}$; $^1$H NMR (DMSO-d$_6$) δ 1.54 (m, 2H , CH$_2$), 1.68(m, 4H, (CH$_2$)$_2$), 2.16 (s,3H, CH$_3$), 2.90 (t,J=4.6 Hz, 4H,N(CH$_2$)$_2$),3.86(s, 3H, OCH$_3$), 4.60 (ABq, J=12.8 Hz, Δv=59.0 Hz, 2H, SOCH$_2$), 6.94 (d,J=5.4 Hz, 1H),7.10(d,J=8.7 Hz, 1H),7.20 (d,J=15.4 Hz, 1H), 8.28 (d,J=5.7 Hz, 1H).

EXAMPLE 69

2-[[(4-Piperdin-1-yl)-3-methyl)pyridin-2-yl]methylsulfinyl]-6-fluoro-5-(piperidin-1-yl)-1H-benzimidazole:

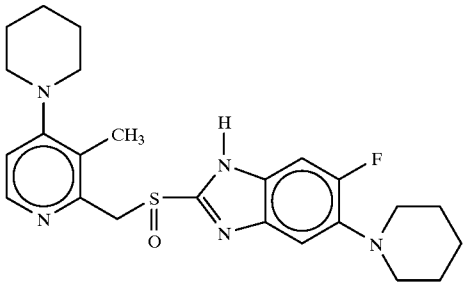

The title compound (0.13 g, 32%) was prepared by the above general procedure using 2-[[(4-(piperidin-1-yl)-3-methyl)pyridin-2-yl]methylthio]-6-fluoro-5-(piperidin-1yl)-1H-benzimidazole (0.4 g, 0.9 mmol) (obtained in example 18), m-chloroperbenzoic acid (50%, 0.3 g, 0.9 mmol) and chloroform (10 mL). mp 170–171° C.; IR (KBr) 3430, 1580, 1022 cm$^{-1}$; $^1$H NMR (CDCl$_3$) δ 1.62 (m, 6H, (CH$_2$)$_3$), 1.78 (m, 6H, (CH$_2$)3), 2.18 (s, 3H, Ch$_3$), 2.86 (t,J=5.3 Hz, 4H, N(CH$_2$)$_2$), 2.98 (t,J=5.1 Hz, 4H, N(CH$_2$)$_2$), 4.70 (ABq,J=8.8 Hz, Δv=5.6 Hz, 2H, SOCH$_2$), 6.78 (d,J=5.4Hz, 1H), 7.12 (d,J=5.2 Hz, 1H), 7.28 (d,J=9.5 Hz, 1H), 8.26 (d,J=5.4 Hz, 1H), Mass (m/z) 455 (M+).

EXAMPLE 70

2-[[-(4-Methoxy-3,5-dimethyl)pyridin-2-yl]methylsulfinyl]-6-fluoro-5-(4-methylpiperazin-1-yl)-1H-benzimidazole:

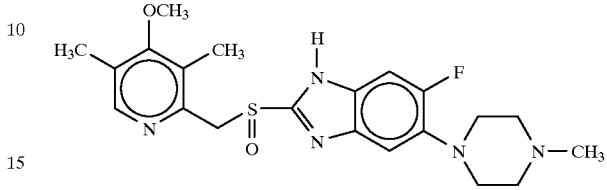

The title compound (0.3 g, 58%) was prepared by the above general procedure using 2-[[(4-methoxy-3,5-dimethyl)pyridin-2-yl]methylthio]-6-fluoro-5 -(4-methylpiperazin-1-yl)-1H-benzimidazole (0.5 g, 1.2 mmol) (obtained in example 19), m-chloroperbenzoic acid (50%, 0.48 g, 1.4 mmol) and chloroform (30 mL). mp 151–152° C.; IR (KBr) 3431, 1022 cm$^{-1}$; $^1$H NMR (DMSO-d$_6$) δ 2.20 (s, 3H, CH$_3$), 2.24 (s, 3H, CH$_3$), 2.30 (s, 3H, CH$_3$), 3.02 (m, 4H, N(CH$_2$)$_2$), 3.34 (m, 4H, N(CH$_2$)$_2$), 3.72 (s, 3H, OCH$_3$), 4.76 (ABq,J=8.6 Hz, Δv7.1 Hz, 2H, SOCH$_2$), 7.20 (d,J=7.6 Hz, 1H), 7.48 (d,J=13.5 Hz, 1H), 8.22 (s, 1H), Mass (m/z) 431 (M$^+$).

EXAMPLE 71

2-[[3-Methyl-4-(2,2,2-trifluoroethoxy)pyridin-2-yl]methylsulfinyl]-6-fluoro-5-(4-methylpiperazin-1-yl)-1H-benzimidazole:

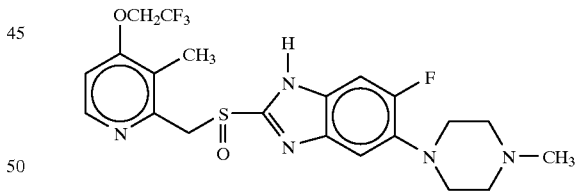

The title compound (0.15 g, 51%) was prepared by the above general procedure using 2-[[3-methyl-4-(2,2,2-trifluoroethoxy)pyridin-2-yl]methylthio]-6-fluoro-5-(4-methylpiperazin-1-yl)-1H-benzimidazole (0.28 g, 0.6 mmol) (obtained in example 20), m-chloroperbenzoic acid (50%, 0.25 g, 0.72 mmol) and chloroform (20 mL). mp 73–74° C.; IR (KBr) 3470, 1080 cm$^{-1}$; $^1$H NMR (CD$_3$OD) δ 2.20 (s, 3H, CH$_3$), 2.50 (s, 3H, CH$_3$), 2.88 (t,J=4.6 Hz, 4H, N(CH$_2$)$_2$), 3.18 (t,J=4.8 Hz, 4H, N(CH$_2$)$_2$), 4.68 (q,J=8.2 Hz, 2H, OCH$_2$CF$_3$), 4.80 (s, 2H, SOCH$_2$), 7.00 (d,J=5.8Hz, 1H), 7.24 (d,J=7.6Hz, 1H), 7.32 (d,J=12.2Hz, 1H), 8.18 (d,J= 5.7Hz, 1H); Mass (m/z) 486 (M$^+$1).

EXAMPLE 72

2-[[(4-Methoxy-3,5-dimethyl)pyridin-2-yl]methylsulfinyl]-6-fluoro-5-(4-t-butyloxycarbonyl piperazin-1-yl)-1H-benzimidazole:

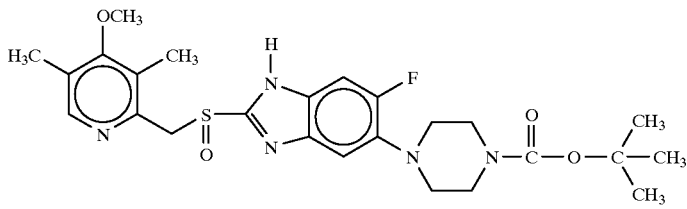

The title compound (0.2 g, 42%) was prepared by the above general procedure using 2-[[(4-methoxy-3,5-dimethyl)pyridin-2-yl]methylthio]-6-fluoro-5-(4-t,-butyloxycarbonylpiperazin-1-yl)-1H-benzimidazole (0.5 g, 1.0 mmol) (obtained in example 23), m-chloroperbenzoic acid (50%, 0.5 g, 1.5 mmol) and chloroform (30 mL). mp 115–116° C.; IR (KBr) 3436, 1687 cm$^{-1}$; $^1$H NMR (CDCl$_3$) δ 1.50 (s, 9H, 3×CH$_3$), 2.20 (s, 3H, CH$_3$), 2.28 (s, 3H, CH$_3$), 3.00 (t,J=5.3 Hz, 4H, N(CH$_2$)$_2$), 3.60 (t,J=5.6 Hz, 4H, N(CH$_2$)$_2$), 3.70 (s, 3H, OCH$_3$), 4.72 (ABq,J=8.6 Hz, Δv=6.7 Hz, 2H, SOCH$_2$), 7.12 (d,J=7.8 Hz, 1H), 7.30 (d,J=10.4 Hz, 1H), 8.20 (s, 1H); Mass (m/z) 517 (M$^+$).

EXAMPLE 73

2-[[(4-Methoxy-3methyl)pyridin-2-yl]methylsulfinyl]-6-fluoro-5-(4-t-butyloxy carbonylpiperazin-1-yl)-1H-benzimidazole:

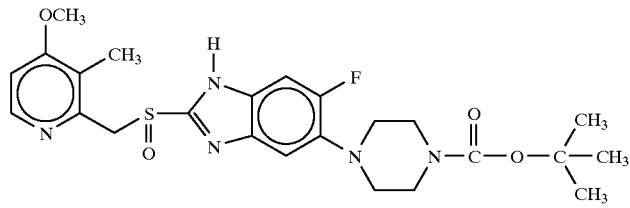

The title compound (0.1 g, 45%) was prepared by the above general procedure using 2-[[(4-methoxy-3-methyl)pyridin-2-yl]methylthio]-6-fluoro-5-(4-t-butyloxycarbonylpiperazin-1-yl)-1H-benzimidazole (0.25 g, 0.5 mmol) (obtained in example 24), m-chloroperbenzoic acid (40 %, 0.32 g, 0.75 mmol) and chloroform (10 mL). mp 170–171° C.; IR (KBr) 3420, 1695, 1096 cm$^{-1}$; $^1$H NMR (CDCl$_3$) δ 1.50 (s, 9H, 3×CH$_3$), 2.18 (s, 3H, CH$_3$), 3.00 (t,J=4.4 Hz, 4H, N(CH$_2$)$_2$), 3.60 (t,J=4.6 Hz, 4H, N(CH$_2$)$_2$), 3.88 (s, 3H, OCH$_3$), 4.74 (ABq,J=12.2 Hz, Δv =14.6 Hz, 2H, SOCH$_2$), 6.70 (d,J=5.7 Hz, 1H), 7.10 (d,J=7.8 Hz, 1H), 7.28 (d,J=11.3 Hz, 1H), 8.30 (d,J=5.8 Hz, 1H); Mass (m/z) 487 (M$^-$16).

EXAMPLE 74

2-[[(4-Methoxy-3-methyl)pyridin-2-yl]methylsulfinyl]-6-fluoro-5-(4-(ethylenedioxy)piperidin-1-yl)-1H-benzimidazole:

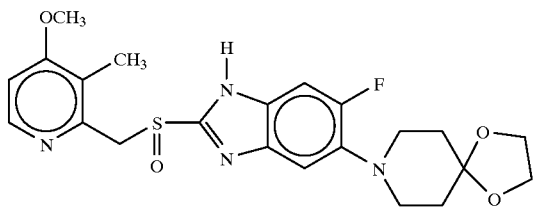

The title compound (0.42 g, 98%) was prepared by the above general procedure using 2-[[(4-methoxy-3-methyl)pyridin-2-yl]methylthio]-6-fluoro-5-(4-(ethylenedioxy)piperidin-1-yl)-1H-benzimidazole (0.44 g, 1.0 mmol) (obtained in example 25), m-chloroperbenzoic acid (50%, 0.3 g, 1.0 mmol) and dichloromethane (10 mL). mp 62–63° C.; IR (KBr) 3441, 1581, 1097 cm$^{-1}$, $^{1}$H NMR (CDCl$_3$) δ 1.94 (t, J=5.3 Hz, 4H, (CH$_2$)$_2$), 2.16 (s, 3H, CH$_3$), 3.16 (t, J=54 Hz, 4H, N(CH$_2$)$_2$), 3.86 (s, 3H, OCH$_3$), 4.02 (s, 4H, O(CH$_2$)$_2$O), 4.72 (ABq, J=13.7 Hz, Δv=15.4 Hz, 2H, SOCH$_2$), 6.72 (d, J=5.6Hz, 1H), 7.12 (d, J=6.8 Hz, 1H), 7.26 (d, J=8.8 Hz, 1H), 8.32 (d, J=5.4 Hz, 1H); Mass (m/z) 444 (M −16).

EXAMPLE 75

2-[[(4-Methoxy-3-methyl)pyridin-2-yl]methylsulfinyl]-6-fluoro-5-(4-ethylenedioxy)piperidin-1-yl)-1H-benzimidazole, sodium salt:

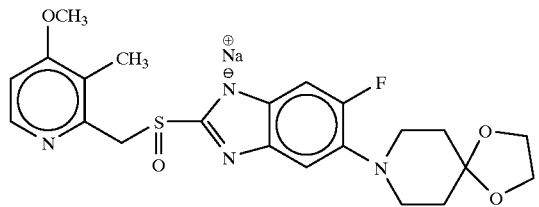

The title compound (0.42 g, 99%) was prepared by the above general procedure using 2-[[(4-methoxy-3-methyl)pyridin-2-yl]methylsulfinyl]-6-fluoro-5-(4-(ethylenedioxy)piperidin-1-yl)-1H-benzimidazole (0.032 g, 0.07 mmol) (obtained in example 74), and 0.1N NaOH solution (0.7 mL, 0.07 mmol). mp 152–153° C.; IR (KBr) 1583, 1468, 1096 cm$^{-1}$; $^{1}$H NMR (CDCl$_3$) δ 1.84 (m, 4H, (CH$_2$)$_2$), 2.20 (s, 3H, CH$_3$), 2.98 (m, 4H, N(CH$_2$)$_2$), 3.70 (s, 3H, OCH$_3$), 4.00 (s, 4H, O(CH$_2$)$_2$), 4.40 (s, 2H, SOCH$_2$), 6.30 (d, J=5.4 Hz, 1H), 6.98 (d, J=7.5 Hz, 1H), 7.12 (d, J=12.5 Hz, 1H), 7.84 (d, J=5.5 Hz, 1H).

EXAMPLE 76

2-[[(4-Methoxy-3-methyl)pyridin-2-yl]methylsulfinyl]-6-fluoro-5-(4-piperidon-1-yl)-1H-benzimidazole:

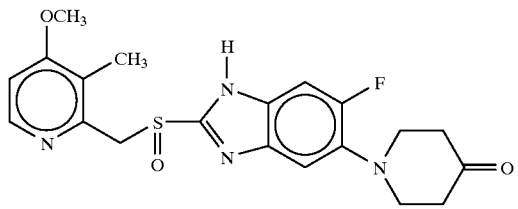

The title compound (0.25 g, 68%) was prepared by the above general procedure using 2-[[(4-mthoxy-3-methyl)pyridin-2-yl]methylthio]-6-fluoro-5-(4-piperidon-1-yl)-1H-benzindazole(0.3 g, 0.75 mmol) (obtained in example 26), m-chloroperbenzoic acid (50%, 0.26 g, 0.75 mmol) and dichloromethane (10 mL). mp 174–175° C.; IR (KBr) 3426, 1715, 1043 cm$^{-1}$; $^{1}$H NMR (CDCl$_3$) δ 2.20 (s, 3H, CH$_3$), 2.68 (t, J=5.9 Hz, 4H, (CH$_2$)$_2$), 3.40 (t, J=6.0 Hz, 4H, N(CH$_2$)$_2$), 3.86 (s, 3H, OCH$_3$), 4.72 (ABq, J=13.7 Hz, Δv=25.0 Hz, 2H, SOCH$_2$), 6.76 (d, J=6.0 Hz, 1H), 7.12 (d, J=8.2 Hz, 1H), 7.28 (d, J=8.9 Hz, 1H), 8.32 (d, J=5.8 Hz, 1H) ; Mass (m/z) 400 (M −16).

EXAMPLE 77

2-[[(4-Methoxy-3-methyl)pyridin-2-yl]methylsulfinyl]-6-fluoro-5-(4-piperidon-1-yl)-1H-benzimidazole, sodium salt:

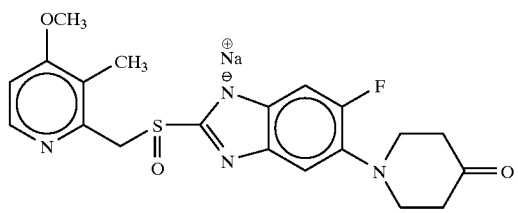

The title compound (0.043 g, 99%) was prepared by the above general procedure using 2-[[(4-methoxy-3-methyl)pyridin-2-yl]methylsulfinyl]-6-fluoro-5-(4-piperidon-1-yl)-1H-benzimidazole (0.04 g, 0.96 mmol) (obtained in example 76) and 0.1N NaOH solution (9.6 mL, 0.96 mmol). mp 72–73° C.; IR (KBr) 1711, 1471, 1095 cm$^{-1}$; $^{1}$H NMR (CDCl$_3$) δ 1.86 (s, 3H, CH$_3$), 2.56 (m, 4H, (CH$_2$)$_2$), 3.10 (m, 4H, N(CH$_2$)$_2$), 3.70 (s, 3H, OCH;), 4.40 (m, 2H, SOCH$_2$), 6.38 (d, J =5.0 Hz, 1H), 6.92 (d, J=7.4 Hz, 1H), 7.08 (d, J=12.2 Hz, 1H), 7.84 (d, J=4.8 Hz, 1H).

EXAMPLE 78

2-[[(4-Methoxy-3-methyl)pyridin-2-yl]methylsulfinyl]-6-fluoro-5-(4-(hydroxyimino)piperidin-1-yl)-1H-benzimidazole:

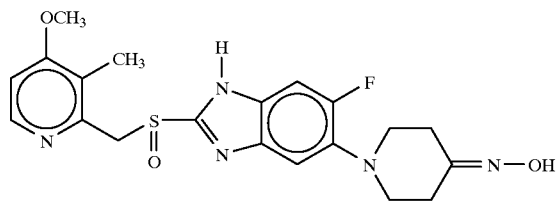

The title compound (0.25 g, 50%) was prepared by the above general procedure using 2-[[(4-methoxy-3-methyl)pyridin-2-yl]methylthio]-6-fluoro-5-(4-(hydroxyimino)piperidin-1-yl)-1H-benzimidazole (0.5 g, 1.2 mmol) (obtained in example 27), m-chloroperbenzoic acid (50%, 0.4 g, 1.2 mmol) and chloroform (10 mL). mp 196–197° C.; IR (KBr) 3421, 1583, 1021 cm$^{-1}$; $^{1}$H NMR (DMSO-d$_6$) δ 2.12 (s, 3H, CH$_3$), 2.42 (t, J=5.0 Hz, 2H, CH$_2$), 2.68 (t, J=5.5 Hz, 2H, CH$_2$), 3.08 (m, 4H, N(CH$_2$)$_2$), 3.86 (s, 3H, OCH$_3$), 4.72 (ABq, J=13.7 Hz, Δv=7.4 Hz, 2H, SOCH$_2$), 6.96 (d, J= 5.6 Hz, 1H), 7.22 (d, J=4.0 Hz, 1H), 7.46 (d, J=11.4 Hz, 1H), 8.24 (d, J=5.5 Hz, 1H), 10.44 (s, 1H, OH), 12.74 (s, 1H, NH); Mass (m/z) 396 (M −35).

EXAMPLE 79

2-[[(4-Methoxy-3-methyl)pyridin-2-yl]methylsulfinyl]-6-fluoro-5-(4-hydroxypiperidin-1-yl)-1H-benzimidazole:

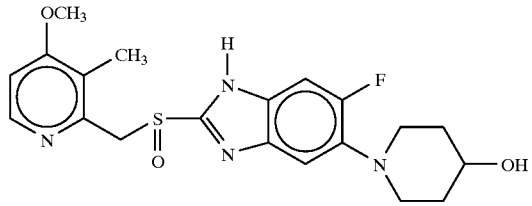

The title compound (0.15 g, 88%) was prepared by the above general procedure using 2-[[(4-methoxy-3-methyl)pyridin-2-yl]methylthio]-6-fluoro-5-(4-hydroxypiperidin-1-yl)-1H-benzimidazole (0.2 g, 0.5 mmol) (obtained in example 28), m-chloroperbenzoic acid (50%, 0.5 mmol, 0.17 g) and dichloromethane (10 mL). mp 66–68° C.; IR (KBr) 3415, 1079 cm$^{-1}$; 1H NMR (CDCl$_3$) δ 1.78–1.86 (m, 2H, CH$_2$), 2.00–2.16 (m, 2H, CH$_2$), 2.20 (s, 3H, CH$_3$), 2.86 (t,J=9.2 Hz, 2H, NCH$_2$), 3.36 (t,J=6.4 Hz, 2H, NCH$_2$), 3.87 (s, 3H, OCH$_3$), 3.82–3.94 (m, 1H, OCH), 4.20 (s, 1H, OH), 4.68 (ABq,J=13.7 Hz, Δv=22.1 Hz, 2H, SOCH$_2$), 6.74 (d,J=5.7 Hz, 1H), 7.08 (d,J=7.2 Hz, 1H), 7.32 (d,J=11.8 Hz, 1H). 8.32 (d,J=5.4 Hz, 1H), 11.70 (brs, 1H, NH). Mass (m/z) 418 (M$^+$.).

EXAMPLE 80

2-[[(4-Methoxy-3-methyl)pyridin-2-yl]methylsulfinyl]-6-fluoro-5-(hexamethyleneimin-1-yl)-1H-benzimidazole:

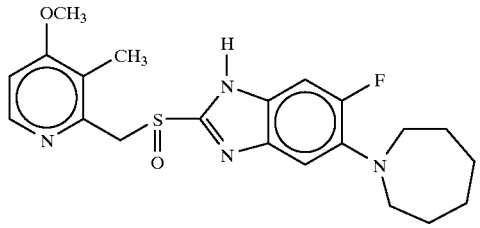

The title compound (0.15 g, 48%) was prepared by the above general procedure using 2-[[(4-methoxy-3-methyl)pyridin-2-yl]methylthio]-6-fluoro-5-(hexamethyleneimin-1H-benzimidazole (0.3 g, 0.75 mmol) (obtained in example 29), m-chloroperbenzoic acid (50%, 0.1 g, 0.6 mmol) and dichloromethane (20 mL). mp 144–145° C.; IR (KBr) 3429, 1587, 1097 cm$^{-1}$; $^1$H NMR (CDCl$_3$) δ 1.66 (m, 4H, (CH$_2$)$_2$), 1.86 (m, 4H, (CH$_2$)$_2$), 2.18 (s, 3H, CH$_3$), 3.28 (t,J =5.5 Hz, 4H, (CH$_2$)$_2$), 3.86 (s, 3H, OCH$_3$), 4.76 (ABq,J=13.4 Hz, Δv=10.4 Hz, 2H, SOCH$_2$), 6.74 (d,J=5.8 Hz, 1H), 7.00 (d,J=6.7 Hz, 1H), 7.28 (d,J=8.4 Hz, 1H), 8.32 (d, J =5.7 Hz, 1H); Mass (m/z) 400 (M −16).

EXAMPLE 81

2-[[(4-Methoxy-3-methyl)pyridin-2-yl]methylsulfinyl]-6-fluoro-5-(hexamethyleneimin-1-yl)-1H-benzimidazole, sodium salt:

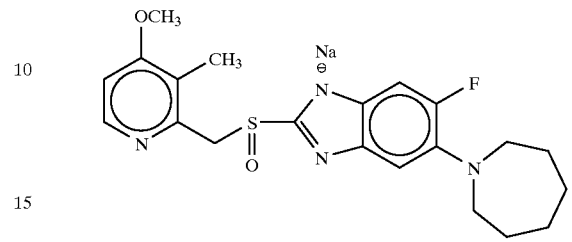

The title compound (0.04 g, 95%) was prepared by the above general procedure using 2-[[(4-methoxy-3-methyl)pyridin-2-yl]methylsulfinyl]-6-fluoro-5-(hexamethyleneimin-1-yl)-1H-benzimidazole (0.04 g, 0.9 mmol) (obtained in example 80) and 0.1N NaOH (1.0 mL, 0.1 mmol). mp 202–203° C.; IR (KBr) 1585, 1098 cm$^{-1}$; $^1$H NMR (CDCl$_3$) δ 1.64 (m, 4H, (CH$_2$)$_2$), 1.80 (m, 4H, (CH$_2$)$_2$), 2.18 (s, 3H, CH$_3$), 3.18 (t,J=5.0 Hz, 4H, N(CH$_2$)$_2$), 3.86 (s, 3H, OCH$_3$), 4.54 (ABq,J=12.8 Hz, Δv=61.4 Hz, 2H, SOCH$_2$), 6.94 (d,J=5.5 Hz, 1H), 7.08 (d,J=7.5 Hz, 1H), 7.12 (d,J=9.4Hz, 1H), 8.30 (d,J=5.4Hz, 1H).

EXAMPLE 82

2-[[(4-(Morpholin-1-yl)-3-methyl)pyridin-2-yl]methylsulfinyl]-6-fluoro-5-(hexamethyleneimin-1-yl)-1H-benzimidazole:

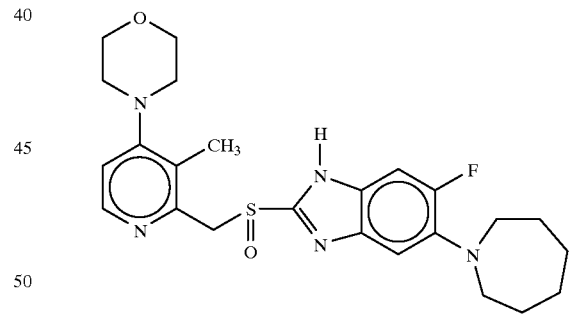

The title compound (0.15 g, 35%) was prepared by the above general procedure using, 2-[[(4-morpholin-1-yl)-3-methyl)pyridin-2-yl]methylthio]-6-fluoro-5-(hexamethyleneimin-1-yl)-1H-benzimidazole (0.42 g, 0.92 mmol) (obtained in example 30) m-chloroperbenzoic acid (50%, 0.16 g 0.92 mmol) and dichloromethane (10 mL). mp 162–163° C.; IR (KBr) 3439, 1577, 1051 cm$^{-1}$; $^1$H NMR (CDCl$_3$) δ 1.66 (m, 4H, (CH,)$_2$), 1.8 6 (m, 4H, (CH,)$_2$), 2.18 (s, 3H, CH$_3$), 2.88 (t,J=4.4 Hz, 4H, N(CH$_2$)$_2$), 3.32 (t,J=5.0 Hz, 4H, N(CH$_2$)$_2$), 3.82 (t,J=4.5 Hz, 4H, O(CH$_2$)$_2$), 4.70 (ABq,J=8.2 Hz, Δv=4.3 Hz, 2H, SOCH$_2$), 6.80 (d,J=5.6 Hz, 1H), 6.94 (d,J=7.1 Hz, 1H), 7.24 (d,J=10.2 Hz, 1H), 8.34 (d,J=5.4 Hz, 1H); Mass (m/z) 455 (M −16).

EXAMPLE 83

2-[[(4-Methoxy-3-methyl)pyridin-2-yl]methylsulfinyl]-6-fluoro-5-(2-(methoxymethyl)pyrrolidin-1-yl)-1H-benzimidazole:

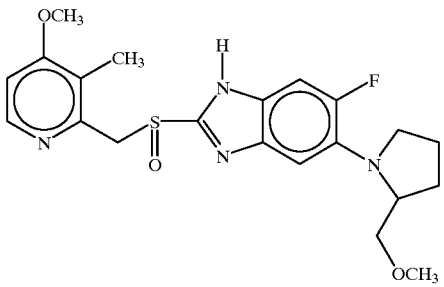

The title compound (0.2 g, 40%) was prepared by the above general procedure using 2-[[(4-methoxy-3-methyl)pyridin-2-yl]methylthio]-6-fluoro-5-(2-(methoxymethyl)pyrrolidin-1-yl)-1H-benzimidazole (0.5 g, 2.0 mmol) (obtained in example 31), m-chloroperbenzoic acid (50%, 0.16 g 0.96 mmol) and dichloromethane (10 mL). IR (Neat) 3340, 1581, 1098 cm$^{-1}$; 1H NMR (CDCl$_3$) δ 1.84–2.08 (m, 4H, (CH$_2$)$_2$), 2.20 (s, 3H, CH$_3$), 3.10–3.22 (m, 2H, NCH$_2$), 3.26 (s, 3H, OCH$_3$), 3.40–3.64 (m, 2H, OCH$_2$), 3.88 (s, 3H, OCH$_3$), 4.00–4.16 (m, 1H, OCH), 4.74 (ABq,J=8.2 Hz, Δv=10.8 Hz, 2H, SOCH$_2$), 6.76 (d,J=5.4 Hz, 1H), 6.92 (d,J=7.5 Hz, 1H), 7.30 (d,J=14.4 Hz, 1H), 8.34 (d,J=5.4 Hz, 1H); Mass (m/z) 416 (M −16).

EXAMPLE 84

2-[[(4-Methoxy-3-methyl)pyridin-2-yl]methylsulfinyl]-6-fluoro-5-(pyrrolidin-1-yl)-1H-benzimidazole:

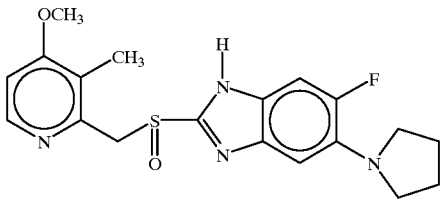

The title compound (0. 18 g, 34%) was prepared by the above general procedure using 2-[[(4-methoxy-3-methyl)pyridin-2-yl]methylthio]-6-fluoro-5-(pyrrolidin-1-yl)-1H-benzimidazole (0.5 g, 1.3 mmol) (obtained in example 32), m-chloroperbenzoic acid (50%, 0.45 g, 1.3 mmol) and chloroform (10 mL). mp 90–91° C.; IR (Neat) 3434, 1581, 1040 cm$^{-1}$; $^1$H NMR (CDCl$_3$) δ 1.98 (m, 4H, (CH$_2$)$_2$), 2.14 (s, 3H, CH$_3$), 3.36 (m, 4H, N(CH$_2$)$_2$), 3.84 (s, 3H, OCH$_3$), 4.72 (ABq,J =13.7 Hz, Δv=7.9 Hz, 2H, SOCH$_2$), 6.70 (d,J=5.4 Hz, 1H), 7.28 (d,J=6.3 Hz, 1H), 7.32 (d, J=8.4 Hz, 1H), 8.30 (d,J=5.4 Hz, 1H) ; Mass (m/z) 372 (M −16).

EXAMPLE 85

2-[[(4-Metboxy-3,5-dimethyl)pyridin-2-yl]methylsulfinyl]-5-(morpholin-1-yl)-1H-benzimidazole:

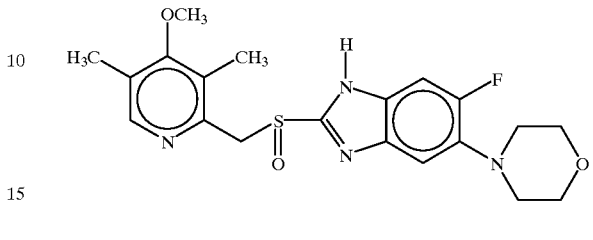

The title compound (0.17 g, 60%) was prepared by the above general procedure using 2-[[(4-methoxy-3,5-dimethyl)pyridin-2-yl]methylthio]-5-(morpholin-1-yl)-1H-benzimidazole (0.27 g, 0.7 mmol) (obtained in example 33), m-chloroperbenzoic acid (50%, 0.28 g, 0.84 mmol) and chloroform (20 mL). mp 97–98° C.; IR (KBr) 3418, 1075 cm$^{-1}$; $^1$H NMR (CD$_3$OD) δ 2.16 (s, 3H, CH$_3$), 2.24 (s, 3H, CH$_3$), 3.16 (t,J=4.6 Hz, 4H, N(CH$_2$)$_2$), 3.70 (s, 3H, OCH$_3$), 3.90 (t,J=4.8 Hz, 4H, O(CH$_2$)$_2$), 4.74 (ABq,J=9.8 Hz, Δv=5.6 Hz, 2H, SOCH$_2$), 7.08 (s, 1H), 7.14 (d,J=9.0 Hz, 1H), 7.54 (d,J=9.1 Hz, 1H), 8.12 (s, 1H); Mass (m/z) 400 (M$^+$).

EXAMPLE 86

2-[[3-Methyl-4-(2,2,2-trifluoroethoxy)pyridin-2-yl]methylsulfinyl]-5-(morpholin-1-yl)-1H-benzimidazole:

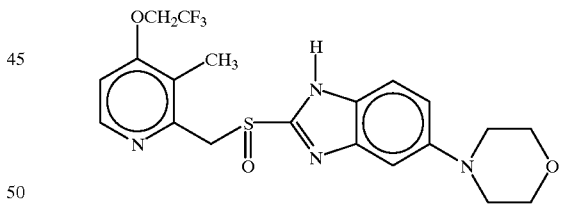

The title compound (0.28 g, 62%) was prepared by the above general procedure using 2-[[3-methyl-4-(2,2,2-trifluoroethoxy)pyridin-2-yl]methylthio]-5-(morpholin-1-yl)-1H-benzimnidazole (0.44 g, 1.0 mmol) (obtained in example 34), m-chloroperbenzoic acid (50%, 0.41 g, 1.2 mmol) in chloroform (20 mL). mp 102–103° C.; IR (KBr) 3431, 1043 cm$^{-1}$; $^1$H NMR (CD$_3$OD) δ 2.18 (s,3H, CH$_3$), 3.18 (t,J=4.6 Hz, 4H, N(CH$_2$)$_2$), 3.86 (t,J=4.6 Hz, 4H, O(CH2)$_2$), 4.64 (q,J =6.2 Hz, 2H, OCH$_2$CF$_3$), 4.80 (ABq, J=8.3 Hz, Δv=4.5 Hz, 2H, SOCH$_2$), 6.98 (d,J=5.7 Hz, 1H), 7.08 (s,1H), 7.14 (d,J=9.9 Hz, 1H), 7.52 (d,J=9.0 Hz, 1H), 8.22 (d,J=5.8 Hz, 1H); Mass (m/z) 454 (M$^+$).

EXAMPLE 87

2-[[(4-Methoxy-3-methyl)pyridin-2-yl]methylsulfinyl]-5-(morpholin-1-yl)-1H-benzimidazole:

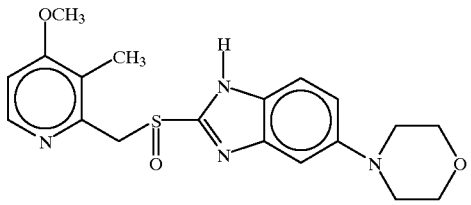

The title compound (0.16 g, 52%) was prepared by the above general procedure using 2-[[(4-methoxy-3-methyl)pyridin-2-yl]methylthio]-5-(morpholin-1-yl)-1H-benzimidazole (0.3 g, 0.8 mmol) (obtained in example 35), m-chloroperbenzoic acid (50%, 0.41 g, 1.2 mmol) and chloroform (10 mL). mp 158–159° C.; IR (KBr) 3429, 1044 cm$^{-1}$; $^1$H NMR (CD$_3$OD) δ 2.12 (s,3H, CH$_3$), 3.16 (t,J=4.7 Hz, 4H, N(CH$_2$)$_2$), 3.86 (t,J=4.9 Hz, 4H, O(CH$_2$)$_2$), 3.90 (s,3H, OCH$_3$), 4.74 (ABq,J=13.2 Hz, Δv=5.9 Hz, 2H, SOCH$_2$), 6.92 (d,J=5.6 Hz, 1H), 7.08 (s, 1H), 7.14 (d,J=9.2 Hz, 1H), 7.52 (d,J=9.2 Hz, 1H), 8.18 (d,J=5.7Hz, 1H); Mass (m/z) 386 (M$^+$).

EXAMPLE 88

2-[[(4-Methoxy-3-methyl)pyridin-2-yl]methylsulfinyl]-5-(morpholin-1-yl)-1H-benzimidazole, sodium salt:

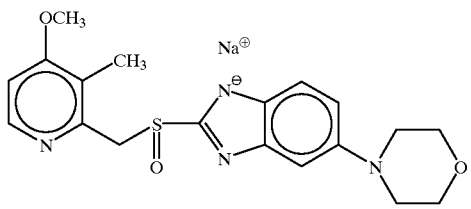

The title compound (0.03 g, 71%) was prepared by the above general procedure using 2-[[(4-methoxy-3-methyl)pyridin-2-yl]methylsulfinyl]-5-(morpholin-1-yl)-1H-benzimidazole (0.04 g, 0.1 mmol) (obtained in example 87) and 0.1N NaOH solution (1.0 mL, 0.1 mmol). mp 79–80° C.; IR (KBr) 1583, 1040 cm$^{-1}$; $^1$H NMR (DMSO-d$_6$) δ 2.20 (s,3H, CH$_3$), 3.00 (t,J=4.7 Hz, 4H, N(CH$_2$)$_2$), 3.76 (t,J=4.6 Hz, 4H, O(CH$_2$)$_2$, 3.88 (s,3H, OCH$_3$), 4.60 (ABq,J=12.8 Hz, Δv =65.9 Hz, 2H, SOCH$_2$), 6.72 (d,J=6.7 Hz, 1H), 6.94 (d,J=5.6 Hz, 1H), 6.98 (s,1H), 7.34 (d, J=8.7 Hz, 1H), 8.32 (d,J=5.4 Hz, 1H).

EXAMPLE 89

2-[[(4-Methoxy-3,5-dimethyl)pyridin-2-yl]methylsulfinyl]-5-(4-methylpiperazin-1-yl)-1H-benzimidazole:

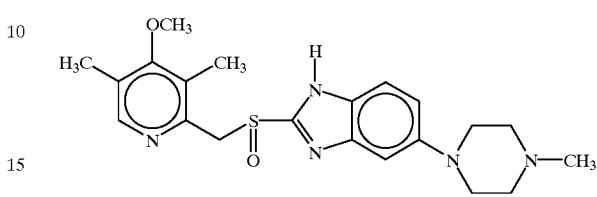

The title compound (0.2 g, 65%) was prepared by the above general procedure using 2-[[(4-methoxy-3,5-dimethyl)pyridin-2-yl]methylthio]-5-(4-methylpiperazin-1-yl)-1H-benzimidazole (0.3 g, 0.75 mmol) (obtained in example 36), m-chloroperbenzoic acid (50%, 0.26 g, 1.2 mmol) and chloroform (30 mL). IR (KBr) 3422, 1447, 1076 cm$^{-1}$; $^1$H NMR (CDCl$_3$) δ 2.16 (s,3H, CH$_3$), 2.26 (s,3H, CH$_3$), 2.36 (s,3H, NCH$_3$), 2.66 (t,J=4.7 Hz, 4H, N(CH$_2$)$_2$), 3.20 (t,J=4.6 Hz, 4H, N(CH$_2$)$_2$), 3.76 (s, 3H, OCH$_3$), 4.52 (s,2H, SOCH$_2$), 6.99 (d,J=8.6 Hz, 1H), 7.04 (s, 1H), 7.40 (d,J=9.3 Hz, 1H), 8.14 (s,1H); Mass (m/z ) 413 (M$^+$).

EXAMPLE 90

2-[[(4-Methoxy-3-methyl)pyridin-2-yl]methylsulfinyl]-5-(4-t-butyloxycarbonylpiperazin-1-yl)-1H-benzimidazole:

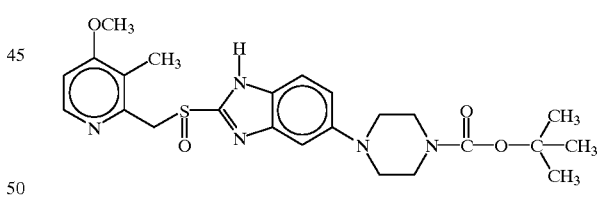

The title compound (0.11 g, 54%) was prepared by the above general procedure using 2-[[(4-methoxy-3-methyl)pyridin-2-yl]methylthio]-5-(4-t-butyloxycarbonylpiperazin-1-yl)-1H-benzimidazole (0.2 g, 0.42 mmol) (obtained in example 38), m-chloroperbenzoic acid (50%, 0.21 g, 0.63 mmol) and chloroformn (20 mL). mp 169–170° C.; IR (KBr) 3427, 1696, 1070 cm$^{-1}$; $^1$H NMR (CDCl$_3$) δ 1.48 (s, 9H, 3×CH$_3$), 2.14 (s,3H, CH$_3$), 3.14 (t,J=4.5 Hz, 4H, N(CH$_2$)$_2$), 3.60 (t,J=4.5 Hz, 4H, N(CH$_2$)$_2$), 388 (s,3H, OCH$_3$), 4.76 (ABq,J=10.2 Hz, Δv =5.4 Hz, 2H, SOCH$_2$), 6.92 (d,J=5.8 Hz, 1H), 7.12 (d,J=9.0 Hz, 1H), 7.18 (s,1H), 7.54 (d, J=8.9 Hz, 1H), 8.32 (d,J=5.8 Hz, 1H); Mass (m/z) 469 (M −16).

EXAMPLE 91

2-[[-(4-Methoxy-3-methyl)pyridin-2-yl]methylsulfinyl]-5-(hexamethyleneimin-1-yl)-1H-benzimidazole:

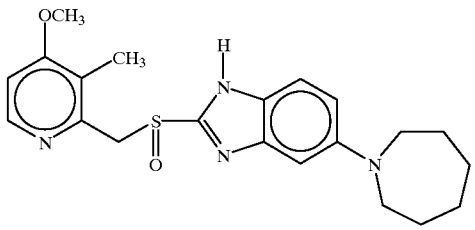

The title compound (0.15 g, 36%) was prepared by the above general procedure using 2-[[(4-methoxy-3-methyl)pyridin-2-yl]methylthio]-5-(hexamethyleneimin-1-yl)-1H-benzimidazole(0.4 g, 1.0 mmol) (obtained in example 40), m-chloroperbenzoic acid (50%, 0.34 g, 1.0 mmol) and dichloromethane (10 mL). mp 158–159° C.; IR (KBr) 3435, 1581, 1045 cm$^{-1}$; $^1$H NMR (CDCl$_3$) δ 1.58 (m,4H, CH$_2$)$_2$), 1.82 (m,4H, (CH$_2$)$_2$), 2.20 (s,3H, CH,), 3.52 (t,J=5.7 Hz, 4H, N(CH$_2$)$_2$), 3.88 (s,3H, OCH$_3$), 4.74 (ABq,J=13.3 Hz, Δv=13.7 Hz, 2H, SOCH$_2$), 6.74 (d,J =5.5 Hz, 1H), 6.82 (d,J=9.4Hz, 1H), 7.27 (s,1H), 7.52 (d,J=9.1 Hz, 1H), 8.36 (d,J=5.5 Hz, 1H), 11.12 (brs, 1H, NH); Mass (m/z) 382 (M −16).

EXAMPLE 92

2-[[(4-Methoxy-3-methyl)pyridin-2-yl]methylsulfinyl]-4,6-difluoro-5-(morpholin-1-yl)-1H-benzimidazole:

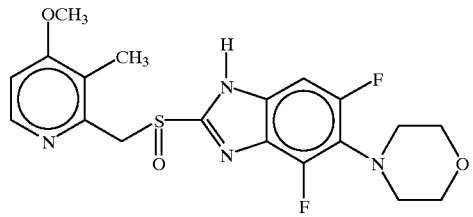

The title compound (0.18 g, 44%) was prepared by the above general procedure using 2-[[(4-methoxy-3-methyl)pyridin-2-yl]methylthio]-4,6-difluoro-5-morpholin-1-yl)-1H-benzimidazole (0.4 g, 1.0 mmol) (obtained in example 41), m-chloroperbenzoic acid (40%, 0.55 g, 1.28 mmol) and chloroform (20 mL). mp 186–187° C.; IR (KBr) 3441, 1582, 1040 cm$^{-1}$; $^1$H NMR (CDCl$_3$) δ 2.20 (s,3H, CH$_3$), 3.22 (t,J=4.5 Hz, 4H, N(CH$_2$)$_2$), 3.82 (t,J=4.3 Hz, 4H, N(CH$_2$)$_2$), 3.90 (s,3H, OCH$_3$), 4.80 (ABq,J=13.9 Hz, Δv=10.9 Hz, 2H, SOCH$_2$), 6.76 (d, J=5.8 Hz, 1H), 7.05 (d,J=10.4 Hz, 1H), 8.32 (d,J=5.5 Hz, 1H); Mass (m/z) 422 (M$^+$).

The compounds of the present invention have been tested for their anti-ulcer activity via H$^+$/K$^+$- ATPase inhibition activity using standard state of the art in vitro as well as in vivo pharmacological protocols.

A) H$^+$/K$^+$- ATPase inhibition

The most efficient method for reducing acid-related gastrointestinal disorder is through the inhibition of proton pump on the gastric parietal cell. The proton pump (H$^+$/K$^+$ ATPase) is a membrane bound enzyme that exchanges protons for K$^+$ions across the apical surface. Associated with this is a K$^+$/Cl$^-$cotransporter which recycles the K$^+$together with the Cl$^-$across the apical surface where HCl is formed by the Cl$^-$ions together with the secreted H$^+$. This enzyme has an ATP hydrolyzing activity which requires intravesicular K$^+$.

Principle

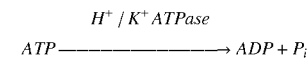

$P_i$ liberated is estimated, the amount of $P_i$ liberated is proportional to the enzyme activity.

(i) Preparation of H$^+$/K$^+$- ATPase

Rabbit gastric mucosa containing H$^+$/K$^+$- ATPase activity is isolated according to the modified method of Reenstra et al. (Reenstra, W. W. & Forte, J. G. *Methods in enzymology* 1990, 92:551). After homogenizing the fundic mucosa in buffer (5 mM PIPES, 0.25M sucrose, 0.2 mM EDTA, pH 6.8), the high speed supernatant is layered over 20 mL of 37% sucrose bed and subjected to ultracentrifugation at 25,000 rpm (SW-28 rotor) for 4 h at 4° C. The interfacial layer is collected and diluted with homogenization buffer, subjected to ultracentrifugation at 25,000 rpm for 1 hour. The pellet thus obtained is used for enzyme assay.

(ii) Measurement of the activity of H$^+$/K$^+$- ATPase

Assay is carried out according to the protocol described by Beil, R (Beil, R. *Br. J. Pharmacol,* 1984, 82:651). The compound of the present invention was incubated at various concentrations with H$^+$/K$^+$- ATPase and the membrane protein (10 μg/mL) in assay medium containing 50 mM Tris buffer solution having a pH of 6.5, 250 mM sucrose, 3 mM MgCl$_2$, 50 μM valinomycin with or without 10 mM KCl for 10 minutes (total volume 1 mL). The enzyme reaction is initiated by adding ATP to a final concentration of 3 mM. After incubation for 15 min. at 37° C., the reaction is stopped by adding equal volume of phosphate reagent and the Pi produced by the hydrolysis of ATP is determined by the method of Lin et al. (Lin T -I. & Morales, M. F. *Anal. Biochem.* 1977, 77:10). The H$^+$/K$^+$- ATPase activity is calculated by subtracting the basal activity (in absence of KCl) from the rate of hydrolysis of ATP in the presence of K$^+$. The percent inhibition were determined for the test compounds.

| Example No. | % Inhibition at 10 mg/kg | Example No. | % Inhibition at 10 mg/kg |
| --- | --- | --- | --- |
| Example 67 | 100 | Example 82 | 100 |
| Example 68 | 100 | Example 84 | 93 |
| Example 69 | 97 | Example 87 | 90 |
| Example 73 | 93 | Example 90 | 100 |
| Example 80 | 100 | Example 91 | 97 |
| Example 81 | 100 | Omeprazole | 75 |

B) Gastric acid antisecretory activity

The inhibitory effect on gastric acid secretion is determined in pylorus ligated rat model according to Shay et al. (Shay, M., Komarov, S. A., Fels, D., Merange, D., Gruenstein, H. & Siplet, H. *Gastroenterology* 1945, 5:43). Male wistar rats weighing about 150–200 g fasted for 24 h with ad libitum are used. Under ether anaesthesia the laparotomy is performed and pylorus portion of the stomach is isolated and ligated with surgical suture. The test drug/vehicle is administered intraduodenally and the abdominal incision is closed using Michael clips. After 2 h, the animals were sacrificed with excess ether anaesthesia and stomach is removed. The gastric contents are collected and centrifuged at 10,000 rpm for 10 min. The volume of the gastric juice is measured and acid concentration is estimated by titrating an aliquot of the gastric juice against 0.004N NaOH using phenolphthalein as the indicator. Total acid output is expressed as milliequivalents/L/kg/h and volume of gastric juice as mL/kg/h. The $ED_{50}$ value for the test compound is calculated according to graphical method. Omeprazole is used as a standard compound.

The test compounds are compared at a dose of 10 mg/kg.

The $IC_{50}$ value for the inhibition of H+/K+ ATPase of compound of example 57 which is a representative of the compounds of the present invention has been found to be 2.6 $\mu$M and whereas the $IC_{50}$ value for Omeprazole is 4.35±0.56 $\mu$M. In the in vivo experiment, the $ED_{50}$ value of compound of Example 57 is found to 3.0±0.2 mg/kg whereas the $ED_{50}$ value for Omeprazole is 4.96±0.5 mg/kg.

We claim:

1. A compound of fornula (I)

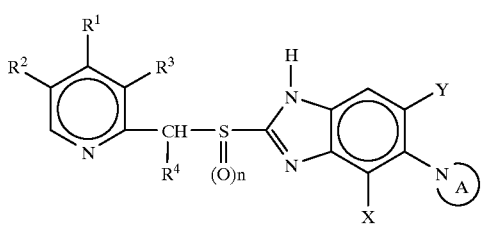

its tautomeric forms, its stereoisomiers, its polymorphs, its pharmaceutically acceptable salts or its pharmaceutically acceptable solvates, wherein X and Y are the same or different and independently represent a hydrogen, halogen, or optionally halogenated ($C_1$–$C_6$)alkoxy group, optionally halogenated($C_1$–$C_6$)alkyl group; A represents a substituted or unsubstituted 3 to 7 membered nitrogen containing heterocycle excluding substituted or unsubstituted pyrroles; or A represents a substituted or unsubstituted 5 to 7 membered nitrogen containing heterocycle containing one additional or two additional heteroatoms selected from N, O, S or a group $NR^5$ where $R^5$ represents hydrogen, ($C_1$–$C_6$)alkyl, aralkyl, acyl, alkoxycarbonyl, aryloxycarbonyl, or aralkoxycarbonyl; the heterocycle A is saturated or contains one, two or three double bonds, the heterocycle A, is linked specifically through N-atom to the benzimidazole moiety; $R^4$ represents hydrogen, halogen or ($C_1$–$C_3$)alkyl group; $R^2$ and $R^3$ are the same or different and independently represent hydrogen, halogen, nitro, cyano, or optionally substituted groups selected from amino, ($C_1$–$C_6$)alkyl, ($C_1$–$C_6$)alkoxy, aryloxy or aralkoxy groups; $R^1$ may be hydrogen, halogen, or substituted or unsubstituted groups selected from ($C_1$–$C_8$)alkyl, aryl, aralkyl, ($C_3$–$C_{10}$)cycloalkyl, ($C_1$–$C_6$)alkylthio, ($C_1$–$C_6$)alkenylthio, heterocyclyl, amino, ($C_1$–$C_8$)alkylamino, dialkylamino, arylamino, diarylamino, alkylarylamino, ($C_1$–$C_6$)alkoxy, ($C_2$–$C_6$)acyloxy, ($C_3$–$C_{10}$)cyclo-alkyloxy, aralkoxy, aryloxy, alkoxyalkoxy, or a group -O—(CH$_2$)$_m$-O—(CH$_2$)$_p$-R$^6$ where m is an integer ranging from 1 to 10 and p is an integer ranging from 0 to 3 and $R^6$ is a linear or branched ($C_1$–$C_6$)alkyl, heterocyclyl, heteroaryl, aralkyl, hydroxy, alkoxy, aryloxy, aralkoxy, alkoxycarbonyl, alkoxyalkyl, or alkoxyalkoxy; and n is an integer ranging from 0 to 2, with a proviso that when $R^1$ represents alkoxy group, and n is 1, $R^3$ does not represent hydrogen and A does not represent unsubstituted piperidinyl or unsubstituted pyrrolidinyl group.

2. A compound as claimed in claim 1, wherein the substituents on $R^1$, $R^2$ and $R^3$ are selected from the group consisting of halogen, ($C_1$–$C_3$)alkyl, aryl, aralkyl, ($C_1$–$C_3$)alkoxy, hydroxy, amino, amino($C_1$–$C_3$)alkyl or hydroxy ($C_1$–$C_3$)alkyl.

3. A compound as claimed in claim 1, wherein the heterocycle represented by A is selected from substituted or unsubstituted groups selected from aziridinyl, azetidinyl, azepinyl, piperidinyl, pyrrolidinyl, pyrrolinyl, hexahydroazepinyl, 3-oxazepinyl, 4-oxazepinyl, 3-thiazepinyl, 4-thiazepinyl, 1,3-diazepinyl, 1,4-diazepinyl, piperazinyl, 1,3-diazolidinyl, morpholinyl, 4-thiomorpholinyl, oxazolidinyl, imidazolyl, triazolyl, pyrazolyl, 2-pyrazolinyl, 1,4-dihydropyridazinyl, 4-oxazolinyl, 4-thiazolinyl, 1,4-oxazinyl or tetrahydropyridinyl groups.

4. A compound as claimed in claim 1, wherein the substituents on the heterocycle represented by A are selected from the group consisting of halogen, amino, hydroxy, cyano, oxo, formyl, hydroxylamino, hydroxylimino, ($C_1$–$C_6$)alkoxyamino, ($C_1$–$C_6$)alkoxyimino, ($C_1$–$C_6$)alkyl, ($C_3$–$C_{10}$)cycloalkyl, hydroxy($C_1$–$C_6$)alkyl, mercapto, thio ($C_1$–$C_6$)alkyl, ($C_1$–$C_6$)alkylthio, amino($C_1$–$C_6$)alkyl, ($C_1$–$C_6$)alkylamino, dialkylamino, arylamino, ($C_1$–$C_6$) alkoxy, aryloxy, ($C_3$–$C_{10}$)cycloalkyloxy, ($C_1$–$C_3$) alkylenedioxy, aryl, heterocyclyl, N-alkylimino, alkoxyalkyl, acyl, acyloxy, alkoxycarbonyl, and aryloxycarbonyl.

5. A compound as claimed in claim 1, wherein the groups represented by X and Y are selected from hydrogen, halogen, optionally halogenated ($C_1$–$C_6$)alkoxy, or optionally halogenated ($C_1$–$C_6$)alkyl.

6. A compound as claimed in claim 1, wherein the group represented by $R^4$ is hydrogen atom.

7. A compound as claimed in claim 1, wherein the groups represented by $R^2$ and $R^3$ are selected from hydrogen, optionally halogenated ($C_1$–$C_3$)alkyl, or optionally halogenated ($C_1$–$C_3$)alkoxy groups.

8. A compound as claimed in claim 1, wherein the groups represented by $R^1$ are selected from hydrogen, halogen, optionally halogenated ($C_1$–$C_6$)alkyl, optionally halogenated ($C_1$–$C_6$)alkoxy, amino, optionally halogenated alkylamino, optionally halogenated dialkylamino, heterocyclyl, optionally halogenated alkoxyalkoxy or a group -O—(CH$_2$)$_m$-O(CH$_2$)$_p$-R$^6$ wherein m is an integer ranging from 1 to 10 and p is an integer ranging from 0 to 3 and $R^6$ is a linear or branched ($C_1$–$C_6$)alkyl, heterocyclyl, heteroaryl, aralkyl, hydroxy, alkoxy, aryloxy, aralkoxy, alkoxycarbonyl, alkoxyalkyl, and alkoxyalkoxy groups.

9. A process for the preparation of a compound of formula (I)

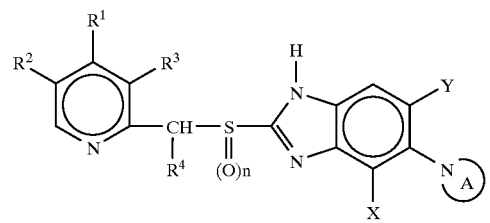

its tautomeric forms, its stereoisomers, its polymorphs, its pharmaceutically acceptable salts or its pharmaceutically acceptable solvates, wherein X and Y are the same or different and independently represent a hydrogen, halogen, or optionally halogenated ($C_1$–$C_6$)alkoxy group, optionally halogenated($C_1$–$C_6$)alkyl group; A represents a substituted or unsubstituted 3 to 7 membered nitrogen containing heterocycle excluding substituted or unsubstituted pyrroles; or A represents a substituted or unsubstituted 5 to 7 membered nitrogen containing heterocycle containing one additional or two additional heteroatoms selected from N, O, S or a group $NR^5$ where $R^5$ represents hydrogen, $(C_1-C_6)$alkyl, aralkyl, acyl, alkoxycarbonyl, aryloxycarbonyl, or aralkoxycarbonyl; the heterocycle A is saturated or contains one, two or three double bonds, the heterocycle A, is linked specifically through N-atom to the benzimidazole moiety; $R^4$ represents hydrogen, halogen or $(C_1-C_3)$alkyl group; $R^2$ and $R^3$ are the same or different and independently represent hydrogen, halogen, nitro, cyano, or optionally substituted groups selected fxom amino, $(C_1-C_6)$alkyl, $(C_1-C_6)$alkoxy, aryloxy or aralkoxy groups; $R^1$ may be hydrogen, halogen, or substituted or unsubstituted groups selected from $(C_1-C_8)$ alkyl, aryl, aralkyl, $(C_3-C_{10})$cycloalkyl, $(C_1-C_6)$alkylthio, $(C_1-C_6)$alkenylthio, heterocyclyl, amino, $(C_1-C_8)$ alkylamino, dialkylamino, arylamino, diarylamino, alkylarylamino, $(C_1-C_6)$alkoxy, $(C_2-C_6)$acyloxy, $(C_3-C_{10})$ cyclo-alkyloxy, aralkoxy, aryloxy, alkoxyalkoxy, or a group $-O-(CH_2)_m-O-(CH_2)_p-R^6$ where in is an integer ranging from 1 to 10 and p is an integer ranging from 0 to 3 and $R^6$ is a linear or branched $(C_1-C_6)$alkyl, heterocyclyl, heteroaryl, aralkyl, hydroxy, akoxy, aryloxy, aralkoxy, alkoxycarbonyl, alkoxyalkyl, or alkoxyalkoxy; and n is zero, which comprises:

i) reacting a compound of formula (III) wherein $R^1$, $R^2$, $R^3$ and $R^4$ are as defined above and L is a leaving group with a compound of formula (IV) where X, Y and A are as defined above,

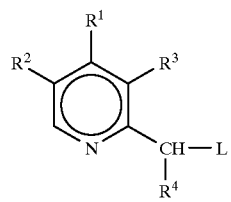

(III)

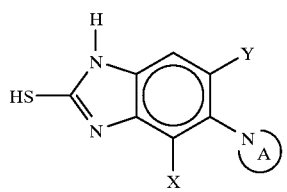

(IV)

to prepare a compound of formula II); or ii) reacting a compound of formula (VI) where $R^1$, $R^2$, $R^3$ and $R^4$ are as defined above with a compound of formula (VII) where X, Y and A are as defined above,

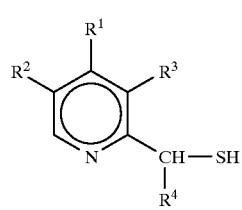

(VI)

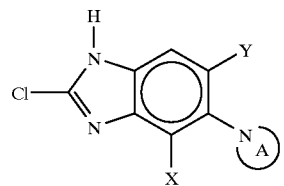

(VII)

to prepare a compound of formula (I); or iii) reacting a compound of formula (VIII) where $R^1$, $R^2$, $R^3$ and $R^4$ are as defined above, with a compound of formula (IX) where X, Y and A are as defined above,

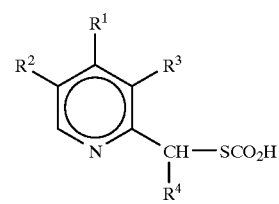

(VIII)

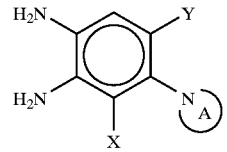

(IX)

to prepare a compound of formula (I); or iv) converting the compounds of formula (I) obtained in i), ii) or iii) described above into pharmaceutically acceptable salts, or pharmaceutically acceptable solvates which further comprises reacting the compound of formula (I) with 1 to 4 equivalents of a base or acid.

10. A process for the preparation of compounds of formula (I)

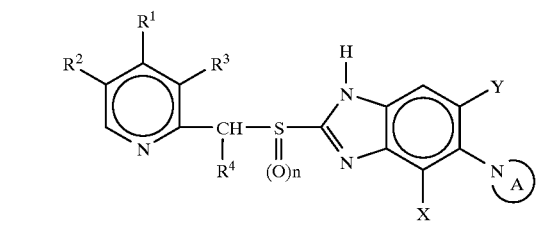

(I)

its tautomeric forms, its stereoisomers, its polymorphs, its pharmaceutically acceptable salts or its pharmaceutically acceptable solvates, wherein X and Y are the same or different and independently represent a hydrogen, halogen, or optionally halogenated $(C_1-C_6)$alkoxy group, optionally halogenated $(C_1-C_6)$alkyl group; A represents a substituted or unsubstituted 3 to 7 membered nitrogen containing heterocycle excluding substituted or unsubstituted pyrroles; or A represents a substituted or unsubstituted 5 to 7 membered nitrogen containing heterocycle containing one additional or two additional heteroatoms selected from N, O, S or a group $NR^5$ where $R^5$ represents hydrogen, $(C_1-C_6)$alkyl, aralkyl, acyl, alkoxycarbonyl, aryloxycarbonyl, or aralkoxycarbonyl; the heterocycle A is saturated or contains one, two or three double bonds, the heterocycle A, is linked specifically through N-atom to the benzimidazole moiety; $R^4$ represents hydrogen, halogen or $(C_1-C_3)$alkyl group; $R^2$ and $R^3$ are the same or different and independently represent hydrogen, halogen, nitro, cyano, or optionally substituted groups selected from amino, $(C_1-C_5)$alkyl, $(C_1C_6)$alkoxy, aryloxy or aralkoxy groups; $R^1$ may be hydrogen, halogen, or substituted or unsubstituted groups selected from $(C_1-C_8)$ alkyl, aryl, aralkyl, $(C_3-C_{10})$cycloalkyl, $(C_1-C_6)$alkylthio, $(C_1-C_6)$alkenylthio, heterocyclyl, amino, $(C_1-C_8)$ alkylamino, dialkylamino, arylamino, diarylamino, alkylarylamino, $(C_1-C_6)$alkoxy, $(C_2-C_6)$acyloxy, $(C_3-C_{10})$ cycloalkyloxy, aralkoxy, aryloxy, alkoxyalkoxy, or a group $-O-(CH_2)_m-O-(CH_2)_p-R^6$ where m is an integer ranging from 1 to 10 and p is an integer ranging from 0 to 3 and $R^6$ is a linear or branched $(C_1-C_6)$alkyl, heterocyclyl, heteroaryl, aralkyl, hydroxy, alkoxy, aryloxy, aralkoxy, alkoxycarbonyl, alkoxyalkyl, or alkoxyalkoxy; and n is one, with a proviso that $R^1$ represents alkoxy group, $R^3$ represents hydrogen, and n is 1, with a proviso that when $R^1$ represents alkoxy group, and n is 1, $R^3$ does not represent hydrogen and A does not represent unsubstituted piperidinyl or unsubstituted pyrrolidinyl group which comprises:

i) oxidizing the compound of formula (I) obtained in claim 9, with approximately one equimolar amount of an oxidizing agent, that will oxidize the compound of formula (I) obtained in claim 9 to prepare a compound of formula (I);

ii) reacting a compound of formula (X) where $R^1$, $R^2$, $R^3$ are as defined above and Z represents a leaving group with a compound of formula (XI) where X, Y, n, $R^4$ and A are as defined above, $R^7$ represents hydrogen or a nitrogen protecting group and M represents an lkali metal

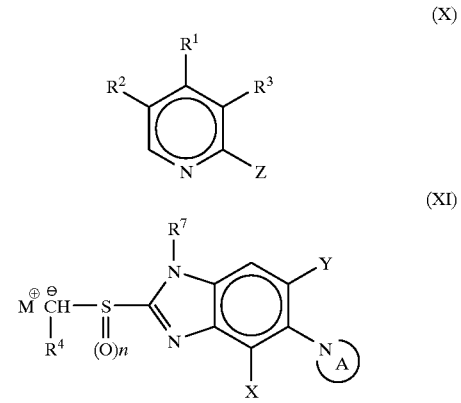

(X)

(XI)

to prepare a compound of formula (I);

iii) optionally converting the compound of formula (I) obtained in i) or ii) described above into pharmaceutically acceptable salts, or pharmaceutically acceptable solvates which further comprises reacting the compound of formula (I) with 1 to 4 equivalents of a base or acid.

11. A process for the preparation of compounds of formula (I)

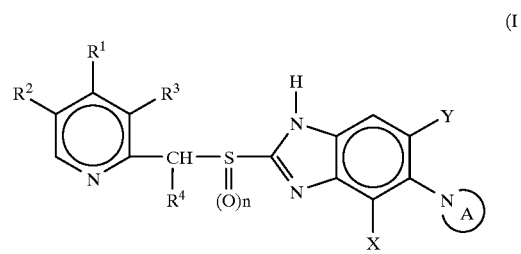

(I)

its tautomeric forms, its stereoisomers, its polymorphs, its pharmaceutically acceptable salts or its pharmaceutically acceptable solvates, wherein X and Y are the same or different and independently represent a hydrogen, halogen, or optionally halogenated $(C_1-C_6)$alkoxy group, optionally halogenated$(C_1-C_6)$alkyl group; A represents a substituted or unsubstituted 3 to 7 membered nitrogen containing heterocycle excluding substituted or unsubstituted pyrroles; or A represents a substituted or unsubstituted 5 to 7 membered nitrogen containing heterocycle containing one additional or two additional heteroatoms selected from N, O, S or a group $NR^5$ where $R^5$ represents hydrogen, $(C_1-C_6)$alkyl, aralkyl, acyl, aikoxycarbonyl, aryloxycarbonyl, or aralkoxycarbonyl; the heterocycle A is saturated or contains one, two or three double bonds, the heterocycle A, is linked specifically through N-atom to the benzimidazole moiety; $R^4$ represents hydrogen, halogen or $(C_1-C_3)$alkyl group; $R^2$ and $R^3$ are the same or different and independently represent hydrogen, halogen, nitro, cyano, or optionally substituted groups selected from amino, $(C_1-C_6)$alkyl, $(C_1-C_6)$alkoxy, aryloxy or aralkoxy groups; $R^1$ may be hydrogen, halogen, or substituted or unsubstituted groups selected from $(C_1-C_8)$ alkyl, aryl, aralkyl, $(C_3-C_{10})$cycloalkyl, $(C_1-C_6)$alkylthio, $(C_1-C_6)$alkenylthio, heterocyclyl, amino, $(C_1-C_8)$ alkylamino, dialkylamino, arylamino, diarylamino, alkylarylamino, $(C_1-C_6)$alkoxy, $(C_2-C_6)$acyloxy, $(C_3-C_{10})$ cyclo-alkyloxy, aralkoxy, aryloxy, alkoxyalkoxy, or a group $-O-(CH_2)_m-O-(CH_2)_p-R^6$ where m is an integer ranging from 1 to 10 and p is an integer ranging from 0 to 3 and $R^6$ is a linear or branched $(C_1-C_6)$alkyl, heterocyclyl, heteroaryl, aralkyl, hydroxy, alkoxy, aryloxy, aralkoxy, alkoxycarbonyl, alkoxyalkyl, or alkoxyalkoxy; and n is two, which comprises:

i) oxidizing the compound of formula (I) obtained in claim 9, with two equimolar amounts of an oxidizing agent that will oxidize the compound of formula (I) obtained in claim 9, to prepare a compound of formula (I); or ii) oxidizing the compound of formula (I) obtained in claim 10, with one equimolar amount of an oxidizing agent that will oxidize the compound of formula I obtained in claim 10, to prepare a compound of formula (I); or iii) reacting a compound of formula (X) where $R^1$, $R^2$, $R^3$ are as defined above and Z represents a leaving group with a compound of formula (XI) where X, Y, n, $R^4$ and A are as defined above, $R^7$ represents hydrogen or a nitrogen protecting group and M represents an alkali metal

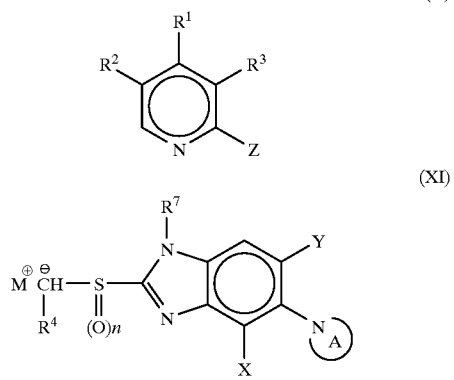

to prepare a compound of formula (I); or iv) converting the compounds of formula (I) obtained in i); ii) or iii) described above into pharmaceutically acceptable salts, or pharmaceutically acceptable solvates which firther comprises reacting the compound of formula (I) with 1 to 4 equivalents of a base or acid.

12. A compound of formula (I)

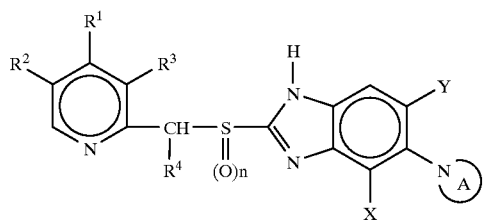

its tautomeric foxms, its stereoisomers, its polymorphs, its pharmaceutically acceptable salts or its pharmaceutically acceptable solvates, wherein X and Y are the same or different and independently represent a hydrogen, halogen, or optionally halogenated $(C_1-C_6)$alkoxy group, optionally hatogenated$(C_1-C_6)$alkyl group; A represents a substituted or unsubstituted 3 to 7 membered nitrogen containing heterocycle excluding substituted or unsubstituted pyrroles; or A represents a substituted or tsubstituted 5 to 7 membered nitrogen containing heterocycle containing one additional or two additional heteroatomns selected from N, O, S or a group $NR^5$ where $R^5$ represents hydrogen, $(C_1-C_6)$alkyl, aralkyl, acyl, alkoxycarbonyl, aryloxycarbonyl, or aralkoxycarbonyl; the heterocycle A is saturated or contains one, two or three double bonds, the heterocycle A, is linked specifcally through N-atom to the benzimidazole moiety; $R^4$ represents hydrogen, halogen or $(C_1-C_3)$alkyl group; $R^2$ and $R^3$ are the same or different and independently represent hydrogen, halogen, nitro, cyano, or optionally substituted groups selected from amino, $(C_1-C_6)$alkyl, $(C_1-C_6)$alkoxy, aryloxy or aralkoxy groups; $R^1$ may be hydrogen, halogen, or substituted or unsubstituted groups selected from $(C_1-C_8)$ alkyl, aryl, aralkyl, $(C_3-C_{10})$cycloalkyl, $(C_1-C_6)$alkylthio, $(C_1-C_6)$alkenylthio, heterocyclyl, amino, $(C_1-C_8)$ alkylamino, dialkylamino, arylamino, diarylamino, alkylarylamino, $(C_1-C_6)$alkoxy, $(C_2-C_6)$acyloxy, $(C_3-C_{10})$ cyclo-alkyloxy, aralkoxy, aryloxy, alkoxyalkoxy, or a group $-O-(CH_2)_m-O-(CH_2)_p-R^6$ where m is an integer ranging from 1 to 10 and p is an integer ranging from 0 to 3 and $R^6$ is a linear or branched $(C_1-C_6)$alkyl, heterocyclyl, heteroaryl, aralkyl, hydroxy, alkoxy, aryloxy, aralkoxy, alkoxycarbonyl, alkoxyalkyl or alkoxyalkoxy; and n is zero, prepared according to the process of claim 9.

13. A compound of formula (I)

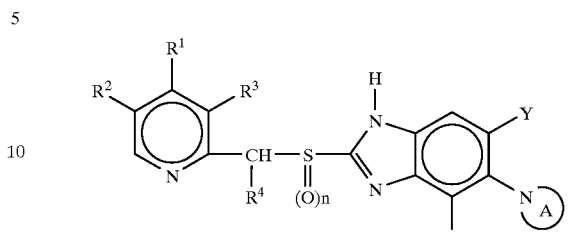

its tautomeric forms, its stereoisomers, its polymorphs, its pharmaceutically acceptable salts or its pharmaceutically acceptable solvates, wherein X and Y are the same or different and independently represent a hydrogen, halogen, or optionally halogenated $(C_1-C_6)$alkoxy group, optionally halogenated$(C_1-C_6)$alkyl group; A represents a substituted or unsubstituted 3 to 7 membered nitrogen containing heterocycle excluding substituted or unsubstituted pyrroles; or A represents a substituted or unsubstituted 5 to 7 membered nitrogen containing heterocycle containing one additional or two additional heteroatoms selected from N, O, S or a group $NR^5$ where $R^5$ represents hydrogen, $(C_1-C_6)$alkyl, aralkyl, acyl, alkoxycarbonyl, aryloxycarbonyl, or aralkoxycarbonyl; the heterocycle A is saturated or contains one, two or three double bonds, the heterocycle A, is linked specifically through N-atom to the benzidazole moiety; $R^4$ represents hydrogen, halogen or $(C_1-C_3)$alkyl group; $R_2$ and $R^3$ are the same or different and independently represent hydrogen, halogen, nitro, cyano, or optionally substituted groups selected from amino, $(C_1-C_6)$alkyl, $(C_1-C_6)$alkoxy, aryloxy or aralkoxy groups; $R^1$ may be hydrogen, halogen, or substituted or unsubstituted groups selected from $(C_1-C_8)$ alkyl, aryl, aralkyl, $(C_3-C_{10})$cycloalkyl, $(C_1-C_6)$alkylthio, $(C_1-C_6)$alkenylthio, heterocyclyl, amino, $(C_1-C_8)$ alkylamino, dialkylamino, arylamino, diarylamino, alkylarylamino, $(C_1-C_6)$alkoxy, $(C_1-C_6)$aryl oxy, $(C_3-C_{10})$ cyclo-alkyloxy, aralkoxy, aryloxy, alkoxyalkoxy, or a group $-O-(CH_2)_m-O-(CH_2)_p-R^6$ where m is an integer ranging from 1 to 10 and p is an integer ranging from 0 to 3 and $R^6$ is a linear or branched $(C_1-C_6)$alkyl, heterocyclyl, heteroaryl, aralkyl, hydroxy, alkoxy, aryloxy, aralkoxy, alkoxycarbonyl, alkoxyalkyl, or alkoxyalkoxy; and n is one, with a proviso that $R^1$ represents alkoxy group, and n is 1, $R^3$ does not represent hydrogen and A does not represent unsubstituted piperidinyl or unsubstituted pyrrolidinyl group prepared according to the process of claim 10.

14. A compound of formula (I)

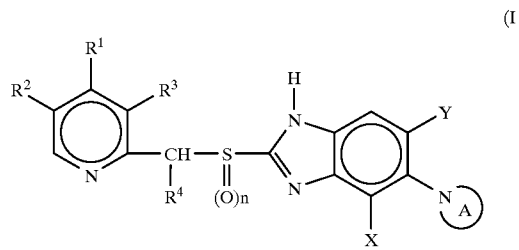

its tautomeric forms, its stereoisomers, its polymorphs, its pharmaceutically acceptable salts or its pharmaceutically acceptable solvates, wherein X and Y are the same or different and independently represent a hydrogen, halogen, or optionally halogenated ($C_1$–$C_6$)alkoxy group, optionally halogenated($C_1$–$C_6$)alkyl group; A represents a substituted or unsubstituted 3 to 7 membered nitrogen containing heterocycle excluding substituted or unsubstituted pyrroles; or A represents a substituted or unsubstituted 5 to 7 membered nitrogen containing heterocycle containing one additional or two additional heteroatoms selected from N, O, S or a group $NR^5$ where $R^5$ represents hydrogen, ($C_1$–$C_6$)alkyl, aralkyl, acyl, alkoxycarbonyl, aryloxycarbonyl, or aralkoxycarbonyl; the heterocycle A is saturated or contains one, two or three double bonds, the heterocycle A, is linked specifically through N-atom to the benzimidazole moiety; $R^4$ represents hydrogen, halogen or ($C_1$–$C_3$)alkyl group ; $R^2$ and $R^3$ are the same or different and independently represent hydrogen, halogen, nitro, cyano, or optionally substituted groups selected from amino, ($C_1$–$C_6$)alkyl, ($C_1$–$C_6$)alkoxy, aryloxy or aralkoxy groups; $R^1$ may be hydrogen, halogen, or substituted or unsubstituted groups selected from ($C_1$–$C_8$) alkyl, aryl, aralkyl, ($C_3$–$C_{10}$)cycloalkyl, ($C_1$–$C_6$)alkylthio, ($C_1$–$C_6$)alkenylthio, heterocyclyl, amino, ($C_1$–$C_8$) alkylamino, dialkylamino, arylamino, diarylamino, alkylarylamino, ($C_1$–$C_6$)alkoxy, ($C_2$–$C_6$)acyloxy, ($C_3$–$C_{10}$) cyclo-alkyloxy, aralkoxy, aryloxy, alkoxyalkoxy, or a group -O—($CH_2$)$_m$-O—($CH_2$)$_p$-$R^6$ where m is an integer ranging from 1 to 10 and p is an integer ranging from 0 to 3 and $R^6$ is a linear or branched ($C_1$–$C_6$)alkyl, heterocyclyl, heteroaryl, aralkyl, hydroxy, alkoxy, aryloxy, aralkoxy, alkoxycaxbonyl, alkoxyalkyl, or alkoxyalkoxy; and n is two, prepared according to the process of claim 11.

15. A method for treating gastric and duodenal ulcers, or for controlling Helicobacter pylori in a patient comprising administering an effective amount of a compound as claimed in claim 1 to a patient in need thereof.

16. A composition which comprises an effective amount of compound of formula (I)

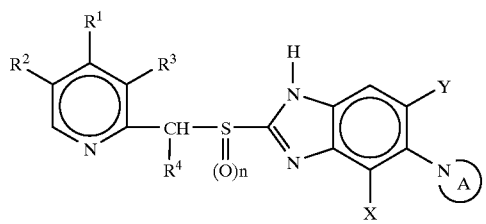

as defined in claim 1 and pharmaceutically acceptable carriers, diluents, excipients or solvates.

17. A composition as claimed in claim 16, in the form of a tablet, capsule, powder, syrup, solution or suspension.

18. A method for treating gastric and duodenal ulcers or for controlling Helicobacter pylori in a patient comprising adiministerng an effective amount of a compound as claimed in claim 1, and a pharmaceutically acceptable additive, carrier, diluent or excipient to a patient in need thereof.

19. A compound according to claim 1 which is selected from the group consisting of the following compounds: 2-[[(4-Methoxy-3,5-dimethyl)pyridin-2-yl]methylthio]-6-fluoro-5-(imidazol-1-yl)-1H-benzimidazole; 2-[[3-Methyl-4-(2,2,2-trifluoroethoxy)pyridin-2-yl]methylthio]-6-fluoro-5-(imidazol-1-yl)-1H-benzimidazole; 2-[[(4-Methoxy-3-methyl)pyridin-2-yl]methylthio]-6-fluoro-5-(imidazol-1-yl)-1H-benzimidazole; 2-[[(4-(3-Methoxypropoxy)-3-methyl)pyridin-2-yl]methylthio]-6-fluoro-5-(imidazol-1-yl)-1H-benzimidazole; 2-[[(4-Methoxy)pyridin-2-yl]methylthio]-6-fluoro-5-(imidazol-1-yl)-1H-benzimidazole; 2-[[(4-Chloro-3-methyl)pyridin-2-yl]methylthio]-6-fluoro-5-(imidazol-1-yl)-1H-benzimidazole; 2-[[(4-Methoxy-3,5-dimethyl)pyridin-2-yl]methylthio]-6-fluoro-5-(morpholin-1-yl)-1H-benzimidazole; 2-[[3-Methyl-4-(2,2,2-trifluoroethoxy)pyridin-2-yl]methylthio]-6-fluoro-5-(morpholin-1-yl)-1H-benzimidazole; 2-[[(4-Methoxy-3-methyl)pyridin-2-yl]methylthio]-6-fluoro-5-(morpholin-1-yl)-1H-benzimidazole; 2-[[(4-(3-Methoxypropoxy)-3-methyl)pyridin-2-yl]methylthio]-6-fluoro-5-(morpholin-1-yl)-1H-benzimidazole; 2-[[(4-Morpholin-1-yl)-3-methylpyridin-2-yl]methylthio]-6-fluoro-5-(morpholin-1-yl)-1H-benzimidazole; 2-[[(4-Piperidin-1-yl)-3-methylpyridin-2-yl]methylthio]-6-fluoro-5-(morpholin-1-yl)-1H-benzimidazole; 2-[[(4-Methylpiperazin-1-yl)-3-methylpyridin-2-yl]methylthio]-6-fluoro-5-(morpholin-1-yl)-1H-benzimidazole; 2-[[(3-Methyl)pyridin-2-yl]methylthio]-6-fluoro-5-(morpholin-1-yl)-1H-benzimidazole; 2-[[(4-Methoxy-3,5-dimethyl)pyridin-2-yl]methylthio]-6-fluoro-5-(piperidin-1-yl)-1H-benzimidazole; 2-[[3-Methyl-4-(2,2,2-trifluoroethoxy)pyridin-2-yl]methylthio]-6-fluoro-5-(piperidin-1-yl)-1H-benzimidazole; 2-[[(4-Methoxy-3-methyl)pyridin-2-yl]methylthio]-6-fluoro-5-(piperidin-1-yl)-1H-benzimidazole; 2-[[(4-Piperidin-1-yl)-3-methylpyridin-2-yl]methylthio]-6-fluoro-5-(piperidin-1-yl)-1H-benzimidazole; 2-[[(4-Methoxy-3,5-dimethyl)pyridin-2-yl]methylthio]-6-fluoro-5-(4-methylpiperazin-1-yl)-1H-benzimidazole; 2-[[3-Methyl-4-(2,2,2-trifluoroethoxy)pyridin-2-yl]methylthio]-6-fluoro-5-(4-methylpiperazin-1-yl)-1H-benzimidazole; 2-[[(4-Methoxy-3-methyl)pyridin-2-yl]methylthio]-6-fluoro-5-(4-methylpiperazin-1-yl)-1H-benzimidazole; 2-[[(3-Methyl)pyridin-2-yl]methylthio]-6-fluoro-5-(4-methylpiperazin-1-yl)-1H-benzimidazole; 2-[[(4-Methoxy-3,5-dimethyl)pyridin-2-yl]methylthio]-6-fluoro-5-(4-t-butyloxycarbonylpiperazin-1-yl)-1H-benzimidazole; 2-[[(4-Methoxy-3-methyl)pyridin-2-yl]methylthio]-6-fluoro-5-(4-t-butyloxycarbonylpiperazin-1-yl)-1H-benzimidazole; 2-[[(4-Methoxy-3-methyl)pyridin-2-yl]methylthio]-6-fluoro-5-(4-(ethylenedioxy)piperidin-1-yl)-1H-benzimidazole; 2-[[(4-Methoxy-3-methyl)pyridin-2-yl]methylthio]-6-fluoro-5-(4-piperidon-1-yl)-1H-benzimidazole); 2-[[(4-Methoxy-3-methyl)pyridin-2-yl]methylthio]-6-fluoro-5-(4-(hydroxyimino)piperidin-1-yl)-1H-benzimidazole; 2-[[(4-Methoxy-3-methyl)pyridin-2-yl]methylthio]-6-fluoro-5-[4-(hydroxy)piperidin-1-yl]-1H-benzimidazole; 2-[[(4-Methoxy-3-methyl)pyridin-2-yl]methylthio]-6-fluoro-5-(hexamethyleneimin-1-yl)-1H-benzimidazole; 2-[[(4-Morpholin-1-yl)-3-methyl)pyridin-2-yl]methylthio]-6-fluoro-5-(hexamethyleneirnin-1-yl)-1H-benzimidazole; 2-[[(4-Methoxy-3-methyl)pyridin-2-yl]methylthio]-6-fluoro-5-(2-(methoxymethyl)pyrrolidin-yl)-1H-benzimidazole; 2-[[(4-Methoxy-3-methyl)pyridin-2-yl]methylthio]-6-fluoro-5-(pyrroidin-1-yl)-1H-benzimidazole; 2-[[(4-Methoxy-3,5-dimethyl)pyridin-2-yl]methylthio]-5-(morpholin-1-yl)-1H-benzimidazole; 2-[[3-Methyl-4-(2,2,2-trifluoroethoxy)pyridin-2-yl]methylthio]-5-(morpholin-1-yl)-1H-benzimidazole; 2-[[(4-Methoxy-3-methyl)pyridin-2-yl]methylthio]-5-(morpholin-1-yl)-1H-benzimidazole; 2-[[(4-Methoxy-3,5-dimethyl)pyridin-2-yl]methylthio]-5-(4-methylpiperazin-1-yl)-1H-benzimidazole; 2-[[(4-Methoxy-3-methyl)pyridin-2-yl]methylthio]-5-(4-methylpiperazin-1-yl)-1H-benzimidazole; 2-[[(4-Methoxy-3-methyl)pyridin-2-yl]methylthio]-5-(4-t-butyloxycarbonylpiperazin-1-yl)-1H-benzimidazole; 2-[[(4-Methoxy-3-methyl)pyridin-2-yl]methylthio]-5-(piperidin-1-yl)-1H-benzimidazole; 2-[[(4-Methoxy-3-methyl)pyridin-2-yl]methylthio]-5-(hexamethyleneimin-1-yl)-1H-benzimidazole; 2-[[(4-Methoxy-3-methyl)pyridin-2-yl]methylthio]-4,6-difluoro-5-(morpholin-1-yl)-1H-benzimidazole; 2-[[(4-Methoxy-3,5-dimethyl)pyridin-2-yl]methylthio]-4,6-difluoro-5-(4-methylpiperazin-1-yl)-1H-benzimidazole; 2-[[(4-Methoxy-3,5-dimethyl)pyridin-2-yl]

methylsulfinyl]-6-fluoro-5-(imidazol-1-yl)-1H-benzimidazole; 2-[[(4-Methoxy-3,5-dimethyl)pyridin-2-yl]methylsulfinyl]-6-fluoro-5-(imidazol-1-yl)-1H-benzimidazole, sodium salt; 2-[[(4-Methoxy-3,5-dimethyl)pyridin-2-yl]methylsulfonyl]-6-fluoro-5-(imidazol-1-yl)-1H-benzimidazole; 2-[[3-Methyl-4-(2,2,2-trifluoroethoxy)pyridin-2-yl]methylsulfinyl]-6-fluoro-5-(imidazol-1-yl)-1H-benzimidazole; 2-[[3-Methyl-4-(2,2,2-trifluoroethoxy)pyridin-2-yl]methylsulfinyl]-6-fluoro-5-(imidazol-1-yl)-1H-benzimidazole, sodium salt; 2-[[(4-Methoxy-3-methyl)pyridin-2-yl]methylsulfinyl]-6-fluoro-5-(imidazol-1-yl)-1H-benzimidazole; 2-[[(4-(3-Methoxypropoxy)-3-methyl)pyridin-2-yl]methylsulfinyl]-6-fluoro-5-(imidazol-1-yl)-1H-benzimidazole; 2-[[(4-Methoxy)pyridin-2-yl]methylsulfinyl]-6-fluoro-5-(imidazol-1-yl)-1H-benzimidazole; 2-[[(4-Methoxy)pyridin-2-yl]methylsulfinyl]-6-fluoro-5-(imidazol-1-yl)-1H-benzimidazole, sodium salt; 2-[[(4-Chloro-3-methyl)pyridin-2-yl]methylsulfinyl]-6-fluoro-5-(imidazol-1-yl)-1H-benzimidazole; 2-[[(4-Methoxy-3,5-dimethyl)pyridin-2-yl]methylsulfinyl]-6-fluoro-5-(morpholin-1-yl)-1H-benzimidazole; 2-[[(4-Methoxy-3,5-dimethyl)pyridin-2-yl]methylsulfinyl]-6-fluoro-5-(morpholin-1-yl)-1H-benzimidazole, sodium salt; 2-[[3-Methyl-4-(2,2,2-trifluoroethoxy)pyridin-2-yl]methylsulfinyl]-6-fluoro-5-(morpholin-1-yl)-1H-benzimidazole; 2-[[3-Methyl-4-(2,2,2-trifluoroethoxy)pyridin-2-yl]methylsulfinyl]-6-fluoro-5-(morpholin-1-yl)-1H-benzimidazole, sodium salt; 2-[[(4-Methoxy-3-methyl)pyridin-2-yl]methylsulfinyl]-6-fluoro-5-(morpholin-1-yl)-1H-benzimidazole; 2-[[(4-Methoxy-3-methyl)pyridin-2-yl]methylsulfinyl]-6-fluoro-5-(morpholin-1-yl)-1H-benzimidazole, sodium salt; 2-[[(4-(3-Methoxypropoxy)-3-methyl)pyridin-2-yl]methylsulfinyl]-6-fluoro-5-(morpholin-1-yl)-1H-benzimidazole; 2-[[4-(Morpholin-1-yl)-3-methylpyridin-2-yl]methylsulfinyl]-6-fluoro-5-(morpholin-1-yl)-1H-benzimidazole; 2-[[4-(Morpholin-1-yl)-3-methylpyridin-2-yl]methylsulfinyl]-6-fluoro-5-(morpholin-1-yl)-1H-benzimidazole, sodium salt; 2-[[(4-Piperidin-1-yl)-3-methylpyridin-2-yl]methylsulfinyl]-6-fluoro-5-(morpholin-1-yl)-1H-benzimidazole; 2-[[(3-Methyl)pyridin-2-yl]methylsulfinyl]-6-fluoro-5-(morpholin-1-yl)-1H-benzimidazole; 2-[[(4-Methoxy-3,5-dimethyl)pyridin-2-yl]methylsulfinyl]-6-fluoro-5-(piperidin-1-yl)-1H-benzimidazole; 2-[[(4-Methoxy-3,5-dimethyl)pyridin-2-yl]methylsulfinyl]-6-fluoro-5-(piperidin-1-yl)-1H-benzimidazole, sodium salt; 2-[[3 -Methyl-4-(2,2,2-trifluoroethoxy)pyridin-2-yl]methylsulfinyl]-6-fluoro-5-(piperidin-1-yl)-1H-benzimidazole; 2-[[(4-Methoxy-3-methyl)pyridin-2-yl]methylsulfinyl]-6-fluoro-5-(piperidin-1-yl)-1H-benzimidazole; 2-[[(4-Methoxy-3-methyl)pyridin-2-yl]methylsulfinyl]-6-fluoro-5-(piperidin-1-yl)-1H-benzimidazole, sodium salt; 2-[[(4-Piperidin-1-yl)-3-methyl)pyridin-2-yl]methylsulfinyl]-6-fluoro-5-(piperidin-1-yl)-1H-benzimidazole; 2-[[(4-Methoxy-3,5-dimethyl)pyridin-2-yl]methylsulfinyl]-6-fluoro-5-(4-methylpiperazin-1-yl)-1H-benzimidazole; 2-[[3-Methyl-4-(2,2,2-trifluoroethoxy)pyridin-2-yl]methylsulfinyl]-6-fluoro-5-(4-methylpiperazin-1-yl)-1H-benzimidazole; 2-[[(4-Methoxy -3,5-dimethyl)pyridin-2-yl]methylsulfinyl]-6-fluoro-5-(4-t-butyloxycarbonylpiperazin-1-yl)-1H-benzimidazole; 2-[[(4-Methoxy-3-methyl)pyridin-2-yl]methylsulfinyl]-6-fluoro-5-(4-t-butyloxycarbonylpiperazin-1-yl)-1H-benzimidazole; 2-[[(4-Methoxy-3-methyl)pyridin-2-yl]methylsulfinyl]-6-fluoro-5-(4-(ethylenedioxy)piperidin-1-yl)-1H-benzimidazole; 2-[[(4-Methoxy-3-methyl)pyridin-2-yl]methylsulfinyl]-6-fluoro-5-(4-(ethylenedioxy)piperidin-1-yl)-1H-benzimidazole, sodium salt; 2-[[(4-Methoxy-3-methyl)pyridin-2-yl]methylsulfinyl]-6-fluoro-5-(4-piperidon-1-yl)-1H-benzimidazole; 2-[[(4-Methoxy-3-methyl)pyridin-2-yl]methylsulfinyl]-6-fluoro-5-(4-piperidon-1-yl)-1H-benzimidazole, sodium salt; 2-[[(4-Methoxy-3-methyl)pyridin-2-yl]methylsulfinyl]-6-fluoro-5-(4-(hydroxyimino)piperidin-1-yl)-1H-benzimidazole; 2-[[(4-Methoxy-3-methyl)pyridin-2-yl]methylsulfinyl]-6-fluoro-5-(4-hydroxypiperidin-1-yl)-1H-benzimidazole; 2-[[(4-Methoxy-3-methyl)pyridin-2-yl]methylsulfinyl]-6-fluoro-5-(hexamethyleneimin-1-yl)-1H-benzimidazole; 2-[[(4-Methoxy-3-methyl)pyridin-2-yl]methylsulfinyl]-6-fluoro-5-(hexamethyleneimin-1-yl)-1H-benzimidazole, sodium salt; 2-[[(4-Morpholin-1-yl)-3-methyl)pyridin-2-yl]methylsulfinyl-6-fluoro-5-(hexamethyleneimin-1-yl)-1H-benzimidazole; 2-[[(4-Methoxy-3-methyl)pyridin-2-yl]methylsulfinyl]-6-fluoro-5-(2-methoxymethyl)pyrrolidin-1-yl)-1H-benzimidazole; 2-[[(4-Methoxy-3-methyl)pyridin-2-yl]methylsulfinyl]-6-fluoro-5-(pyrrolidin-1-yl)-1H-benzimidazole; 2-[[(4-Methoxy-3,5-dimethyl)pyridin-2-yl]methylsulfinyl]-5-(morpholin-1-yl)-1H-benzimidazole; 2-[[3-Methyl-4-(2,2,2-trifluoroethoxy)pyridin-2-yl]methylsulfinyl]-5-(morpholin-1-yl)-1H-benzimidazole; 2-[[(4-Methoxy-3-methyl)pyridin-2-yl]methylsulfinyl]-5-(morpholin-1-yl)-1H-benzimidazole; 2-[[(4-Methoxy-3-methyl)pyridin-2-yl]methylsulfinyl]-5-(morpholin-1-yl)-1H-benzimidazole, sodium salt; 2-[[(4-Methoxy-3,5-dimethyl)pyridin-2-yl]methylsulfinyl]-5-(4-methylpiperazin-1-yl)-1H-benzimidazole; 2-[[(4-Methoxy-3-methyl)pyridin-2-yl]methylsulfinyl]-5-(4-t-butyloxycarbonylpiperazin-1-yl)-1H-benzimidazole; 2-[[(4-Methoxy-3-methyl)pyridin-2-yl]methylsulfinyl]-5-(hexamethyleneimin-1-yl)-1H-benzimidazole and 2-[[(4-Methoxy-3 -methyl)pyridin-2-yl]methylsulfinyl]-4,6-difluoro-5-(morpholin-1-yl)-1H-benzimidazole.

20. A composition which comprises an effective amount of compound according to claim 19 as an effective ingredient and a pharmaceutically acceptable additive, carrier, diluent or excipient.

21. A composition as claimed in claim 19, in the form of a tablet, capsule, powder, syrup, solution or suspension.

22. A method for treating gastric and duodenal ulcers or for controlling Helicobacter pylori in a patient comprising administering an effective amount of a compound as claimed in claim 19 and a pharmaceutically acceptable additive, carrier, diluent or solvates to patient in need thereof.

23. A method for inhibiting gastric acid secretion or for cytoprotecting the gastrointestnal tract in a patient comprising administering an effective gastric acid secretion inhibiting amount or an effective cytoprotective amount of a compound as claimed in claim 1 to a patient in need thereof.

24. A method for inhibiting gastric acid secretion or for cytoprotecting the gastrointestinal tract in a patient comprising administering an effective gastric acid secretion inhibiting amount or an effective cytoprotective amount of a compound as claimed in claim 1 and a pharmaceutically acceptable additive, carrier, diluent or excipient to a patient in need thereof.

25. A method for inhibiting gastric acid secretion or for cytoprotective the gastrointestinal tract in a patient comprising administering an effective gastric acid secretion inhibiting amount or an effective cytoprotective amount of a compound as claimed in claim 19 and a pharmaceutically acceptable additive, carrier, diluent or excipient to a patient in need thereof.

* * * * *

UNITED STATES PATENT AND TRADEMARK OFFICE
CERTIFICATE OF CORRECTION

PATENT NO. : 6,051,570

DATED : April 18, 2000

INVENTOR(S) : Braj Bhushan Lohray; Vidya Bhushan Lohray; Prasuna Guntupalli; Narayan Reddy Kommireddi; Prem Kumar Mamnoor; Rajagopalan Ramanujam It is certified that error appears in the above-identified patent and that said Letters Patent are hereby corrected as shown below:

On the title page, insert - - [30] Foreign Application Priority Date May 30, 1997 [IN] India 1152/MAS/97 - -

Signed and Sealed this

First Day of May, 2001

Attest:

NICHOLAS P. GODICI

Attesting Officer

Acting Director of the United States Patent and Trademark Office